(12) United States Patent
Sartor et al.

(10) Patent No.: US 7,879,033 B2
(45) Date of Patent: Feb. 1, 2011

(54) ELECTROSURGICAL PENCIL WITH ADVANCED ES CONTROLS

(75) Inventors: Joe D. Sartor, Longmont, CO (US); Robert Behnke, Erie, CO (US); Steven P. Buysse, Longmont, CO (US); Chris J. Ehr, Longmont, CO (US); David N. Heard, Boulder, CO (US); Mark J. Huseman, Broomfield, CO (US); Ronald J. Podhajsky, Boulder, CO (US); Arlan J. Reschke, Longmont, CO (US); Dale F. Schmaltz, Fort Collins, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 1066 days.

(21) Appl. No.: 11/337,990

(22) Filed: Jan. 24, 2006

(65) Prior Publication Data

US 2006/0178667 A1 Aug. 10, 2006

Related U.S. Application Data

(63) Continuation-in-part of application No. 11/198,473, filed on Aug. 5, 2005, now Pat. No. 7,503,917, which is a continuation-in-part of application No. 10/959,824, filed on Oct. 6, 2004, now Pat. No. 7,156,842, which is a continuation-in-part of application No. PCT/US03/37111, filed on Nov. 20, 2003.

(51) Int. Cl.
*A61B 18/14* (2006.01)

(52) U.S. Cl. .......................................... 606/45; 606/49

(58) Field of Classification Search .................. 606/34, 606/46, 49, 45
See application file for complete search history.

(56) References Cited

U.S. PATENT DOCUMENTS 2,031,682 A 2/1936 Frederick et al.

(Continued)

FOREIGN PATENT DOCUMENTS

DE 24 60 481 A1 6/1976

(Continued)

OTHER PUBLICATIONS

Zucker, Karl A. Surgical Laparscopy. Lippincott Williams & Wilkins, Ed. 2, 2001.*

(Continued)

*Primary Examiner*—Thomas J Sweet
*Assistant Examiner*—Jaymi Della

(57) ABSTRACT

An electrosurgical system is provided that includes an electrosurgical generator; and an electrosurgical pencil selectively connectable to the electrosurgical generator. The electrosurgical pencil includes an elongated housing; at least one electrocautery end effector removably supportable within the housing and extending distally from the housing, the electrocautery end effector being connected to the electrosurgical generator; and at least one voltage divider network supported on the housing. The at least one voltage divider network is electrically connected to the electrosurgical generator and controls at least one of the intensity of electrosurgical energy being delivered to the electrosurgical pencil and the mode of electrosurgical energy being delivered to the electrosurgical pencil. The voltage divider network generates a plurality of characteristic voltages which are measurable by the electrosurgical generator and which electrosurgical generator in turn transmits a corresponding waveform duty cycle at a particular intensity to the electrocautery end effector of the electrosurgical pencil.

32 Claims, 33 Drawing Sheets

U.S. PATENT DOCUMENTS

| | | |
|---|---|---|
| 2,102,270 A | 12/1937 | Hyams |
| 2,993,178 A | 7/1961 | Burger |
| 3,058,470 A | 10/1962 | Seeliger et al. |
| 3,219,029 A | 11/1965 | Richards et al. |
| 3,460,539 A | 8/1969 | Anhalt, Sr. |
| 3,494,363 A | 2/1970 | Jackson |
| 3,648,001 A | 3/1972 | Anderson et al. |
| 3,675,655 A | 7/1972 | Sittner |
| 3,699,967 A * | 10/1972 | Anderson .................... 606/37 |
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III |
| 3,828,780 A | 8/1974 | Morrison, Jr. |
| 3,875,945 A * | 4/1975 | Friedman .................... 606/45 |
| 3,902,494 A | 9/1975 | Haberlen et al. |
| 3,906,955 A | 9/1975 | Roberts |
| 3,911,241 A | 10/1975 | Jarrard |
| 3,967,084 A | 6/1976 | Pounds |
| 3,974,833 A | 8/1976 | Durden, III |
| 4,014,343 A | 3/1977 | Esty |
| 4,032,738 A | 6/1977 | Esty et al. |
| 4,034,761 A | 7/1977 | Prater et al. |
| 4,038,984 A | 8/1977 | Sittner |
| 4,112,950 A | 9/1978 | Pike |
| D253,247 S | 10/1979 | Gill |
| 4,232,676 A | 11/1980 | Herczog |
| 4,314,559 A | 2/1982 | Allen |
| 4,427,006 A | 1/1984 | Nottke |
| 4,443,935 A | 4/1984 | Zamba et al. |
| 4,459,443 A | 7/1984 | Lewandowski |
| 4,463,234 A | 7/1984 | Bennewitz |
| 4,463,759 A | 8/1984 | Garito et al. |
| 4,492,231 A | 1/1985 | Auth |
| 4,492,832 A | 1/1985 | Taylor |
| 4,545,375 A * | 10/1985 | Cline .......................... 606/42 |
| 4,562,838 A | 1/1986 | Walker |
| 4,589,411 A | 5/1986 | Friedman |
| 4,593,691 A | 6/1986 | Lindstrom et al. |
| 4,595,809 A | 6/1986 | Pool |
| 4,606,342 A | 8/1986 | Zamba et al. |
| 4,619,258 A | 10/1986 | Pool |
| 4,620,548 A | 11/1986 | Hasselbrack |
| 4,625,723 A | 12/1986 | Altnether et al. |
| 4,640,279 A | 2/1987 | Beard |
| 4,642,128 A | 2/1987 | Solorzano |
| 4,655,215 A | 4/1987 | Pike |
| 4,657,016 A | 4/1987 | Garito et al. |
| 4,683,884 A | 8/1987 | Hatfield et al. |
| 4,688,569 A | 8/1987 | Rabinowitz |
| 4,701,193 A | 10/1987 | Robertson et al. |
| 4,712,544 A | 12/1987 | Ensslin |
| 4,735,603 A | 4/1988 | Goodson et al. |
| 4,754,754 A | 7/1988 | Garito et al. |
| 4,785,807 A | 11/1988 | Blanch |
| 4,788,977 A | 12/1988 | Farin et al. |
| 4,794,215 A | 12/1988 | Sawada et al. |
| 4,796,623 A | 1/1989 | Krasner et al. |
| 4,803,323 A | 2/1989 | Bauer et al. |
| 4,811,733 A | 3/1989 | Borsanyi et al. |
| 4,827,911 A | 5/1989 | Broadwin et al. |
| 4,827,927 A | 5/1989 | Newton |
| D301,739 S | 6/1989 | Turner et al. |
| 4,846,790 A | 7/1989 | Hornlein et al. |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,869,715 A | 9/1989 | Sherburne |
| 4,872,454 A | 10/1989 | DeOliveira et al. |
| 4,876,110 A | 10/1989 | Blanch |
| 4,886,060 A | 12/1989 | Wiksell |
| 4,901,719 A | 2/1990 | Trenconsky et al. |
| 4,903,696 A | 2/1990 | Stasz et al. |
| 4,909,249 A | 3/1990 | Akkas et al. |
| 4,911,159 A | 3/1990 | Johnson et al. |
| 4,916,275 A | 4/1990 | Almond |
| 4,919,129 A | 4/1990 | Weber, Jr. et al. |
| 4,921,476 A | 5/1990 | Wuchinich |
| 4,922,903 A | 5/1990 | Welch et al. |
| 4,931,047 A | 6/1990 | Broadwin et al. |
| 4,949,734 A | 8/1990 | Bernstein |
| 4,969,885 A | 11/1990 | Farin |
| 4,986,839 A | 1/1991 | Wertz et al. |
| 4,988,334 A | 1/1991 | Hornlein et al. |
| 5,000,754 A | 3/1991 | DeOliveira et al. |
| 5,011,483 A | 4/1991 | Sleister |
| 5,013,312 A | 5/1991 | Parins et al. |
| 5,015,227 A | 5/1991 | Broadwin et al. |
| 5,026,368 A | 6/1991 | Adair |
| 5,035,695 A | 7/1991 | Weber, Jr. et al. |
| 5,035,696 A * | 7/1991 | Rydell .......................... 606/47 |
| 5,046,506 A | 9/1991 | Singer |
| 5,055,100 A | 10/1991 | Olsen |
| 5,071,418 A | 12/1991 | Rosenbaum |
| 5,074,863 A | 12/1991 | Dines |
| 5,076,276 A | 12/1991 | Sakurai et al. |
| 5,088,997 A | 2/1992 | Delahuerga et al. |
| 5,098,430 A | 3/1992 | Fleenor |
| 5,100,402 A | 3/1992 | Fan |
| 5,108,391 A | 4/1992 | Flachenecker et al. |
| 5,133,714 A | 7/1992 | Beane |
| 5,147,292 A | 9/1992 | Kullas et al. |
| D330,253 S | 10/1992 | Burek |
| 5,154,709 A | 10/1992 | Johnson |
| 5,160,334 A | 11/1992 | Billings et al. |
| 5,162,044 A | 11/1992 | Gahn et al. |
| 5,167,659 A | 12/1992 | Ohtomo et al. |
| 5,178,012 A | 1/1993 | Culp |
| 5,178,605 A | 1/1993 | Imonti |
| 5,190,517 A | 3/1993 | Zieve et al. |
| 5,190,541 A | 3/1993 | Abele et al. |
| 5,192,267 A | 3/1993 | Shapira et al. |
| 5,195,959 A | 3/1993 | Smith |
| 5,196,007 A | 3/1993 | Ellman et al. |
| 5,197,962 A | 3/1993 | Sansom et al. |
| 5,199,944 A | 4/1993 | Cosmescu |
| 5,217,457 A | 6/1993 | Delahuerga et al. |
| 5,224,944 A | 7/1993 | Elliott |
| 5,226,904 A | 7/1993 | Gentelia et al. |
| 5,233,515 A | 8/1993 | Cosman |
| 5,234,428 A | 8/1993 | Kaufman |
| 5,234,429 A | 8/1993 | Goldhaber |
| 5,242,442 A | 9/1993 | Hirschfeld |
| 5,244,462 A | 9/1993 | Delahuerga et al. |
| 5,246,440 A | 9/1993 | Van Noord |
| 5,254,082 A | 10/1993 | Takase |
| 5,254,117 A | 10/1993 | Rigby et al. |
| 5,256,138 A | 10/1993 | Burek et al. |
| 5,261,906 A | 11/1993 | Pennino et al. |
| 5,269,781 A | 12/1993 | Hewell, III |
| 5,300,087 A | 4/1994 | Knoepfler |
| 5,304,763 A | 4/1994 | Ellman et al. |
| 5,306,238 A | 4/1994 | Fleenor |
| 5,312,329 A | 5/1994 | Beaty et al. |
| 5,312,400 A | 5/1994 | Bales et al. |
| 5,312,401 A | 5/1994 | Newton et al. |
| 5,318,516 A | 6/1994 | Cosmescu |
| 5,318,565 A | 6/1994 | Kuriloff et al. |
| 5,322,503 A | 6/1994 | Desai |
| 5,330,470 A | 7/1994 | Hagen |
| 5,334,183 A | 8/1994 | Wuchinich |
| 5,342,356 A | 8/1994 | Ellman et al. |
| 5,348,555 A | 9/1994 | Zinnanti |

| | | | | | | |
|---|---|---|---|---|---|---|
| 5,366,464 | A | 11/1994 | Belknap | 5,893,849 A | 4/1999 | Weaver |
| 5,376,089 | A | 12/1994 | Smith | 5,893,862 A | 4/1999 | Pratt et al. |
| 5,380,320 | A | 1/1995 | Morris | 5,913,864 A | 6/1999 | Garito et al. |
| 5,382,247 | A | 1/1995 | Cimino et al. | 5,919,219 A | 7/1999 | Knowlton |
| 5,395,363 | A | 3/1995 | Billings et al. | 5,928,159 A | 7/1999 | Eggers et al. |
| 5,399,823 | A | 3/1995 | McCusker | 5,938,589 A | 8/1999 | Wako et al. |
| 5,401,273 | A | 3/1995 | Shippert | 5,941,887 A | 8/1999 | Steen et al. |
| 5,403,882 | A | 4/1995 | Huggins | 5,944,737 A | 8/1999 | Tsonton et al. |
| 5,406,945 | A | 4/1995 | Riazzi et al. | 5,951,548 A | 9/1999 | DeSisto et al. |
| 5,409,484 | A | 4/1995 | Erlich et al. | 5,951,581 A | 9/1999 | Saadat et al. |
| 5,413,575 | A | 5/1995 | Haenggi | 5,954,686 A | 9/1999 | Garito et al. |
| 5,421,829 | A | 6/1995 | Olichney et al. | 5,972,007 A | 10/1999 | Sheffield et al. |
| 5,423,838 | A | 6/1995 | Willard | 6,004,318 A | 12/1999 | Garito et al. |
| 5,431,645 | A | 7/1995 | Smith et al. | 6,004,333 A | 12/1999 | Sheffield et al. |
| 5,431,650 | A | 7/1995 | Cosmescu | 6,004,335 A | 12/1999 | Vaitekunas et al. |
| 5,451,222 | A | 9/1995 | De Maagd et al. | 6,010,499 A | 1/2000 | Cobb |
| 5,460,602 | A | 10/1995 | Shapira | 6,022,347 A | 2/2000 | Lindenmeier et al. |
| 5,462,522 | A | 10/1995 | Sakurai et al. | 6,045,564 A | 4/2000 | Walen |
| 5,468,240 | A | 11/1995 | Gentelia et al. | 6,063,050 A | 5/2000 | Manna et al. |
| 5,472,442 | A | 12/1995 | Klicek | 6,068,603 A | 5/2000 | Suzuki |
| 5,472,443 | A | 12/1995 | Cordis et al. | 6,068,627 A | 5/2000 | Orszulak et al. |
| 5,484,398 | A | 1/1996 | Stoddard | 6,070,444 A | 6/2000 | Lontine et al. |
| 5,484,434 | A | 1/1996 | Cartmell et al. | 6,071,281 A | 6/2000 | Burnside et al. |
| 5,486,162 | A | 1/1996 | Brumbach | 6,074,386 A | 6/2000 | Goble et al. |
| 5,496,314 | A | 3/1996 | Eggers | 6,074,387 A | 6/2000 | Heim et al. |
| 5,498,654 | A | 3/1996 | Shimasaki et al. | 6,086,544 A | 7/2000 | Hibner et al. |
| D370,731 | S | 6/1996 | Corace et al. | 6,090,123 A | 7/2000 | Culp et al. |
| 5,531,722 | A | 7/1996 | Van Hale | 6,099,525 A | 8/2000 | Cosmescu |
| 5,549,604 | A | 8/1996 | Sutcu et al. | 6,117,134 A | 9/2000 | Cunningham et al. |
| 5,561,278 | A | 10/1996 | Rutten | 6,139,547 A | 10/2000 | Lontine et al. |
| 5,599,346 | A | 2/1997 | Edwards et al. | D433,752 S | 11/2000 | Saravia |
| 5,601,224 | A | 2/1997 | Bishop et al. | 6,142,995 A | 11/2000 | Cosmescu |
| 5,609,573 | A | 3/1997 | Sandock | 6,146,353 A | 11/2000 | Platt, Jr. |
| 5,626,575 | A | 5/1997 | Crenner | 6,149,648 A | 11/2000 | Cosmescu |
| 5,630,417 | A * | 5/1997 | Petersen et al. ............. 600/443 | 6,156,035 A | 12/2000 | Songer |
| 5,630,426 | A | 5/1997 | Eggers et al. | 6,197,024 B1 | 3/2001 | Sullivan |
| 5,630,812 | A | 5/1997 | Ellman et al. | 6,200,311 B1 | 3/2001 | Danek et al. |
| 5,633,578 | A | 5/1997 | Eggers et al. | D441,077 S | 4/2001 | Garito et al. |
| 5,634,912 | A | 6/1997 | Injev | 6,213,999 B1 | 4/2001 | Platt, Jr. et al. |
| 5,634,935 | A | 6/1997 | Taheri | 6,214,003 B1 | 4/2001 | Morgan et al. |
| 5,643,256 | A | 7/1997 | Urueta | 6,238,388 B1 | 5/2001 | Ellman et al. |
| D384,148 | S | 9/1997 | Monson | 6,241,723 B1 | 6/2001 | Heim et al. |
| 5,669,907 | A | 9/1997 | Platt, Jr. et al. | 6,241,753 B1 | 6/2001 | Knowlton |
| 5,674,219 | A | 10/1997 | Monson et al. | 6,249,706 B1 | 6/2001 | Sobota et al. |
| 5,693,044 | A | 12/1997 | Cosmescu | 6,251,110 B1 | 6/2001 | Wampler |
| 5,693,050 | A | 12/1997 | Speiser | 6,257,241 B1 | 7/2001 | Wampler |
| 5,693,052 | A | 12/1997 | Weaver | 6,258,088 B1 | 7/2001 | Tzonev et al. |
| 5,697,926 | A | 12/1997 | Weaver | 6,273,862 B1 | 8/2001 | Privitera et al. |
| 5,702,360 | A | 12/1997 | Dieras et al. | 6,277,083 B1 | 8/2001 | Eggers et al. |
| 5,702,387 | A | 12/1997 | Arts et al. | 6,286,512 B1 | 9/2001 | Loeb et al. |
| 5,712,543 | A | 1/1998 | Sjostrom | 6,287,305 B1 | 9/2001 | Heim et al. |
| 5,713,895 | A | 2/1998 | Lontine et al. | 6,287,344 B1 | 9/2001 | Wampler et al. |
| 5,720,745 | A | 2/1998 | Farin et al. | 6,312,441 B1 | 11/2001 | Deng |
| D393,067 | S | 3/1998 | Geary et al. | 6,325,799 B1 | 12/2001 | Goble |
| 5,749,869 | A | 5/1998 | Lindenmeier et al. | D453,222 S | 1/2002 | Garito et al. |
| 5,765,418 | A | 6/1998 | Rosenberg | D453,833 S | 2/2002 | Hess |
| 5,776,092 | A | 7/1998 | Farin et al. | 6,350,276 B1 | 2/2002 | Knowlton |
| 5,788,688 | A | 8/1998 | Bauer et al. | 6,352,544 B1 | 3/2002 | Spitz |
| 5,797,907 | A | 8/1998 | Clement | 6,355,034 B2 | 3/2002 | Cosmescu |
| 5,800,431 | A | 9/1998 | Brown | 6,358,281 B1 | 3/2002 | Berrang et al. |
| 5,836,897 | A | 11/1998 | Sakurai et al. | 6,361,532 B1 | 3/2002 | Burek |
| 5,836,909 | A | 11/1998 | Cosmescu | D457,955 S | 5/2002 | Bilitz |
| 5,836,944 | A | 11/1998 | Cosmescu | 6,386,032 B1 | 5/2002 | Lemkin et al. |
| D402,030 | S | 12/1998 | Roberts et al. | 6,395,001 B1 | 5/2002 | Ellman et al. |
| D402,031 | S | 12/1998 | Roberts et al. | 6,402,741 B1 | 6/2002 | Keppel et al. |
| 5,843,109 | A | 12/1998 | Mehta et al. | 6,402,742 B1 | 6/2002 | Blewett et al. |
| 5,846,236 | A | 12/1998 | Lindenmeier et al. | 6,402,743 B1 | 6/2002 | Orszulak et al. |
| 5,859,527 | A | 1/1999 | Cook | 6,402,748 B1 | 6/2002 | Schoenman et al. |
| 5,868,768 | A | 2/1999 | Wicherski et al. | 6,409,725 B1 | 6/2002 | Khandkar et al. |
| 5,876,400 | A | 3/1999 | Songer | 6,413,255 B1 | 7/2002 | Stern |
| 5,879,347 | A | 3/1999 | Saadat | 6,416,491 B1 | 7/2002 | Edwards et al. |
| 5,888,200 | A | 3/1999 | Walen | 6,416,509 B1 | 7/2002 | Goble et al. |
| 5,893,848 | A | 4/1999 | Negus et al. | 6,425,912 B1 | 7/2002 | Knowlton |

| | | |
|---|---|---|
| 6,458,122 B1 | 10/2002 | Pozzato |
| 6,458,125 B1 | 10/2002 | Cosmescu |
| 6,461,352 B2 | 10/2002 | Morgan et al. |
| 6,464,702 B2 | 10/2002 | Schulze et al. |
| 6,471,659 B2 | 10/2002 | Eggers et al. |
| 6,494,882 B1 | 12/2002 | Lebouitz et al. |
| 6,500,169 B1 * | 12/2002 | Deng .......................... 606/1 |
| 6,511,479 B2 | 1/2003 | Gentelia et al. |
| 6,526,320 B2 | 2/2003 | Mitchell |
| 6,551,313 B1 | 4/2003 | Levin |
| 6,558,383 B2 | 5/2003 | Cunningham et al. |
| 6,585,664 B2 | 7/2003 | Burdorff et al. |
| 6,589,239 B2 | 7/2003 | Khandkar et al. |
| 6,610,054 B1 | 8/2003 | Edwards et al. |
| 6,610,057 B1 | 8/2003 | Ellman et al. |
| 6,616,658 B2 | 9/2003 | Ineson |
| 6,618,626 B2 | 9/2003 | West, Jr. et al. |
| 6,620,161 B2 | 9/2003 | Schulze et al. |
| 6,632,193 B1 | 10/2003 | Davison et al. |
| 6,652,514 B2 | 11/2003 | Ellman et al. |
| 6,662,053 B2 | 12/2003 | Borkan |
| 6,669,691 B1 | 12/2003 | Taimisto |
| 6,685,701 B2 | 2/2004 | Orszulak et al. |
| 6,685,704 B2 | 2/2004 | Greep |
| 6,702,812 B2 | 3/2004 | Cosmescu |
| 6,710,546 B2 | 3/2004 | Crenshaw |
| 6,712,813 B2 | 3/2004 | Ellman et al. |
| 6,719,746 B2 | 4/2004 | Blanco |
| 6,740,079 B1 | 5/2004 | Eggers et al. |
| 6,747,218 B2 | 6/2004 | Huseman et al. |
| D493,530 S | 7/2004 | Reschke |
| D493,888 S | 8/2004 | Reschke |
| D494,270 S | 8/2004 | Reschke |
| D495,051 S | 8/2004 | Reschke |
| D495,052 S | 8/2004 | Reschke |
| 6,794,929 B2 | 9/2004 | Pelly |
| 6,830,569 B2 | 12/2004 | Thompson et al. |
| 6,840,948 B2 | 1/2005 | Albrecht et al. |
| 6,855,140 B2 | 2/2005 | Albrecht et al. |
| 6,902,536 B2 | 6/2005 | Manna et al. |
| 6,905,496 B1 | 6/2005 | Ellman et al. |
| 6,923,804 B2 | 8/2005 | Eggers et al. |
| 6,923,809 B2 | 8/2005 | Eggers et al. |
| 6,939,347 B2 | 9/2005 | Thompson |
| 6,955,674 B2 | 10/2005 | Eick et al. |
| D515,412 S | 2/2006 | Waaler et al. |
| 7,033,353 B2 | 4/2006 | Stoddard et al. |
| D521,641 S | 5/2006 | Reschke et al. |
| D535,396 S | 1/2007 | Reschke et al. |
| 2001/0047183 A1 | 11/2001 | Privitera et al. |
| 2001/0049524 A1 | 12/2001 | Morgan et al. |
| 2002/0019596 A1 | 2/2002 | Eggers et al. |
| 2002/0019631 A1 | 2/2002 | Kidder et al. |
| 2002/0022838 A1 | 2/2002 | Cunningham et al. |
| 2002/0026145 A1 | 2/2002 | Bagaoisan et al. |
| 2002/0035364 A1 | 3/2002 | Schoenman et al. |
| 2002/0049427 A1 | 4/2002 | Wiener et al. |
| 2002/0058958 A1 | 5/2002 | Walen |
| 2002/0087179 A1 | 7/2002 | Culp et al. |
| 2002/0095199 A1 * | 7/2002 | West et al. .................. 607/101 |
| 2002/0103485 A1 | 8/2002 | Melnyk et al. |
| 2002/0111622 A1 | 8/2002 | Khandkar et al. |
| 2002/0133148 A1 | 9/2002 | Daniel et al. |
| 2002/0151886 A1 | 10/2002 | Wood |
| 2002/0151887 A1 | 10/2002 | Stern et al. |
| 2002/0156471 A1 | 10/2002 | Stern et al. |
| 2002/0173776 A1 | 11/2002 | Batchelor et al. |
| 2002/0198519 A1 | 12/2002 | Qin et al. |
| 2003/0004508 A1 * | 1/2003 | Morgan et al. ................ 606/41 |
| 2003/0014043 A1 | 1/2003 | Henry et al. |
| 2003/0032950 A1 | 2/2003 | Altshuler et al. |
| 2003/0050633 A1 | 3/2003 | Ellman et al. |
| 2003/0055421 A1 | 3/2003 | West et al. |
| 2003/0061661 A1 | 4/2003 | Borders et al. |
| 2003/0065321 A1 | 4/2003 | Carmel et al. |
| 2003/0078572 A1 | 4/2003 | Pearson et al. |
| 2003/0083655 A1 | 5/2003 | Van Wyk |
| 2003/0088247 A1 | 5/2003 | Ineson |
| 2003/0109864 A1 | 6/2003 | Greep et al. |
| 2003/0109865 A1 | 6/2003 | Greep et al. |
| 2003/0130663 A1 | 7/2003 | Walen |
| 2003/0144680 A1 | 7/2003 | Kellogg et al. |
| 2003/0163125 A1 | 8/2003 | Greep |
| 2003/0199856 A1 | 10/2003 | Hill et al. |
| 2003/0199866 A1 | 10/2003 | Stern et al. |
| 2003/0199869 A1 | 10/2003 | Johnson et al. |
| 2003/0212393 A1 | 11/2003 | Knowlton et al. |
| 2003/0212397 A1 | 11/2003 | Avrahami et al. |
| 2003/0216728 A1 | 11/2003 | Stern et al. |
| 2003/0220635 A1 | 11/2003 | Knowlton et al. |
| 2003/0220638 A1 | 11/2003 | Metzger |
| 2003/0225401 A1 | 12/2003 | Eggers et al. |
| 2003/0229341 A1 | 12/2003 | Albrecht et al. |
| 2003/0229343 A1 | 12/2003 | Albrecht et al. |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0010246 A1 | 1/2004 | Takahashi |
| 2004/0015160 A1 | 1/2004 | Lovewell |
| 2004/0015161 A1 | 1/2004 | Lovewell |
| 2004/0015162 A1 | 1/2004 | McGaffigan |
| 2004/0015216 A1 | 1/2004 | DeSisto |
| 2004/0024395 A1 | 2/2004 | Ellman et al. |
| 2004/0024396 A1 | 2/2004 | Eggers |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030367 A1 | 2/2004 | Yamaki |
| 2004/0034346 A1 | 2/2004 | Stern et al. |
| 2004/0054370 A1 | 3/2004 | Given |
| 2004/0092927 A1 | 5/2004 | Podhajsky et al. |
| 2004/0111087 A1 | 6/2004 | Stern et al. |
| 2004/0124964 A1 | 7/2004 | Wang et al. |
| 2004/0127889 A1 | 7/2004 | Zhang et al. |
| 2004/0143677 A1 | 7/2004 | Novak |
| 2004/0147909 A1 | 7/2004 | Johnston et al. |
| 2004/0162553 A1 | 8/2004 | Peng et al. |
| 2004/0167512 A1 | 8/2004 | Stoddard et al. |
| 2004/0172011 A1 | 9/2004 | Wang et al. |
| 2004/0172015 A1 | 9/2004 | Novak |
| 2004/0172016 A1 | 9/2004 | Bek et al. |
| 2004/0181140 A1 | 9/2004 | Falwell et al. |
| 2004/0230262 A1 | 11/2004 | Sartor et al. |
| 2004/0236323 A1 | 11/2004 | Schoenman et al. |
| 2004/0243120 A1 | 12/2004 | Orszulak et al. |
| 2004/0267252 A1 | 12/2004 | Washington et al. |
| 2004/0267254 A1 | 12/2004 | Manzo et al. |
| 2004/0267297 A1 | 12/2004 | Malackowski |
| 2005/0033286 A1 | 2/2005 | Eggers et al. |
| 2005/0059858 A1 | 3/2005 | Frith et al. |
| 2005/0059967 A1 | 3/2005 | Breazeale, Jr. et al. |
| 2005/0065510 A1 | 3/2005 | Carmel et al. |
| 2005/0070891 A1 | 3/2005 | DeSisto |
| 2005/0085804 A1 | 4/2005 | McGaffigan |
| 2005/0096645 A1 | 5/2005 | Wellman et al. |
| 2005/0096646 A1 | 5/2005 | Wellman et al. |
| 2005/0096681 A1 | 5/2005 | Desinger et al. |
| 2005/0107782 A1 | 5/2005 | Reschke |
| 2005/0113817 A1 | 5/2005 | Isaacson et al. |
| 2005/0113818 A1 | 5/2005 | Sartor et al. |
| 2005/0113823 A1 | 5/2005 | Reschke et al. |
| 2005/0113824 A1 | 5/2005 | Sartor et al. |
| 2005/0113825 A1 | 5/2005 | Cosmescu |
| 2005/0149001 A1 | 7/2005 | Uchikubo et al. |
| 2005/0154385 A1 | 7/2005 | Heim et al. |
| 2006/0041257 A1 | 2/2006 | Sartor et al. |

| | | | | | | | |
|---|---|---|---|---|---|---|---|
| 2006/0058783 | A1 | 3/2006 | Buchman | | WO | WO 02/47568 A1 | 6/2002 |
| 2006/0178667 | A1 | 8/2006 | Sartor et al. | | WO | WO 2004/010883 A1 | 2/2004 |
| 2006/0235378 | A1* | 10/2006 | Waaler .................. 606/41 | | WO | WO 2004/045436 | 6/2004 |
| 2007/0049926 | A1 | 3/2007 | Sartor | | WO | WO 2004/073753 A2 | 9/2004 |
| 2007/0093810 | A1 | 4/2007 | Sartor | | WO | WO 2005/060849 A1 | 7/2005 |

FOREIGN PATENT DOCUMENTS

| | | |
|---|---|---|
| DE | 30 45 996 | 7/1982 |
| DE | 3627221 * | 2/1988 |
| EP | 24 29 021 A1 | 1/1976 |
| EP | 0 186 369 A | 7/1986 |
| EP | 1050277 | 11/2000 |
| EP | 1050279 | 11/2000 |
| EP | 1082945 | 3/2001 |
| EP | 1293171 | 3/2003 |
| EP | 1 645 233 | 4/2006 |
| EP | 1645234 | 4/2006 |
| EP | 1656900 | 5/2006 |
| EP | 1852078 | 11/2007 |
| FR | 2235669 | 1/1975 |
| FR | 2798579 | 3/2001 |
| WO | WO94/20032 | 9/1994 |
| WO | WO 96/39086 | 12/1996 |
| WO | WO 98/43264 | 10/1998 |
| WO | WO01/64122 | 9/2001 |

OTHER PUBLICATIONS

ISR from EP 05019882.9 dated Feb. 16, 2006.
ISR from EP 05021777.7 dated Feb. 23, 2006.
European Search Report from Application EP 07009028 dated Jul. 16, 2007.
International Search Report from European Application No. EP 08 00 2357 dated Jun. 30, 2008.
International Search Report EP 06 005 540.7 dated Sep. 24, 2007.
International Search Report from EP 06 01 4461 dated Oct. 31, 2006.
International Search Report from PCT/US03/37111; Jul. 21, 2004.
International Search Report from PCT/US04/04685; Aug. 6, 2004.
International Search Report from EP/0401/5980; Sep. 30, 2004.
International Search Report from PCT/US03/22900; Nov. 20, 2003.
International Search Report from Application No. EP 06 00 6908 dated Feb. 25, 2009.
International Search Report from Application No. EP 08 02 1070 dated Apr. 1, 2009.

* cited by examiner

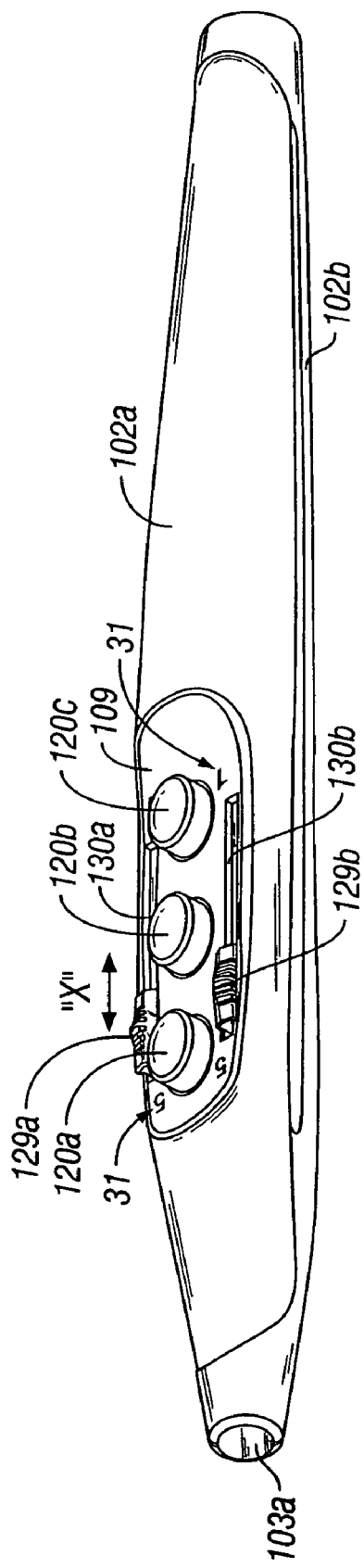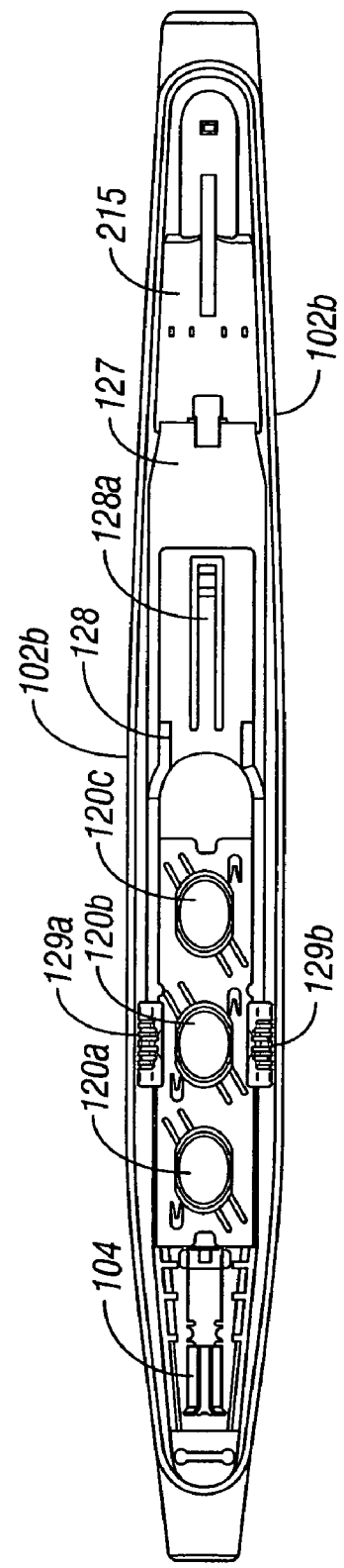
FIG. 10
FIG. 11

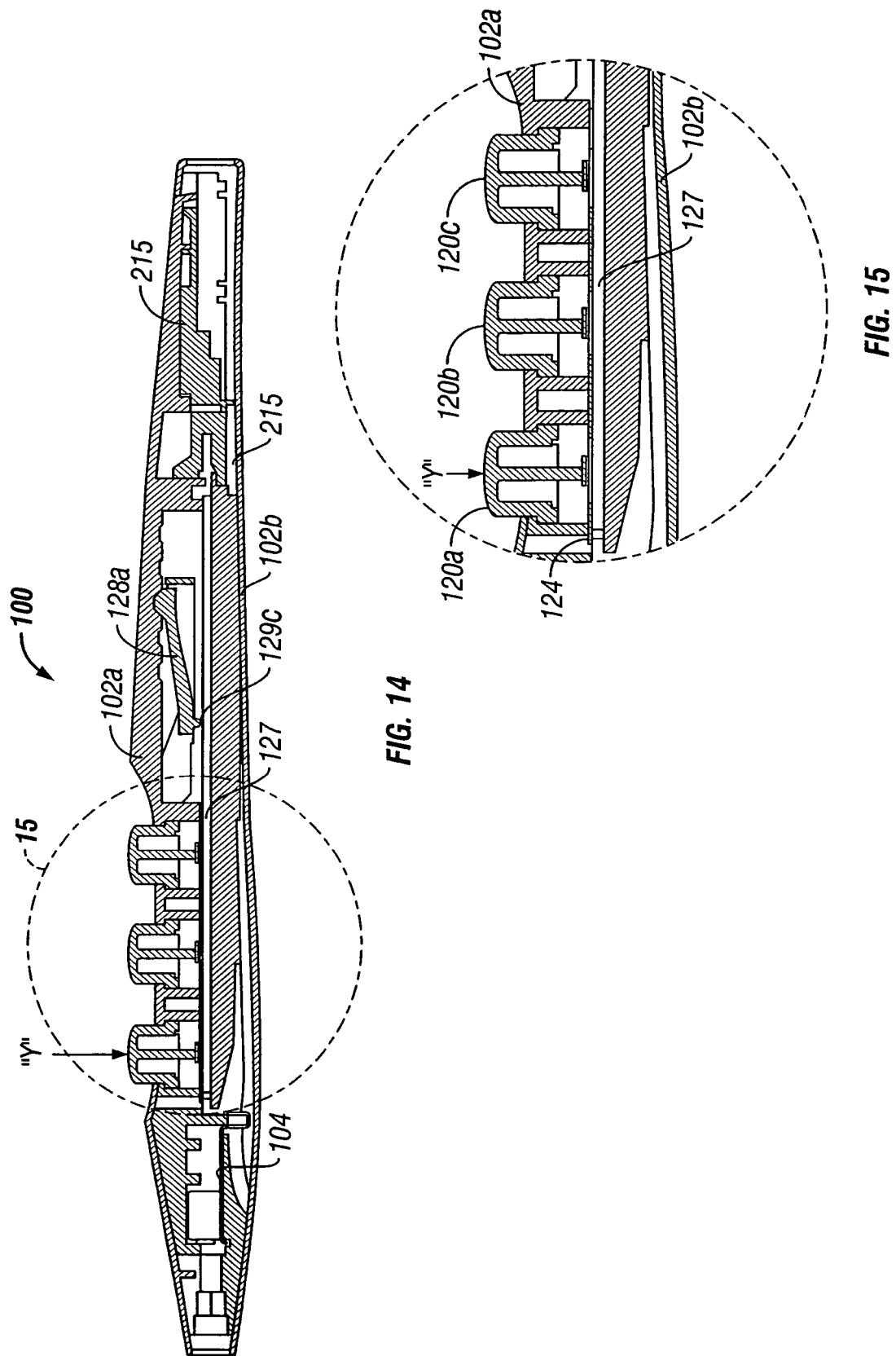

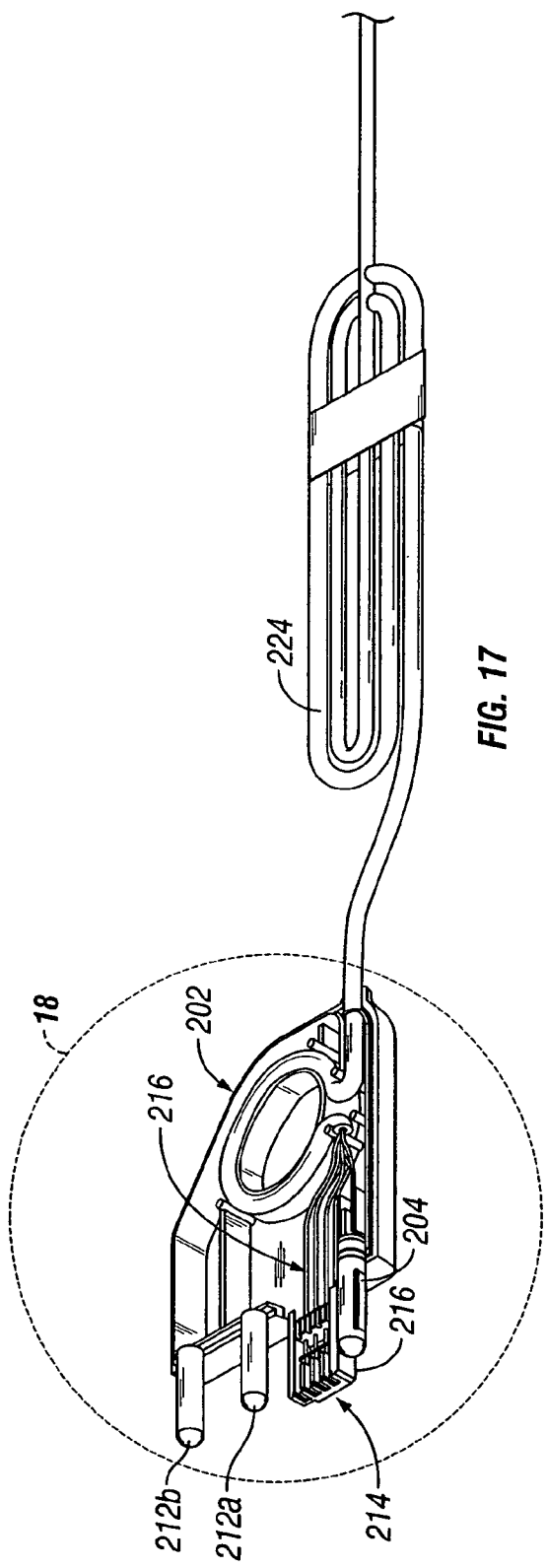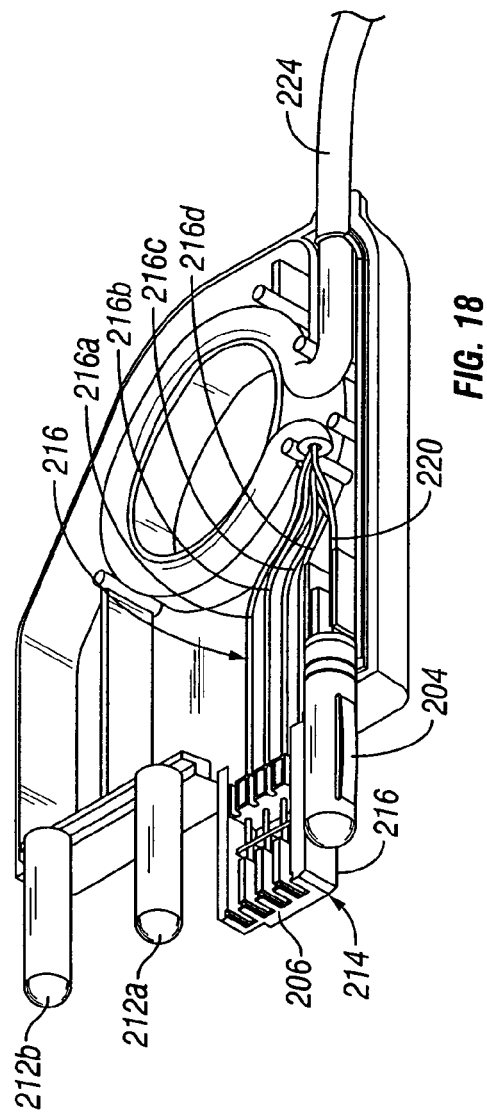

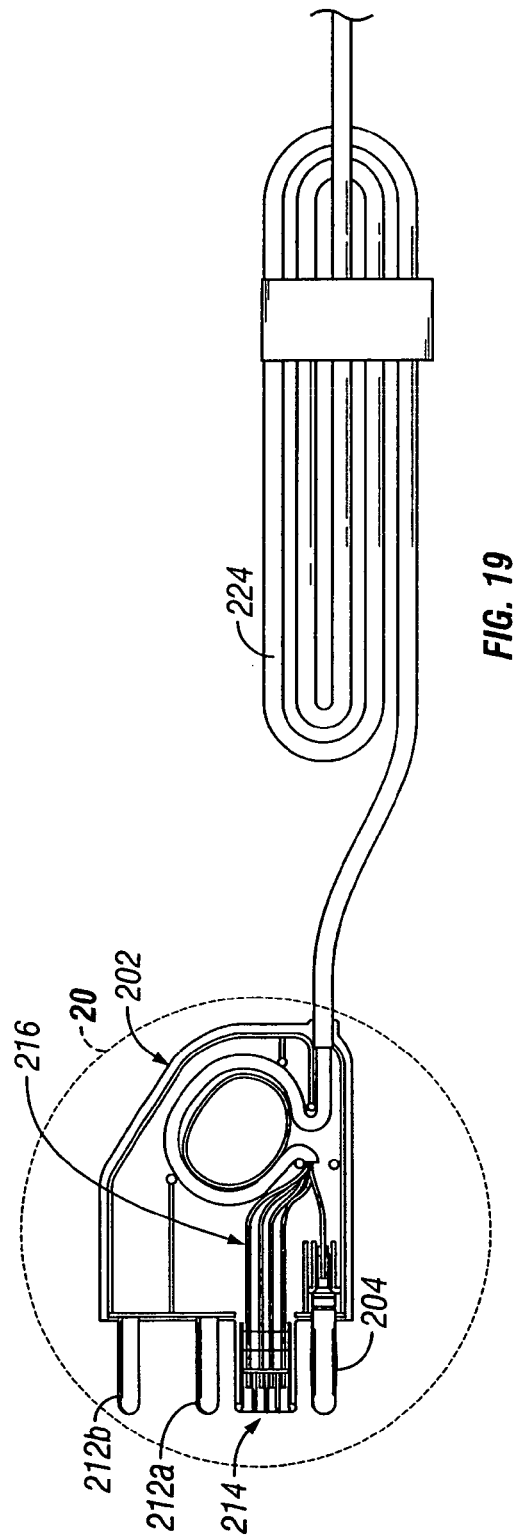
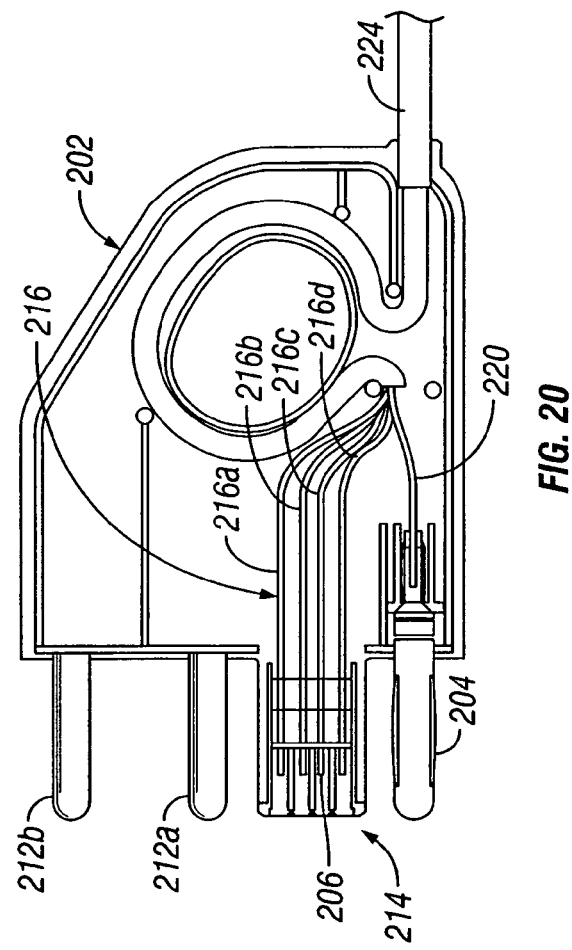
FIG. 19
FIG. 20

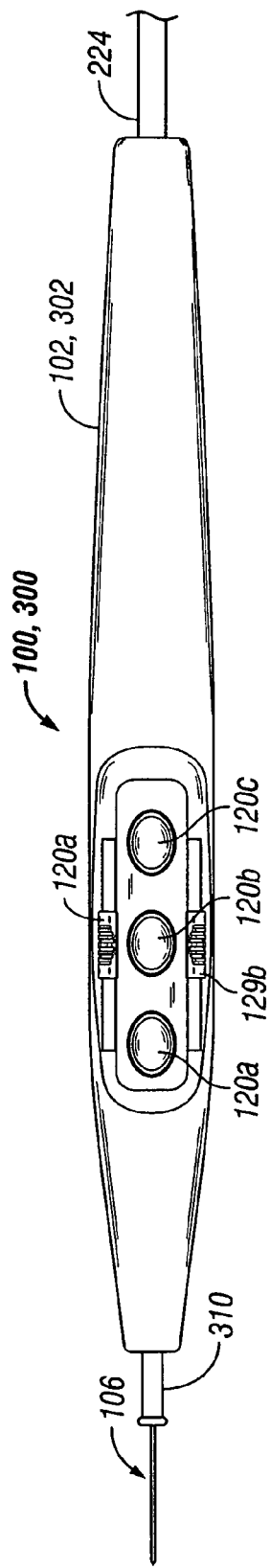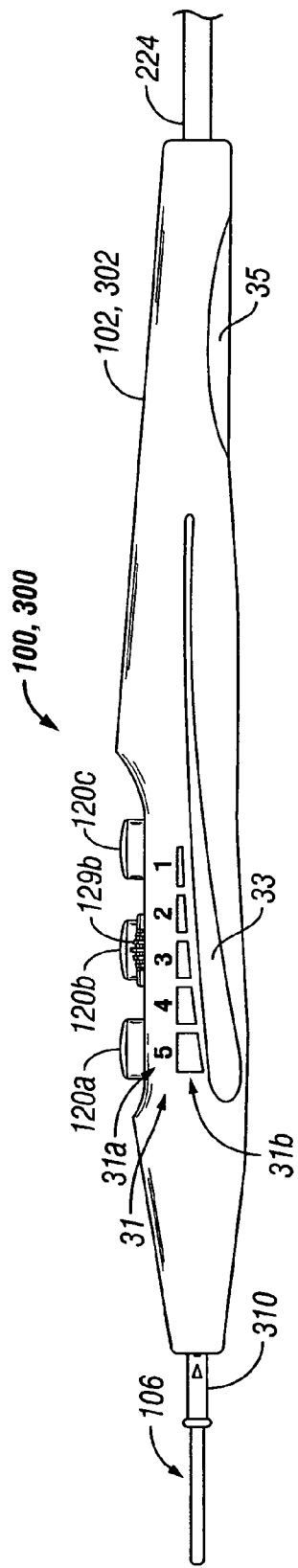
FIG. 29
FIG. 30

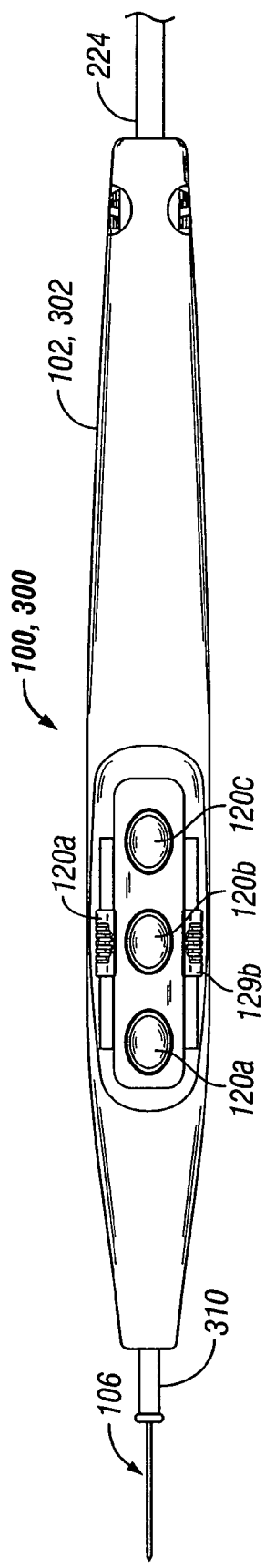
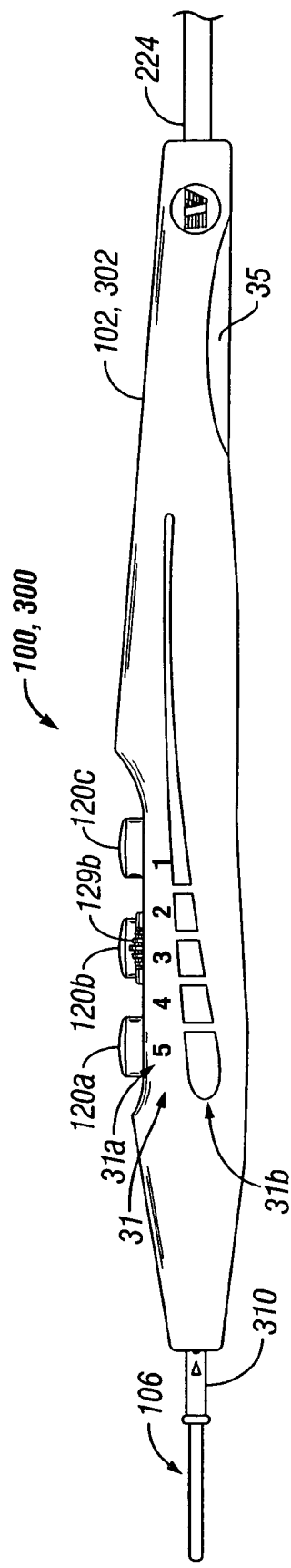
FIG. 31
FIG. 32

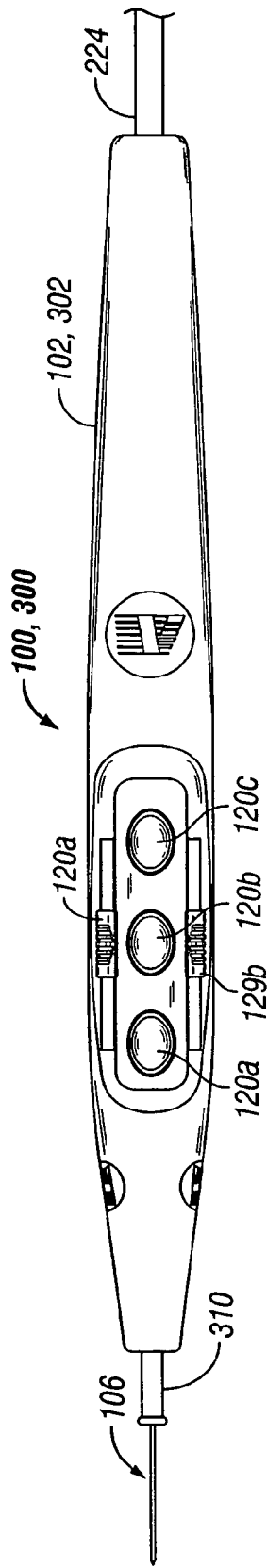
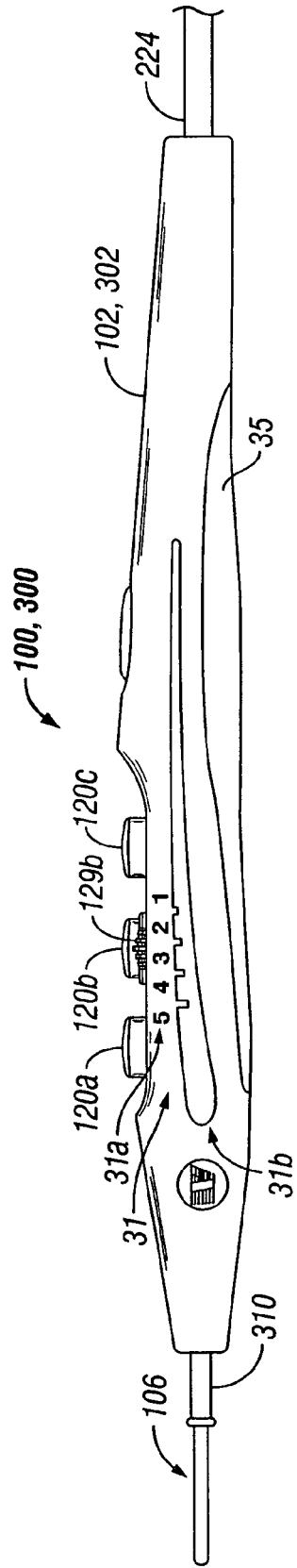
FIG. 33
FIG. 34

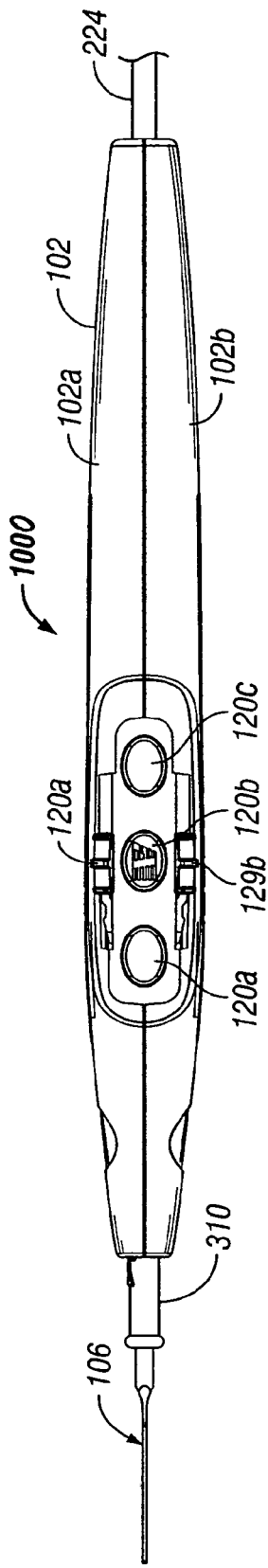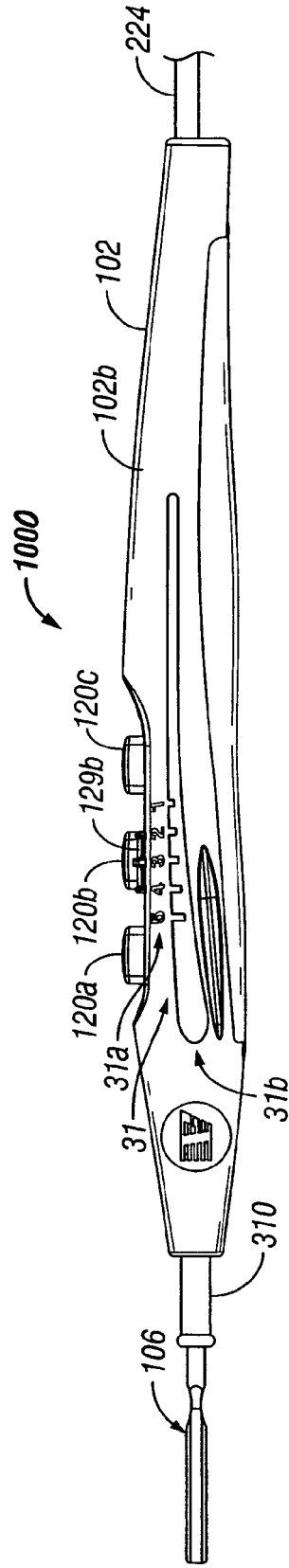
FIG. 39
FIG. 40

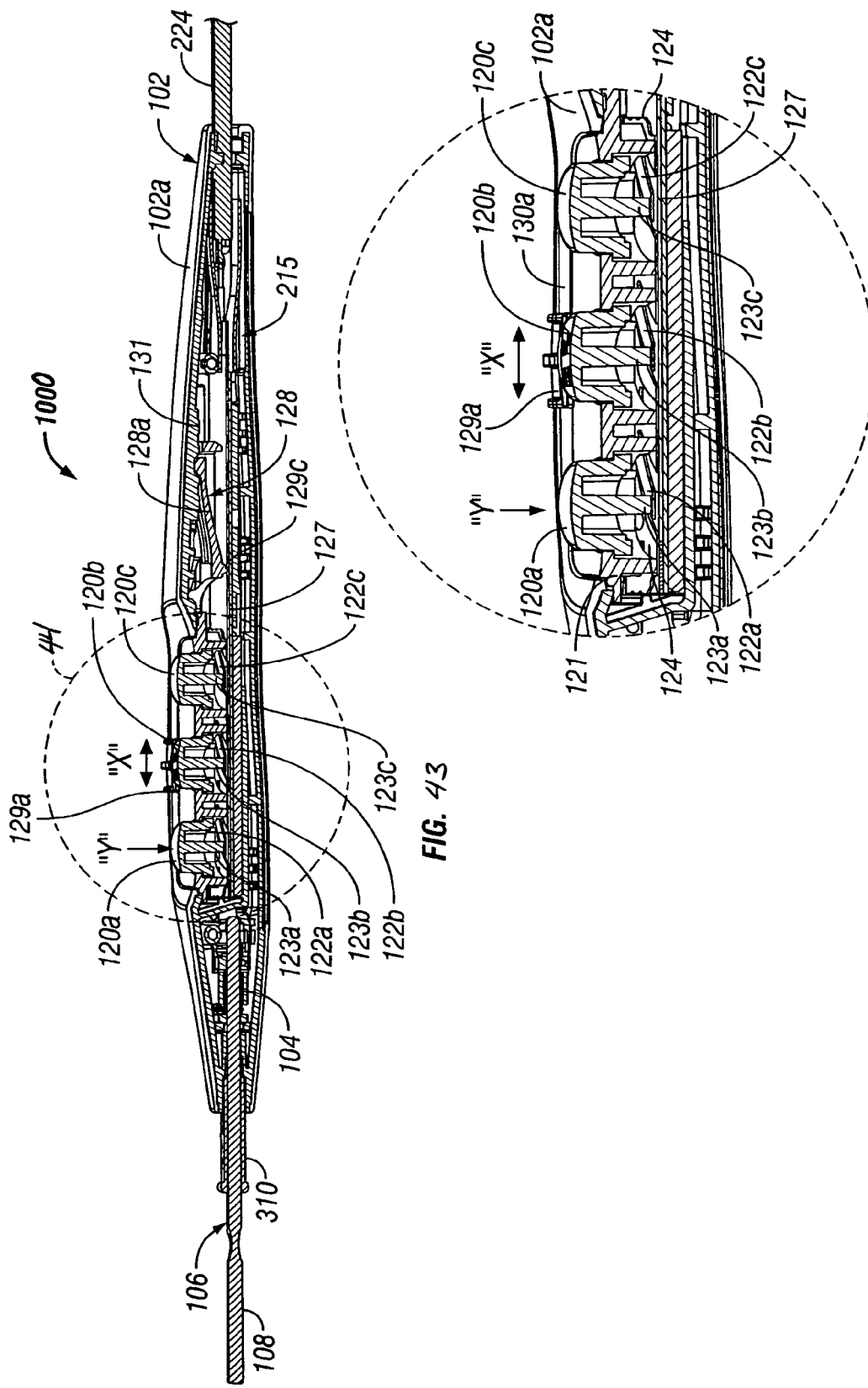

ELECTROSURGICAL PENCIL WITH ADVANCED ES CONTROLS

CROSS-REFERENCE TO RELATED APPLICATIONS

The present application is a Continuation-in-Part Application which claims the benefit of and priority to Continuation-in-Part application Ser. No. 11/198,473, filed Aug. 5, 2005, now U.S. Pat. No. 7,503,917, which claims the benefit of and priority to Continuation-in-Part application Ser. No. 10/959,824, filed on Oct. 6, 2004, now U.S. Pat. No. 7,156,842, which in turn claims the benefit of and priority to International Application No. PCT/US03/37111, filed on Nov. 20, 2003, the entire contents of both of which are incorporated herein by reference.

BACKGROUND

1. Technical Field

The present disclosure relates generally to electrosurgical instruments and, more particularly, to an electrosurgical pencil having a plurality of hand-accessible variable controls.

2. Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical cutting and fulguration.

In particular, electrosurgical fulguration includes the application of electric spark to biological tissue, for example, human flesh or the tissue of internal organs, without significant cutting. The spark is produced by bursts of radio-frequency electrical or electrosurgical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical pencil" is intended to include instruments which have a handpiece which is attached to an active electrode and which is used to cauterize, coagulate and/or cut tissue. Typically, the electrosurgical pencil may be operated by a handswitch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (i.e., generator) which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue, and a blend wave form tends to be somewhere between a cut and coagulate wave from. The power or energy parameters are typically controlled from outside the sterile field which requires an intermediary like a circulating nurse to make such adjustment.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue. However, so many options also tend to complicate simple surgical procedures and may lead to confusion. Moreover, surgeons typically follow preset control parameters and stay within known modes and power settings. Therefore, there exists a need to allow the surgeon to selectively control and easily select and regulate the various modes and power settings utilizing simple and ergonomically friendly controls associated with the electrosurgical pencil.

Existing electrosurgical instrument systems allow the surgeon to change between two pre-configured settings (i.e., coagulation and cutting) via two discrete switches disposed on the electrosurgical pencil itself. Other electrosurgical instrument systems allow the surgeon to increment the power applied when the coagulating or cutting switch of the instrument is depressed by adjusting or closing a switch on the electrosurgical generator. The surgeon then needs to visually verify the change in the power being applied by looking at various displays and/or meters on the electrosurgical generator. In other words, all of the adjustments to the electrosurgical instrument and parameters being monitored during the use of the electrosurgical instrument are typically located on the electrosurgical generator. As such, the surgeon must continually visually monitor the electrosurgical generator during the surgical procedure.

Recently, electrosurgical instrument systems have been increasingly provided with coupling and/or connecting systems (e.g., a plug) for removably connecting the electrosurgical instrument to the electrosurgical generator. Typically, the electrosurgical instrument is provided with a so called "male" connector while the electrosurgical generator is provided with the corresponding "female" connector.

Since electrosurgery requires controlled application of radio frequency energy to an operative tissue site, it is important that the appropriate electrosurgical generator be correctly and/or properly mated with the electrosurgical instrument for the specific electrosurgical procedure. Due to the variety of operative, electrosurgical procedures, requiring various levels of radio frequency energy delivery from an attached instrument, issues arise with the mismatching of electrosurgical instruments and electrosurgical generators.

Accordingly, the need exists for electrosurgical instruments which do not require the surgeon to continually monitor the electrosurgical generator during the surgical procedure. In addition, the need exists for electrosurgical instruments which may be configured such that the power output can be adjusted without the surgeon having to turn his/her vision away from the operating site and toward the electrosurgical generator.

Additionally, a need exists for a connecting system, for electrosurgical generators which allow various surgical instruments to be selectively connected to corresponding electrosurgical generators.

SUMMARY

The present disclosure relates to electrosurgical pencils having a plurality of hand-accessible variable controls.

According to an aspect of the present disclosure an electrosurgical pencil is provided including an elongated housing. At least one electrocautery end effector is removably supported within the housing and extends distally from the housing. The electrocautery end effector is connected to a source of electrosurgical energy and a selector is supported on the housing for selecting a range setting of energy to be delivered from the source of electrosurgical energy to the at least one electrocautery end effector. In use, the selector is actuatable to select a range setting corresponding to a particular electrocautery end effector connected to the housing.

The selector may be at least one of a button depressably supported on the housing or a collet rotatably supported on the housing. The range settings may be selected by at least one of depressing the button and rotating the collet.

The electrosurgical pencil may further include a plurality of activation switches supported on the housing. Each activation switch may be configured and adapted to selectively complete a control loop extending from the source of electrosurgical energy upon actuation thereof. In use, actuation of at least one of the plurality of activation switches produces tissue division with hemostatic effect at the electrocautery blade.

The electrosurgical pencil may further include at least one voltage divider network supported on the housing. The at least one voltage divider network is electrically connected to the source of electrosurgical energy and controls at least one of the intensity of electrosurgical energy being delivered to the electrosurgical pencil and the mode of electrosurgical energy being delivered to the electrosurgical pencil.

The division with hemostatic effect is transmitted in discrete packets of energy. The energy packet has a substantially instantaneous amplification and/or a substantially instantaneous degradation.

The housing defines an open distal end for selectively receiving a proximal end of the electrocautery blade therein. The open distal end of the housing may have a non-circular inner profile. The electrosurgical pencil may further include a collar operatively supporting the electrocautery blade. The collar has a shaped outer surface complementing the shaped inner profile of the distal open end of the housing. The collar and the inner profile of the distal open end of the housing may have complementary ovular, triangular, rectangular, hexagonal, toothed, multi-faceted profiles.

The electrosurgical pencil may further include a blade receptacle configured and adapted to selectively engage a proximal end of the electrocautery blade.

The electrosurgical pencil may further include a stabilizer operatively disposed within the housing for increasing retention forces acting on the proximal end of the electrocautery blade. The stabilizer defines a passage therein configured and adapted to selectively receive a proximal end of the electrocautery blade. The stabilizer may be fabricated from a compliant polymeric material.

The at least one voltage divider network may be electrically connected to the source of electrosurgical energy for controlling the intensity of electrosurgical energy being delivered to the plurality of activation switches from the source of electrosurgical energy and for controlling the intensity of electrosurgical energy delivered to the plurality of activation switches returning from the electrocautery electrode. The voltage divider network may include at least one return control wire electrically inter-connecting the electrocautery electrode and the source of electrosurgical energy. The return control wire transmits excess electrosurgical energy from the electrocautery electrode to the source of electrosurgical energy.

The voltage network divider includes a slide potentiometer operatively associated with the housing. The plurality of activation switches define a first resistor network disposed within the housing. The slide potentiometer defines a second resistor network disposed within the housing. The slide potentiometer simultaneously controls the intensity of electrosurgical energy delivered to the plurality of activation switches.

It is envisioned that at least one activation switch is configured and adapted to control a waveform duty cycle to achieve a desired surgical intent. The electrosurgical pencil may include three mode activation switches supported on the housing. Accordingly, each mode activation switch may generate a characteristic voltage which is measured by the source of electrosurgical energy, the source of electrosurgical energy in turn transmits a corresponding waveform duty cycle to the electrosurgical pencil.

A first activation switch, when actuated, may generate a first characteristic voltage measured by the source of electrosurgical energy, the source of electrosurgical energy in turn may transmit a waveform duty cycle which produces a cutting effect. A second activation switch, when actuated, may generate a second characteristic voltage measured by the source of electrosurgical energy, the source of electrosurgical energy in turn may transmit a waveform duty cycle which produces a division with hemostatic effect. A third activation switch, when actuated, may generate a third characteristic voltage measured by the source of electrosurgical energy, the source of electrosurgical energy in turn may transmit a waveform duty cycle which produces a coagulating effect.

The voltage divider network is desirably a potentiometer.

The electrosurgical pencil further includes a molded hand grip operatively supported on the housing. The hand grip is shaped and dimensioned to reduce fatigue on the hand of the user.

The electrosurgical pencil further includes indicia provided on the housing indicating to a user the level of energy intensity being delivered to the electrocautery blade. The indicium is typically located along a path of travel of the slide potentiometer.

In an embodiment it is envisioned that the selector is an optical fiber including a distal end supported in the housing for reading a light intensity from a proximal end of the electrocautery end effector when the electrocautery end effector is connected to the housing.

It is envisioned that a proximal end of each electrocautery end effector includes a unique color associated therewith, wherein each color produces a different light intensity.

Accordingly, when the electrocautery end effector is connected to the housing, the optical fiber transmits the light intensity to the electrosurgical generator. The electrosurgical generator, in turn, adjusts the range settings based on the light intensity transmitted thereto.

According to another aspect of the present disclosure, an electrosurgical system is provided. The electrosurgical system includes an electrosurgical generator; and an electrosurgical pencil selectively connectable to the electrosurgical generator. The electrosurgical pencil includes an elongated housing; at least one electrocautery end effector removably supportable within the housing and extending distally from the housing, the electrocautery end effector being connected to the electrosurgical generator; and at least one voltage divider network supported on the housing. The at least one voltage divider network is electrically connected to the electrosurgical generator and controls at least one of the intensity of electrosurgical energy being delivered to the electrosurgical pencil and the mode of electrosurgical energy being delivered to the electrosurgical pencil. The voltage divider network generates a plurality of characteristic voltages which are measurable by the electrosurgical generator and which electrosurgical generator in turn transmits a corresponding waveform duty cycle at a particular intensity to the electrocautery end effector of the electrosurgical pencil.

The voltage divider network may generate a first characteristic voltage which when measured by the electrosurgical generator causes the electrosurgical generator to transmit a waveform duty cycle which produces a cutting effect; a second characteristic voltage which when measured by the electrosurgical generator causes the electrosurgical generator to transmit a waveform duty cycle which produces a division with hemostatic effect; and a third characteristic voltage which when measured by the electrosurgical generator causes the electrosurgical generator to transmit a waveform duty cycle which produces a coagulating effect.

The voltage divider network may generate a series of characteristic voltages which, when measured by the electrosurgical generator, cause the electrosurgical generator to transmit the particular waveform duty cycle at a corresponding level of intensity.

The electrosurgical pencil may include a plurality of activation buttons supported on the housing. Each activation button may be operatively associated with the voltage divider network. Each activation button may be actuatable to cause the voltage divider network to generate a respective one of the characteristic voltages for transmission of a corresponding waveform duty cycle.

The electrosurgical pencil may include an intensity controller supported in the housing. The intensity controller may be operatively associated with the voltage divider network. The intensity controller may be actuatable to cause the voltage divider network to generate a respective one of the series of characteristic voltages for transmission of the waveform duty cycle at a corresponding intensity level. In an embodiment, the intensity controller is slidably supported in the housing of the electrosurgical pencil.

It is envisioned that the division with hemostatic effect has a waveform with a duty cycle of from about 12% to about 75%; that the coagulation effect has a waveform with a duty cycle of from about 1% to about 12%; and that the cutting effect has a waveform with a duty cycle of from about 75% to about 100%.

The voltage divider network may be a film-type potentiometer. The voltage divider network may include a pair of layers each supporting a plurality of electrical contacts thereon. It is envisioned that the electrical contacts from an upper layer of the voltage divider network are in juxtaposed electrical relation with respect to the electrical contacts from a lower layer of the voltage divider network. The voltage divider network may include a dividing layer interposed between the upper and lower layers. The dividing layer may include a first series of apertures formed therein which are in vertical registration with the electrical contacts of the upper and lower layers. The dividing layer may include a second aperture formed therein which is in vertical registration between electrical contacts provided on the upper layer and a variable resistance element provided on the lower layer.

According to a further aspect of the present disclosure, an electrosurgical instrument is provided and includes an elongated housing; at least one electrocautery end effector removably supportable within the housing and extending distally from the housing, the electrocautery end effector being connectable to an electrosurgical generator; and at least one voltage divider network supported on the housing, the at least one voltage divider network being electrically connectable to the electrosurgical generator, the at least one voltage divider network being capable of controlling at least one of the intensity of electrosurgical energy being delivered to the electrosurgical instrument and the mode of electrosurgical energy being delivered to the electrosurgical instrument. The voltage divider network generates a plurality of characteristic voltages which are measurable by the electrosurgical generator and which electrosurgical generator in turn transmits a corresponding waveform duty cycle at a particular intensity to the electrocautery end effector of the electrosurgical instrument.

The voltage divider network may generate a first characteristic voltage which when measured by the electrosurgical generator causes the electrosurgical generator to transmit a waveform duty cycle which produces a cutting effect; a second characteristic voltage which when measured by the electrosurgical generator causes the electrosurgical generator to transmit a waveform duty cycle which produces a division with hemostatic effect; and a third characteristic voltage which when measured by the electrosurgical generator causes the electrosurgical generator to transmit a waveform duty cycle which produces a coagulating effect.

The voltage divider network may generate a series of characteristic voltages which when measured by the electrosurgical generator cause the electrosurgical generator to transmit the particular waveform duty cycle at a corresponding level of intensity.

The electrosurgical instrument may include a plurality of activation buttons supported on the housing, wherein each activation button is operatively associated with the voltage divider network.

It is envisioned that each activation button is actuatable to cause the voltage divider network to generate a respective one of the characteristic voltages for transmission of a corresponding waveform duty cycle.

The electrosurgical instrument may include an intensity controller supported in the housing, wherein the intensity controller is operatively associated with the voltage divider network. The intensity controller may be actuatable to cause the voltage divider network to generate a respective one of the series of characteristic voltages for transmission of the waveform duty cycle at a corresponding intensity level. The intensity controller may be slidably supported in the housing of the electrosurgical instrument.

It is envisioned that the division with hemostatic effect has a waveform with a duty cycle of from about 12% to about 75%; that the coagulation effect has a waveform with a duty cycle of from about 1% to about 12%; and that the cutting effect has a waveform with a duty cycle of from about 75% to about 100%.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

FIG. 10 is a perspective view of the electrosurgical pencil of FIGS. 1-9, illustrating actuation of the intensity controller;

FIG. 11 is a top plan view of the electrosurgical pencil of FIGS. 1-10, with the top-half shell of the housing removed;

FIG. 14 is a side elevational view of the longitudinal cross-section of the electrosurgical pencil of FIG. 12;

FIG. 15 is an enlarged view of the indicated area of detail of FIG. 14;

FIG. 17 is a perspective view of the plug assembly of FIG. 16, with a top-half shell section removed therefrom;

FIG. 18 is an enlarged perspective view of the indicated area of detail of FIG. 17;

FIG. 19 is a top plan view of the plug assembly of FIGS. 17 and 18;

FIG. 20 is an enlarged view of the indicated area of detail of FIG. 19;

FIG. 29 is a top plan view of an electrosurgical pencil according to one embodiment of the present disclosure;

FIG. 30 is a side elevational view of the electrosurgical pencil of FIG. 29;

FIG. 31 is a top plan view of an electrosurgical pencil according to yet another embodiment of the present disclosure;

FIG. 32 is a side elevational view of the electrosurgical pencil of FIG. 31;

FIG. 33 is a top plan view of an electrosurgical pencil according to still another embodiment of the present disclosure;

FIG. 34 is a side elevational view of the electrosurgical pencil of FIG. 33;

FIG. 39 is a top plan view of the electrosurgical pencil of FIG. 38;

FIG. 40 is a side elevational view of the electrosurgical pencil of FIGS. 38 and 39;

FIG. 43 is a longitudinal, cross-sectional, side elevational view of the electrosurgical pencil of FIGS. 38-42;

FIG. 44 is an enlarged view of the indicated area of detail of FIG. 43;

DETAILED DESCRIPTION

Figure 1:
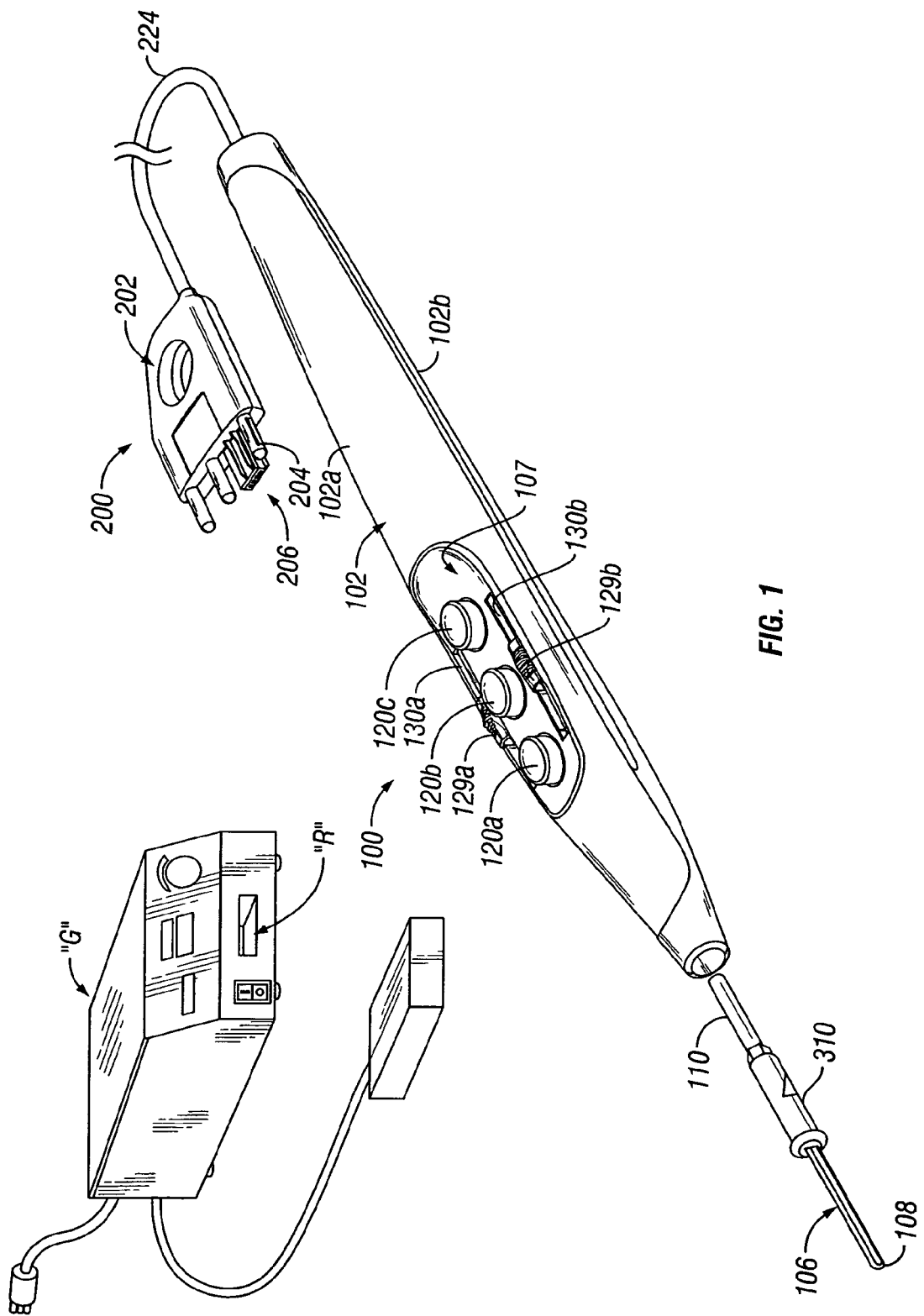
FIG. 1 is a perspective view of an electrosurgical system including an electrosurgical pencil in accordance with an embodiment of the present disclosure.
Figure 2:
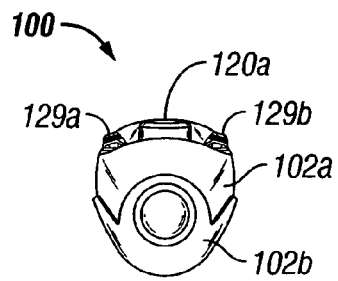
FIG. 2 is front elevational view of the electrosurgical pencil of FIG. 1.
Figure 3:
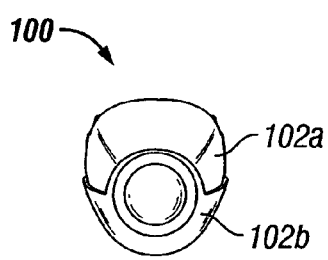
FIG. 3 is a rear elevational view of the electrosurgical pencil of FIGS. 1 and 2.
Figure 4:
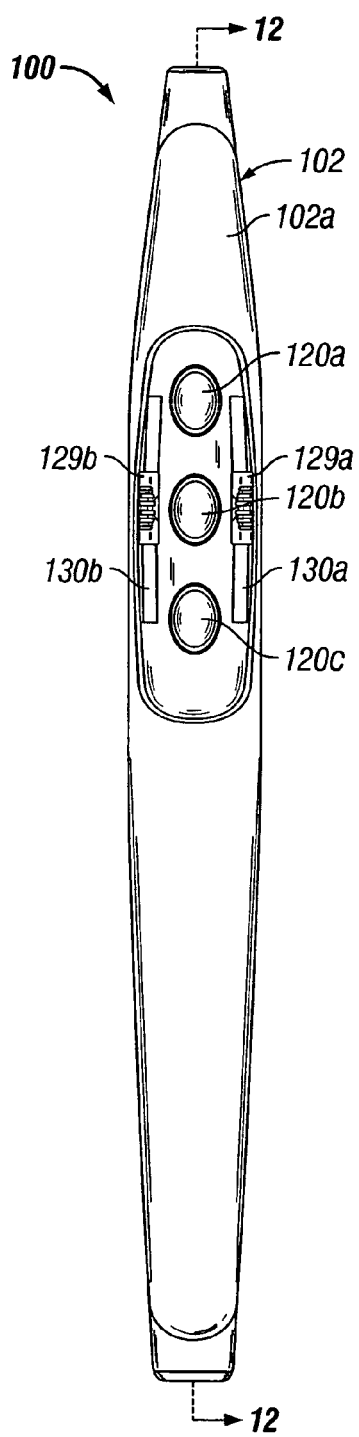
FIG. 4 is a top plan view of the electrosurgical pencil of FIGS. 1-3.
Figure 5:
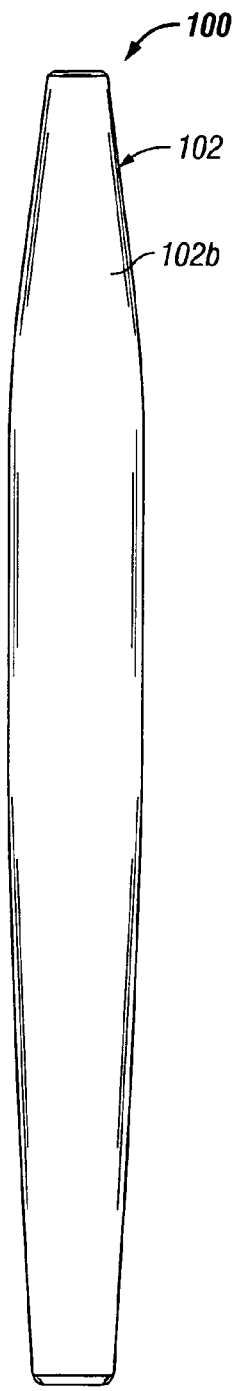
FIG. 5 is a bottom plan view of the electrosurgical pencil of FIGS. 1-4.
Figure 6:
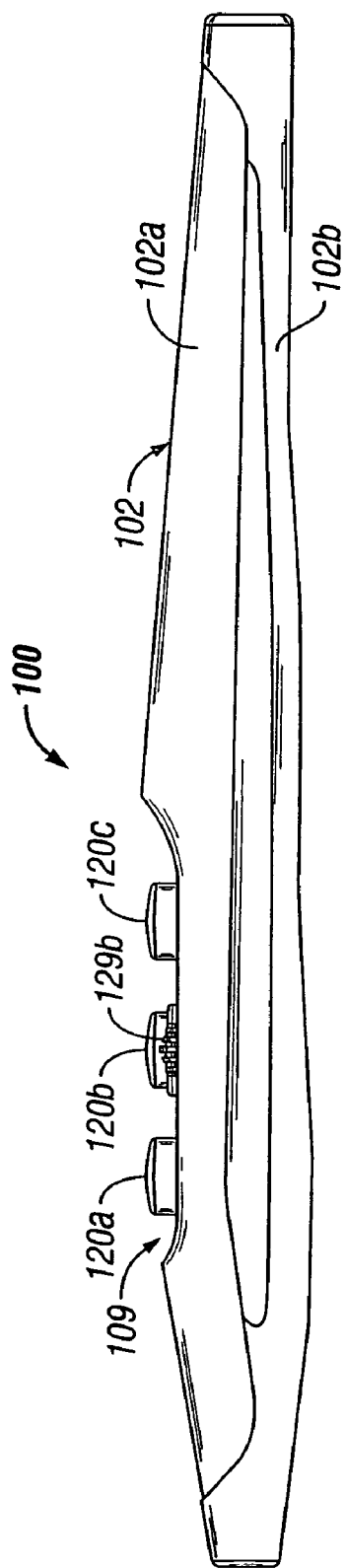
FIG. 6 is a left side elevational view of the electrosurgical pencil of FIGS. 1-5.
Figure 7:
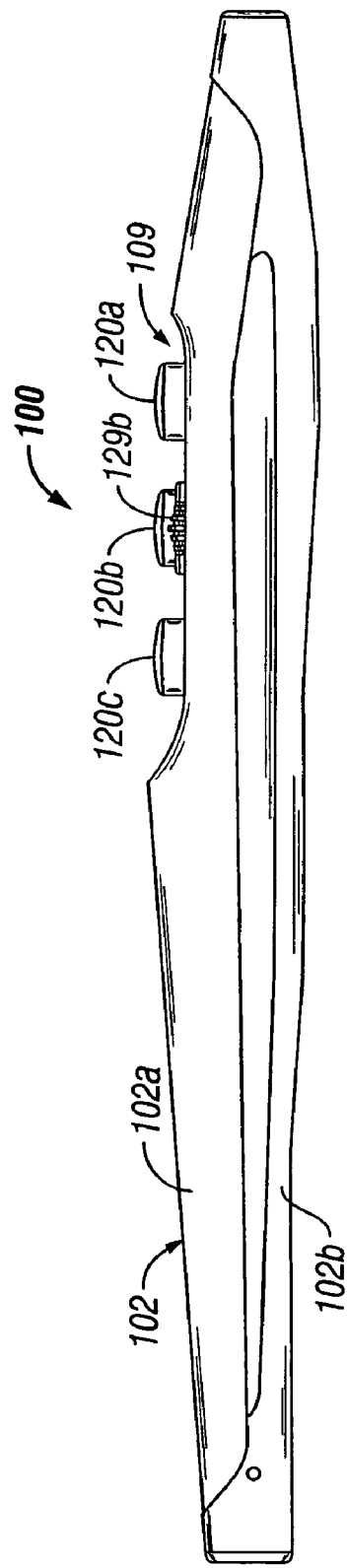
FIG. 7 is a right side elevational view of the electrosurgical pencil of FIGS. 1-6.

Preferred embodiments of the presently disclosed electrosurgical pencil will now be described in detail with reference to the drawing figures wherein like reference numerals identify similar or identical elements. As used herein, the term "distal" refers to that portion which is further from the user while the term "proximal" refers to that portion which is closer to the user or surgeon.

FIG. 1 sets forth a perspective view of an electrosurgical system including an electrosurgical pencil 100 constructed in accordance with one embodiment of the present disclosure. While the following description will be directed towards electrosurgical pencils it is envisioned that the features and concepts (or portions thereof) of the present disclosure can be applied to any electrosurgical type instrument, e.g., forceps, suction coagulators, vessel sealers, wands, etc.

Figure 8:
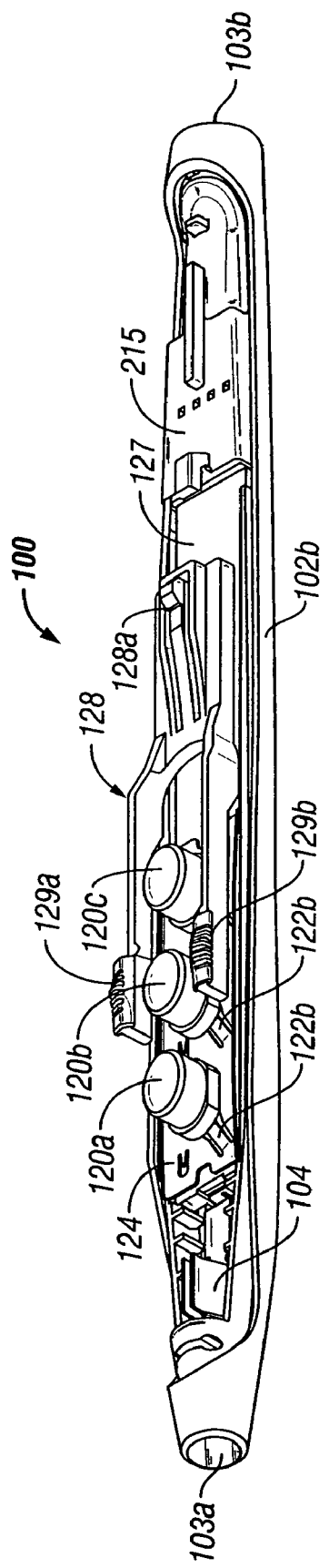
FIG. 8 is a front, top perspective view of the electrosurgical pencil of FIGS. 1-7, with a top-half shell of the housing removed.
Figure 9:
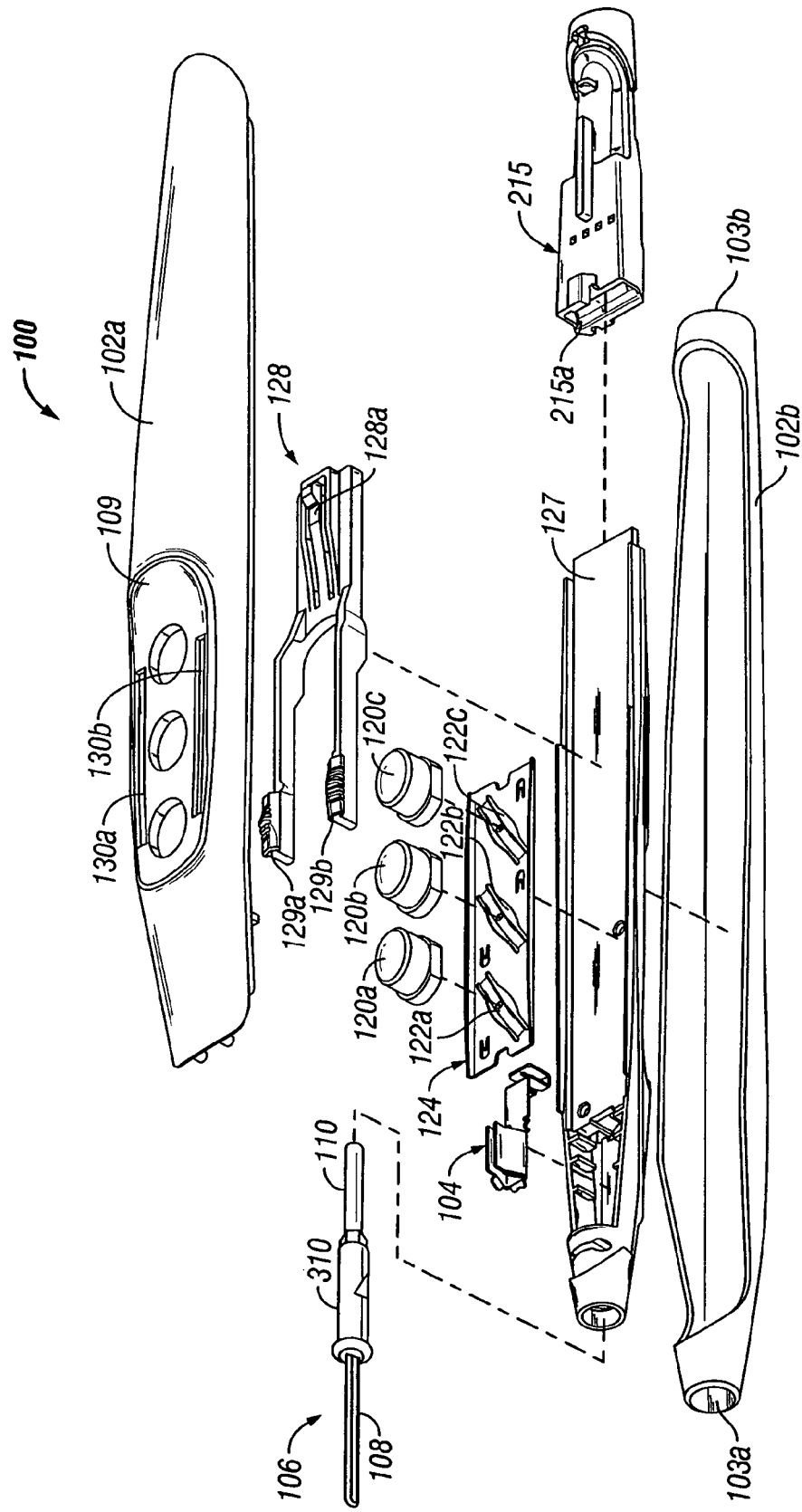
FIG. 9 is an exploded perspective view of the electrosurgical pencil of FIGS. 1-8.

As seen in FIGS. 1-7, electrosurgical pencil 100 includes an elongated housing 102 having a top-half shell portion 102a and a bottom-half shell portion 102b. Desirably, housing 102 is not divided along a longitudinal center line. As seen in FIGS. 8 and 9, bottom-half shell portion 102b includes a distal opening 103a, through which a blade 106 extends, and a proximal opening 103b, through which connecting wire 224 (see FIG. 1) extends. Desirably, top-half shell portion 102a and bottom-half shell portion 102b may be bonded together using methods known by those skilled in the art, e.g., sonic energy, adhesives, snap-fit assemblies, etc.

Electrosurgical pencil 100 further includes a blade receptacle 104 disposed at a distal end of housing 102, and a replaceable electrocautery end effector 106 operatively and removably connectable to blade receptacle 104. Electrocautery end effector 106 may be in the form of a needle, loop, blade and/or wand. A distal end portion 108 of blade 106 extends distally beyond receptacle 104 while a proximal end portion 110 of blade 106 is selectively retained by receptacle 104 within the distal end of housing 102. It is contemplated that electrocautery blade 106 is fabricated from a conductive type material, such as, for example, stainless steel, or is coated with an electrically conductive material. Blade receptacle 104 is desirable fabricated from an electrically conductive material. Blade receptacle 104 is electrically connected to voltage divider network 127 (FIGS. 8, 9 and 25) as explained in more detail below.

Desirably, as seen in FIG. 1, electrosurgical pencil 100 may be coupled to a conventional electrosurgical generator "G" via a plug assembly 200 (see FIGS. 16-21), as will be described in greater detail below.

For the purposes herein, the terms "switch" or "switches" includes electrical actuators, mechanical actuators, electromechanical actuators (rotatable actuators, pivotable actuators, toggle-like actuators, buttons, etc.) or optical actuators.

With reference to FIGS. 1-7 and 9, electrosurgical pencil 100 includes at least one activation switch, preferably three activation switches 120a-120c, each of which extends through top-half shell portion 102a of housing 102. Each activation switch 120a-120c is operatively supported on a respective tactile element 122a-122c (here shown as a snap-dome switch) provided on a switch plate 124. Each activation switch 120a-120c controls the transmission of RF electrical energy supplied from generator "G" to electrosurgical blade 106. More particularly, switch plate 124 is positioned on top of a voltage divider network 127 (hereinafter "VDN 127") such that tactile elements 122a-122c are operatively associated therewith. Desirably, VDN 127 (e.g., here shown as a film-type potentiometer) forms a switch closure. For the purposes herein, the term "voltage divider network" relates to any known form of resistive, capacitive or inductive switch closure (or the like) which determines the output voltage across a voltage source (e.g., one of two impedances) connected in series. A "voltage divider" as used herein relates to a number of resistors connected in series which are provided with taps at certain points to make available a fixed or variable fraction of the applied voltage.

In use, depending on which activation switch 120a-120c is depressed a respective tactile element 122a-122c is pressed into contact with VDN 127 and a characteristic signal is transmitted to electrosurgical generator "G" via control wires or electrical wires 216 (see FIGS. 17-20). Desirably, three control wires 216a-216c (one for each activation switch 120a-120c, respectively) are provided. Control wires 216a-216c are preferably electrically connected to switches 120a-120c via a controller terminal 215 (see FIGS. 9, 11, 12, 14, 21 and 22) which is operatively connected to VDN 127. By way of example only, electrosurgical generator "G" may be used in conjunction with the device wherein generator "G" includes a circuit for interpreting and responding to the VDN settings.

Activation switches 120a-120c are configured and adapted to control the mode and/or "waveform duty cycle" to achieve a desired surgical intent. For example, first activation switch 120a can be set to deliver a characteristic signal to electrosurgical generator "G" which in turn transmits a duty cycle and/or waveform shape which produces a cutting and/or dissecting effect/function. Meanwhile, second activation switch 120b can be set to deliver a characteristic signal to electrosurgical generator "G" which in turn transmits a duty cycle and/or waveform shape which produces a division or dividing with hemostatic effect/function. Finally, third activation switch 120c can be set to deliver a characteristic signal to electrosurgical generator "G" which in turn transmits a duty cycle and/or waveform shape which produces a hemostatic effect/function.

As seen in FIGS. 17-20, a fourth wire or RF line 216d for transmitting RF energy to electrocautery blade 106 is preferably provided and is directly electrically connected to blade receptacle 104 for connection to proximal end 110 of electrocautery blade 106. Since RF line 216d is directly connected to blade receptacle 104, RF line 216d bypasses VDN 127 and is isolated from VDN 127 and control wires 216a-216c. By directly connecting RF line 216d to blade receptacle 104 and isolating VDN 127 from the RF energy transmission, the electrosurgical current does not flow through VDN 127. This in turn, increases the longevity and life of VDN 127 and/or switches 120a-120c.

As such, a VDN 127 and/or switches 120a-120c may be selected which are less complex and/or which are relatively inexpensive since the switch does not have to transmit current during activation. For example, if return control wire 216d is provided, switches 120a-120c may be constructed by printing conductive ink on a plastic film. On the other hand, if a return control wire 216d is not provided, switches may be of the type made of standard stamped metal which add to the overall complexity and cost of the instrument.

Figure 25:
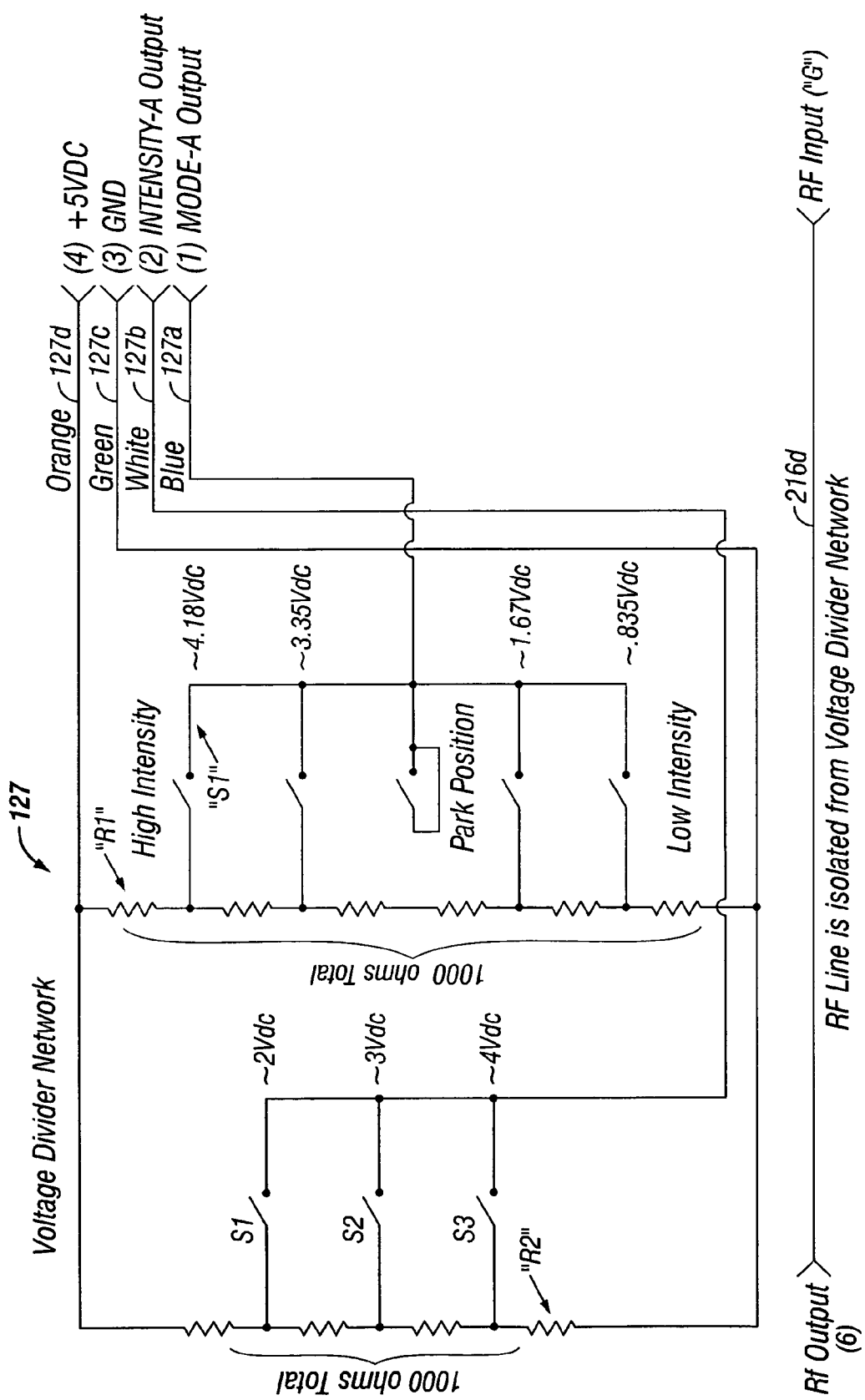
FIG. 25 is a schematic illustration of the voltage divider network of the present disclosure.

With reference to FIG. 25, in accordance with an embodiment of the present disclosure, a voltage divider network (VDN) 127 is shown. VDN 127 includes a first transmission line 127a to operate the various modes of electrosurgical pencil 100; a second transmission line 127b to operate the various intensities of electrosurgical pencil 100; a third transmission line 127*c* to function as a ground for VDN 127; and a fourth transmission line 127*d* which may transmit up to about +5 volts to VDN 127.

As seen in FIG. 25, RF line 216*d* is isolated from or otherwise completely separate from VDN 127. In particular, RF line 216*d* extends directly from the RF input or generator "G" to the RF output or to electrocautery blade 106.

By way of example only, VDN 127 may include a plurality of resistors "R1" (e.g., six (6) resistors), connected in a first series between first transmission line 127*c* and fourth transmission line 127*d*. The first series of resistors "R1" may combine to total about 1000 ohms of resistance. The first series of resistors "R1" are substantially each separated by a first set of switches "S1". Each switch of the first set of switches "S1" may be electrically connected between adjacent resistors "R1" and first transmission line 127*a* of VDN 127. In operation, depending on which switch or switches of the first set of switches "S1" is/are closed, a different mode of operation for electrosurgical pencil 100 is activated.

Additionally, by way of example only, VDN 127 may include a plurality of resistors "R2" (e.g., four (4) resistors), connected in a second series between first transmission line 127*c* and fourth transmission line 127*d*. The second series of resistors "R2" may combine to total about 1000 ohms of resistance. The second series of resistors "R2" are each separated by a second set of switches "S2". Each switch of the second set of switches "S2" may be electrically connected between adjacent resistors "R2" and second transmission line 127*b* of VDN 127. In operation, depending on which switch or switches of the second set of switches "S2" is/are closed, a different intensity of RF energy is transmitted by electrosurgical pencil 100.

The dividing with hemostatic effect/function can be defined as having waveforms with a duty cycle from about 12% to about 75%. The hemostatic/coagulation effect/function can be defined as having waveforms with a duty cycle from about 1% to about 12%. The cutting and/or dissecting effect/function can be defined as having waveforms with a duty cycle from about 75% to about 100%. It is important to note that these percentages are approximated and may be customized to deliver the desired surgical effect for various tissue types and characteristics.

Figure 25A:
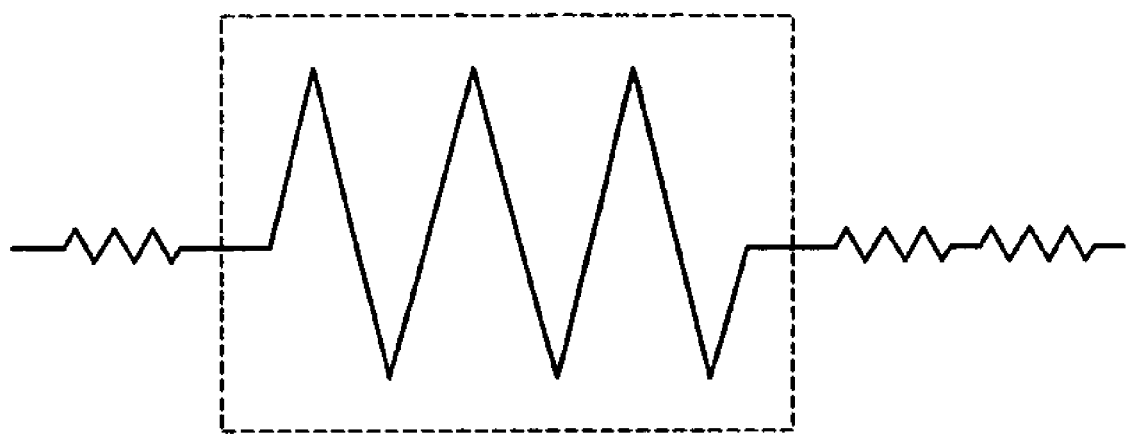
FIG. 25A is a schematic illustration of the exemplary waveform transmitted by the electrosurgical pencil of the present disclosure when a dividing with hemostatic effect/function is activated.

In accordance with the present disclosure and as seen in FIG. 25A, the dividing with hemostatic effect/function is transmitted and/or delivered in discrete energy packets. The discrete energy packets include an amplification or ramp-up period and a degradation or ramp-down period which is reduced and/or eliminated. In other words, the discrete energy packets delivered during the transmission of the dividing with hemostatic effect/function include an almost instantaneous amplification of energy and an almost instantaneous degradation of energy. Additionally, the dividing and hemostasis effect/function has a waveform with a duty cycle of approximately 24%. The activation switch 120*b* controlling the dividing and hemostatic effect/function operates as a closed loop control.

As seen throughout FIGS. 1-15, electrosurgical pencil 100 further includes an intensity controller 128 slidingly supported on or in housing 102. Intensity controller 128 includes a pair of nubs 129*a*, 129*b* which are slidingly supported, one each, in respective guide channels 130*a*, 130*b*, formed in top-half shell portion 102*a* of housing 102. Desirably, guide channels 130*a*, 130*b* are formed on either side of activations switches 120*a*-120*c*. By providing nubs 129*a*, 129*b* on either side of activation switches 120*a*-120*c*, intensity controller 128 can be easily manipulated by either hand of the user or the same electrosurgical pencil can be operated by a right-handed or a left-handed user.

Figure 21:
FIG. 21 is a top, front perspective view of a bottom-half portion of the electrosurgical pencil of FIGS. 1-14, illustrating the association of a controller portion of the plug assembly therewith.
Figure 22:
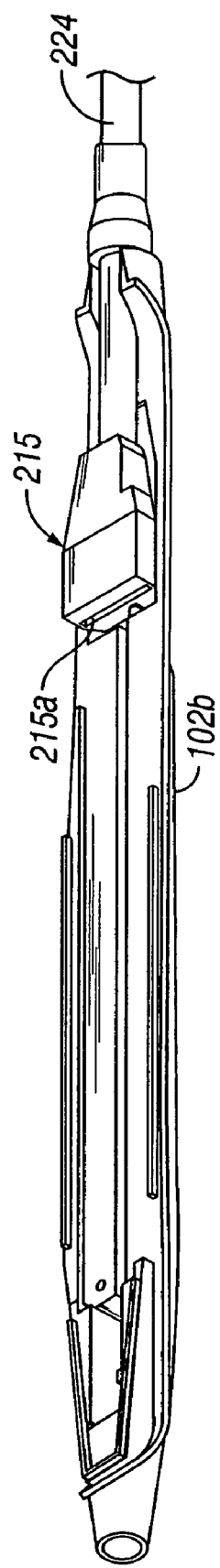
FIG. 22 is an enlarged view of FIG. 21.
Figure 23:
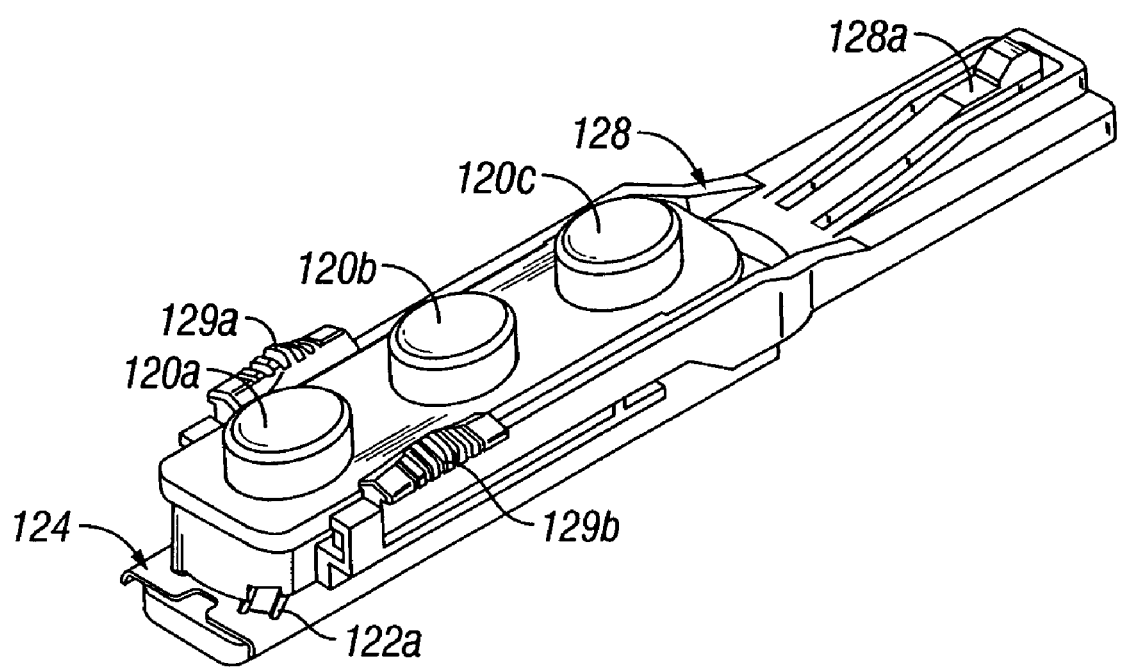
FIG. 23 is a perspective view of a controller unit of the electrosurgical pencil of FIGS. 1-14.
Figure 24:
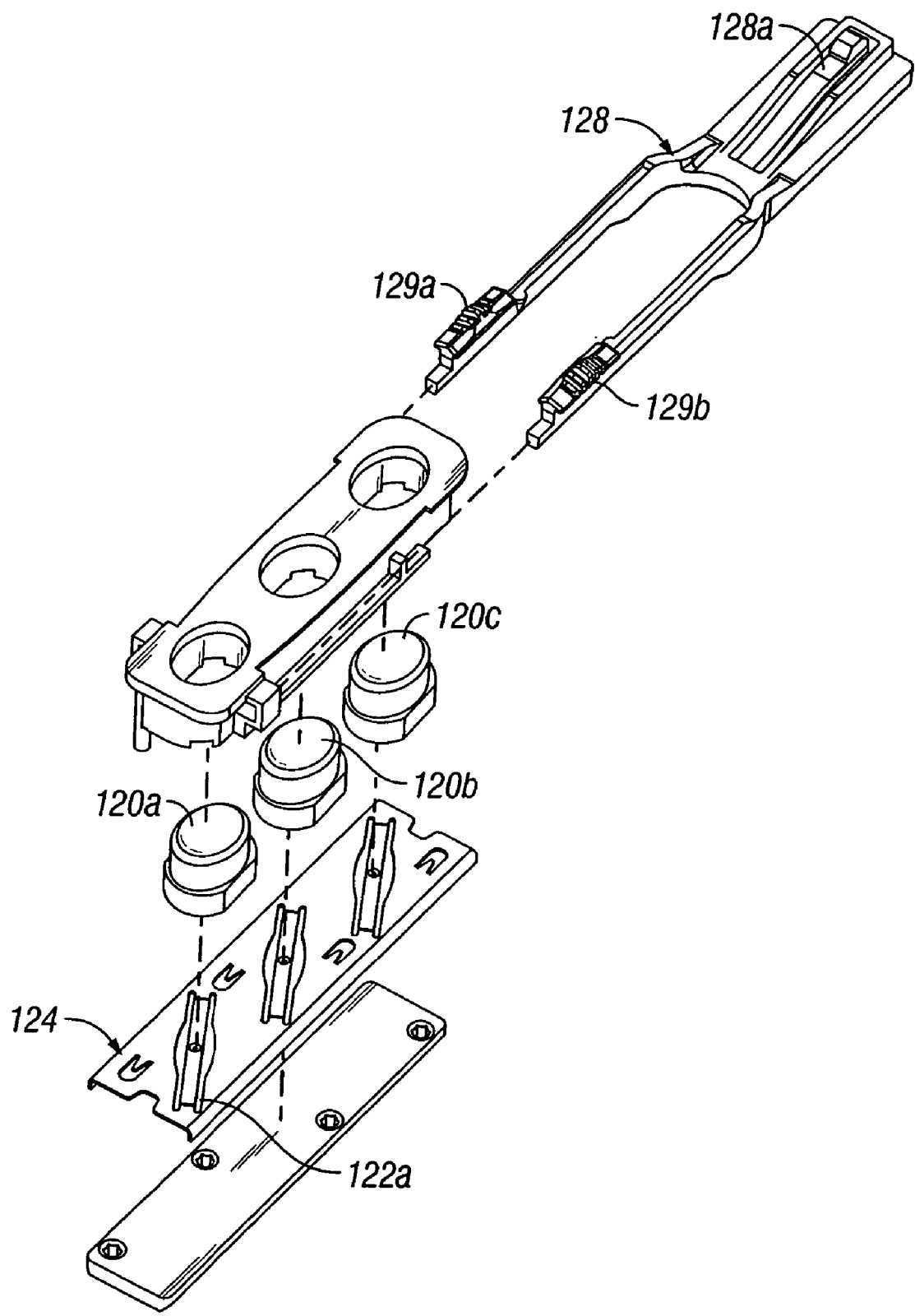
FIG. 24 is an exploded perspective view of the controller unit of FIG. 23.

As seen in FIGS. 21 and 14, intensity controller 128 further includes a nub 129*c* extending from a bottom surface thereof which contacts and presses into or against VDN 127. In this manner, as intensity controller 128 is displaced in a distal and proximal direction relative to housing 102, third nub 129*c* moves relative to VDN 127 to vary the intensity setting being transmitted to electrocautery end effector 106, as will be described in greater detail below.

Intensity controller 128 may be configured to function as a slide potentiometer, sliding over and along VDN 127. Intensity controller 128 has a first position wherein nubs 129*a*, 129*b* are at a proximal-most position (e.g., closest to plug assembly 200 and third nub 129*c* being located at a proximal-most position) corresponding to a relative low intensity setting, a second position wherein nubs 129*a*, 129*b* are at a distal-most position (e.g., closest to electrocautery end effector 106 and third nub 129*c* being located at a distal-most position) corresponding to a relative high intensity setting, and a plurality of intermediate positions wherein nubs 129*a*, 129*b* are at positions between the distal-most position and the proximal-most position corresponding to various intermediate intensity settings. As can be appreciated, the intensity settings from the proximal end to the distal end may be reversed, e.g., high to low.

Figures 12, 13:
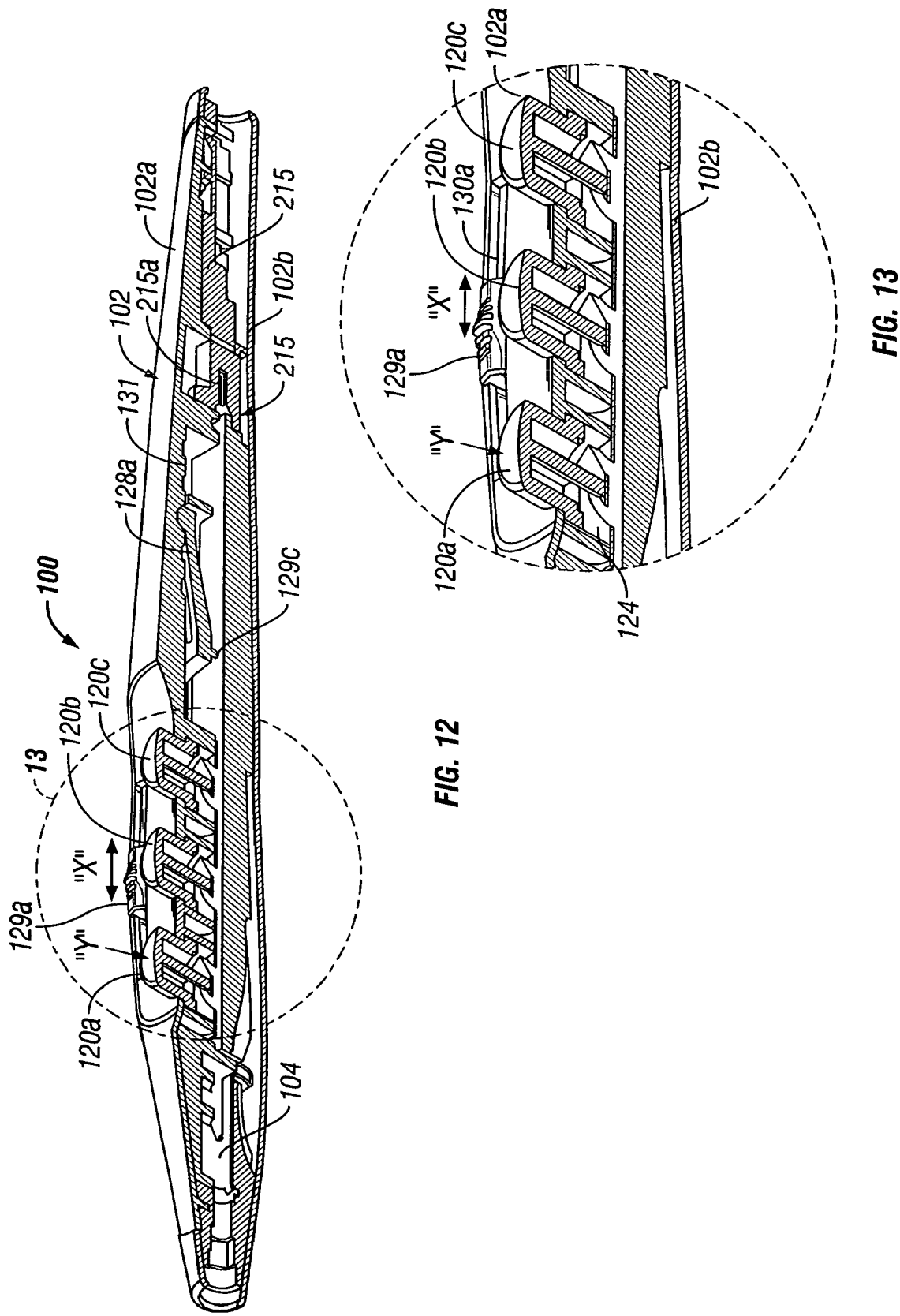
FIG. 12 is a longitudinal cross-sectional view, as taken through 12-12 of FIG. 4.
FIG. 13 is an enlarged view of the indicated area of detail of FIG. 12.
Figure 16:
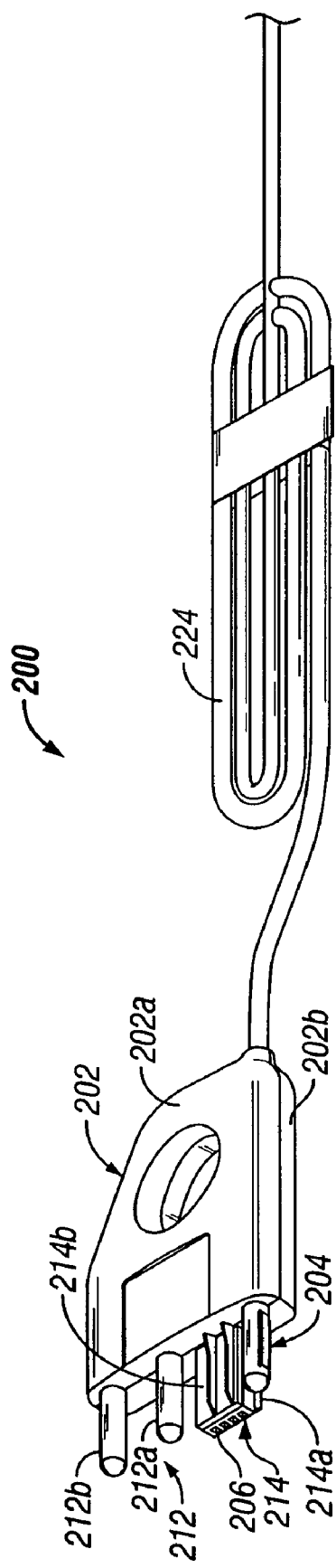
FIG. 16 is a perspective view of a plug assembly for use with the electrosurgical pencil of FIGS. 1-14.

It is contemplated that nubs 129*a*, 129*b* of intensity controller 128 and corresponding guide channels 130*a*, 130*b* may be provided with a series of cooperating discreet or detented positions defining a series of positions, e.g., five, to allow easy selection of the output intensity from the low intensity setting to the high intensity setting. The series of cooperating discreet or detented positions also provide the surgeon with a degree of tactile feedback. By way of example only, as seen in FIGS. 12 and 14, a plurality of discreet detents 131 are defined in an inner upper surface of top-half shell portion 102*a* for cooperating with and selectively engaging a resilient finger 128*a* extending upwardly from intensity controller 128. Accordingly, in use, as intensity controller 128 slides distally and proximally, resilient finger 128*a* selectively engages detents 131 to set the intensity level as well as to provide the user with tactile feedback as to when the intensity controller has been set to the desired intensity setting.

Intensity controller 128 is configured and adapted to adjust the power parameters (e.g., voltage, power and/or current intensity) and/or the power verses impedance curve shape to affect the perceived output intensity. For example, the greater intensity controller 128 is displaced in a distal direction the greater the level of the power parameters transmitted to electrocautery blade 106. Conceivably, current intensities can range from about 60 mA to about 240 mA when using an electrosurgical blade and having a typical tissue impedance of about 2K ohms. An intensity level of 60 mA provides very light and/or minimal cutting/dissecting/hemostatic effects. An intensity level of 240 mA provides very aggressive cutting/dissecting/hemostatic effects. Accordingly, the preferred range of current intensity is from about 100 mA to about 200 mA at 2K ohms.

The intensity settings are preferably preset and selected from a look-up table based on a choice of electrosurgical instruments/attachments, desired surgical effect, surgical specialty and/or surgeon preference. The selection may be made automatically or selected manually by the user. The intensity values may be predetermined or adjusted by the user.

In operation, and depending on the particular electrosurgical function desired, the surgeon depresses one of activation switches 120a-120c, in the direction indicated by arrow "Y" (see FIGS. 12-15) thereby urging a corresponding tactile element 122a-122c against VDN 127 and thereby transmitting a respective characteristic signal to electrosurgical generator "G". For example, the surgeon can depress activation switch 120a to perform a cutting and/or dissecting function, activation switch 120b to perform a blending function, or activation switch 120c to perform a hemostatic function. In turn, generator "G" transmits an appropriate waveform output to electrocautery blade 106 via RF line 216d.

In order to vary the intensity of the power parameters of electrosurgical pencil 100, the surgeon displaces intensity controller 128, by manipulating at least one of nubs 129a, 129b, in the direction indicated by double-headed arrow "X" (see FIGS. 12 and 13). As mentioned above, the intensity can be varied from approximately 60 mA for a light effect to approximately 240 mA for a more aggressive effect. For example, by positioning nubs 129a, 129b of intensity controller 128 closer to the proximal-most end of guide channels 130a, 130b (i.e., closer to plug assembly 200) a lower intensity level is produced, and by positioning nubs 129a, 129b of intensity controller 128 closer to the distal-most end of guide channels 130a, 130b (i.e., closer to electrocautery end effector 106) a larger intensity level is produced. It is envisioned that when nubs 129a, 129b of intensity controller 128 are positioned at the proximal-most end of guide channels 130a, 130b, VDN 127 is set to a null and/or open position. Electrosurgical pencil 100 may be shipped with intensity controller 128 set to the null and/or open position.

Intensity controller 128 controls the intensity level of the electrosurgical energy activated by all three activation switches 120a-120c, simultaneously. In other words, as nubs 129a, 129b of intensity controller 128 are positioned relative to guide channels 130a, 130b, the intensity level of the electrosurgical energy transmitted to each activation switch 120a-120c is set to the same value of intensity controller 128.

As a safety precaution, it is envisioned that when electrosurgical pencil 100 is changed from one mode to another, intensity controller 128 may be configured such that it must be reset (i.e., nubs 129a, 129b, re-positioned to the proximal-most end of guide channels 130a, 130b thus setting VDN 127 to the null and/or open position). After being reset, intensity controller 128 may be adjusted as needed to the desired and/or necessary intensity level for the mode selected.

It is envisioned and contemplated that VDN 127 may also include an algorithm which stores the last intensity level setting for each mode. In this manner, intensity controller 128 does not have to be reset to the last operative value when the particular mode is re-selected.

The combination of placing VDN 127 and RF line 216d in electrosurgical pencil 100 essentially places the entire resistor network of the electrosurgical system (e.g., electrosurgical pencil 100 and the source of electrosurgical energy "G") within electrosurgical pencil 100. Conventional electrosurgical systems typically include a current limiting resistor disposed within the electrosurgical pencil, for activating the electrosurgical pencil, and a second resistor network disposed in the source of electrosurgical energy, for controlling the intensity of the electrosurgical energy transmitted. In accordance with the present disclosure, both the first and the second resistor networks are disposed within electrosurgical pencil 100, namely, the first resistor network as evidenced by activation switches 120a-120c, and the second resistor network as evidenced by intensity controller 128.

As described above, intensity controller 128 can be configured and adapted to provide a degree of tactile feedback by the inter-engagement of resilient finger 128a of intensity controller 128 in detents 131 formed in top-half shell portion 102a. Alternatively, audible feedback can be produced from intensity controller 128 (e.g., a "click"), from electrosurgical energy source "G" (e.g., a "tone") and/or from an auxiliary sound-producing device such as a buzzer (not shown).

As seen throughout FIGS. 1-15, nubs 129a, 129b of intensity controller 128 and activation switches 120a-120c are positioned in a depression 109 formed in top-half shell portion 102a of housing 102. Desirably, activation switches 120a-120c are positioned at a location where the fingers of the surgeon would normally rest when electrosurgical pencil 100 is held in the hand of the surgeon while nubs 129a, 129b of intensity controller 128 are placed at locations which would not be confused with activation switches 120a-120c. Alternatively, nubs 129a, 129b of intensity controller 128 are positioned at locations where the fingers of the surgeon would normally rest when electrosurgical pencil 100 is held in the hand of the surgeon while activation switches 120a-120c are placed at locations which would not be confused with nubs 129a, 129b of intensity controller 128. In addition, depression 109 formed in top-half shell portion 102a of housing 102 advantageously minimizes inadvertent activation (e.g., depressing, sliding and/or manipulating) of activation switches 120a-120c and intensity controller 128 while in the surgical field and/or during the surgical procedure.

As best seen in FIG. 10, housing 102 can include a series of indicia 31 provided thereon which are visible to the user. Indicia 31 may be a series of numbers (e.g., numbers 1-5) which reflect the level of intensity that is to be transmitted. Desirably, indicia 31 are provided alongside guide channels 130a, 130b. Indicia 31 are preferably provided on housing 102 and spaced therealong to correspond substantially with detents 131 of the tactile feedback. Accordingly, as intensity controller 128 is moved distally and proximally, nubs 129a, 129b are moved along guide channels 130a, 130b and come into registration with particular indicia 31 which correspond to the location of detents 131 of the tactile feedback. For example, indicia 31 may include numeric characters, as shown in FIG. 10, alphabetic character, alphanumeric characters, graduated symbols, graduated shapes, and the like.

As seen in FIGS. 1-15, housing 102 of electrosurgical pencil 100 is molded/contoured to improve the handling of electrosurgical pencil 100 by the surgeon. Desirably, the contouring reduces the pressure and gripping force required to use and/or operate electrosurgical pencil 100 thereby potentially reducing the fatigue experienced by the surgeon and to prevent movement of electrosurgical pencil 100 during proximal and distal adjustments of nubs 129a and 129b.

Turning now to FIGS. 16-22, a detailed discussion of plug assembly 200 is provided. As seen in FIGS. 16-22, plug assembly 200 includes a housing portion 202, a controller terminal 215, and a connecting wire 224 electrically interconnecting housing portion 202 and control terminal 215.

As seen in FIGS. 16-20, housing portion 202 includes a first half-section 202a and a second half-section 202b operatively engageable with one another, e.g., via a snap-fit engagement. Half-sections 202a, 202b are configured and adapted to retain a common power pin 204 and a plurality of electrical contacts 206 therebetween, as will be described in greater detail below.

Desirably, power pin 204 of plug assembly 200 extends distally from housing portion 202 at a location preferably between first half-section 202a and second half-section 202b. Power pin 204 may be positioned to be off center, i.e., closer to one side edge of housing portion 202 than the other. Plug assembly 200 further includes at least one, desirably, a pair of position pins 212 also extending from housing portion 202. Position pins 212 may be positioned between half-sections 202a and 202b of housing portion 202 and are oriented in the same direction as power pin 204. Desirably, a first position pin 212a is positioned in close proximity to a center of housing portion 202 and a second position pin 212b is positioned to be off center and in close proximity to an opposite side edge of housing portion 202 as compared to power pin 204. Pins 212a, 212b and 204 may be located on housing portion 202 at locations which correspond to pin receiving positions (not shown) of a connector receptacle "R" of electrosurgical generator "G" (see FIG. 1).

Plug assembly 200 further includes a prong 214 extending from housing portion 202. In particular, prong 214 includes a body portion 214a (see FIGS. 17 and 18) extending from second half-section 202b of housing portion 202 and a cover portion 214b extending from first half-section 202a of housing portion 202. In this manner, when half-sections 202a, 202b are joined to one another, cover portion 214b of prong 214 encloses body portion 214a. Prong 214 may be positioned between power pin 204 and first position pin 212a. Prong 214 is configured and adapted to retain electrical contacts 206 therein such that a portion of each contact 206 is exposed along a front or distal edge thereof. While four contacts 206 are shown, it is envisioned that any number of contacts 206 can be provided, including and not limited to two, six and eight. Prong 214 may be located on housing portion 202 at a location which corresponds to a prong receiving position (not shown) of connector receptacle "R" of electrosurgical generator "G" (see FIG. 1).

Since prong 214 extends from second half-section 202b of housing portion 202, housing portion 202 of plug assembly 200 will not enter connector receptacle "R" of electrosurgical generator "G" unless housing portion 202 is in a proper orientation. In other words, prong 214 functions as a polarization member. This ensures that power pin 204 is properly received in connector receptacle "R" of electrosurgical generator "G".

With continued reference to FIGS. 17-20, connecting wire 224 includes a power supplying wire 220 electrically connected to power pin 204, control wires 216a-216c electrically connected to a respective contact 206, and RF line 216d electrically connected to a respective contact 206.

Turning now to FIGS. 8, 9, 11, 12, 15, 21 and 22, control terminal 215 is supported in housing 202 near a proximal end thereof. Control terminal 215 includes a slot 215a formed therein for electrically receiving and connecting with VDN 127.

Figure 26:
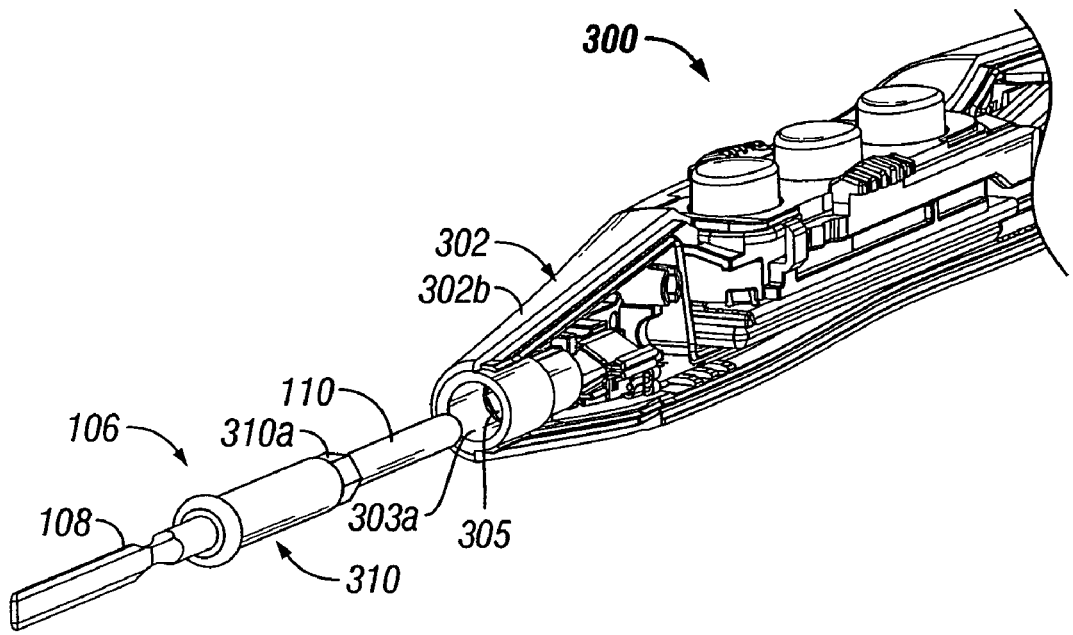
FIG. 26 is a partial, longitudinal, cross-sectional, front perspective view of a distal end of an electrosurgical pencil, in accordance with another embodiment of the present disclosure.

Turning now to FIG. 26, an electrosurgical pencil, according to another embodiment of the present disclosure, is shown generally as 300. Electrosurgical pencil 300 is substantially similar to electrosurgical pencil 100 and will only be discussed in detail to the extent necessary to identify differences in construction and operation.

Electrosurgical pencil 300 includes a housing 302 defining an open distal end 303a for selectively receiving proximal end 110 of electrocautery blade 106 therein. Open distal end 303a defines a non-circular inner profile 305, such as, for example, ovular, triangular, rectangular, hexagonal (as seen in FIG. 26), toothed, multi-faceted and the like.

Desirably, electrocautery blade 106 is supported in a collar 310. Collar 310 is desirably positioned between distal end 108 and proximal end 110 of electrocautery blade 106. Collar 310 has a shaped outer surface 310a configured and dimensioned to complement the inner profile 305 of open distal end 303a. In one embodiment, the open distal end 303a of housing 302 defines a hexagonal inner profile 305 and collar 310 defines a hexagonal outer surface 310a.

The shaped inner profile 305 of open distal end 303a of housing 302 may be formed using plastic injection molding, insert molding and/or broaching techniques. Desirably, open distal end 303a of housing 302 is completely formed in the bottom-half shell section 302b. By completely forming open distal end 303a in the bottom-half shell section 302b of housing 302, the tolerances, dimensions and shape of opening 303a and inner profile 305 are more consistent as compared to a housing whose top-half shell portion and bottom-half shell portion extend through the open distal end. Additionally, an open distal end 303a formed solely in bottom-half shell portion 302b is more centered, has less variability and increases the precision of fitting with mating geometry (i.e., shaped outer surface 310a of collar 310) as compared to a housing whose top-half shell portion and bottom-half shell portion extend through the open distal end.

Figure 27:
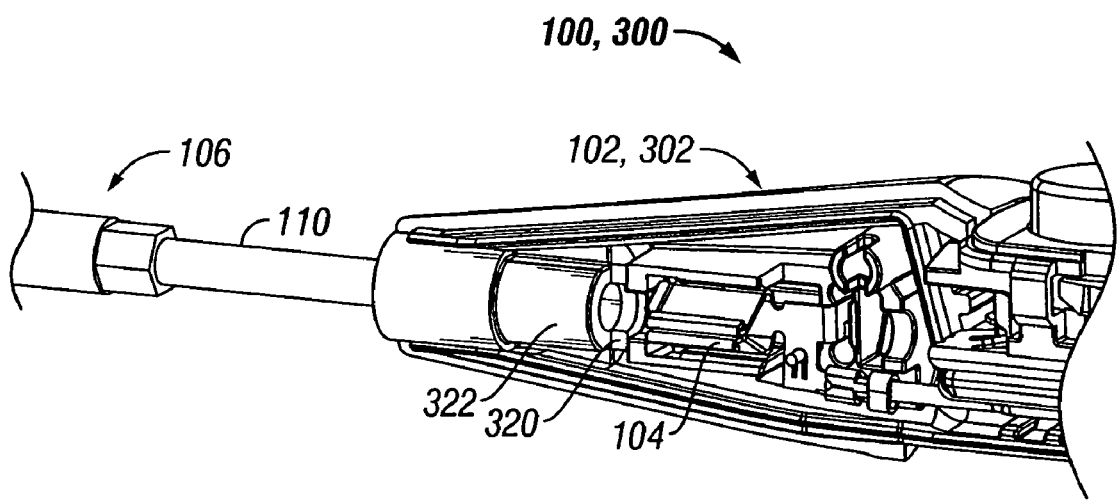
FIG. 27 is a partial, longitudinal, cross-sectional, side elevational view of a distal end of an electrosurgical pencil, in accordance with the embodiment of the FIG. 26 of the present disclosure.

Turning now to FIG. 27, an electrosurgical pencil substantially similar to electrosurgical pencils 100 and 300 is shown and will be discussed in detail to the extent necessary to identify difference in construction and operation therein. As seen in FIG. 27, electrosurgical pencil 100, 300 may include a stabilizer 320 disposed within its respective housing 102, 302 in order to take up any free-play in the connection of electrocautery blade 106 to housing 102, 302. Additionally, stabilizer 320 functions to improve the retention forces acting on proximal end 110 of electrocautery blade 106 which hold electrocautery blade 106 in position in housing 102, 302. Desirably, stabilizer 320 is positioned proximal of an electrocautery blade mount 322 provided near the distal end of housing 102, 302, and distal of blade receptacle 104.

Stabilizer 320 includes an opening or passage 321 formed therein through which proximal end 110 of electrocautery blade 106 passes when electrocautery blade 106 is connected to pencils 100 or 300. In use, with regard to electrosurgical pencil 300, as electrocautery blade 106 is connected to housing 302 of electrosurgical pencil 300, proximal end 110 is inserted into open distal end 303a of bottom-half shell portion 302b, through blade mount 322, through passage 321 of stabilizer 320, and into operative engagement with blade receptacle 104. Stabilizer 320 and, in particular, passage 321 of stabilizer 320 is configured and dimensioned to create an interference-type fit with proximal end 110 of electrocautery blade 106. As mentioned above, stabilizer 320 functions to at least take up any free-play in proximal end 110 of electrocautery blade 106 and to improve the retention forces associated with holding electrocautery blade 106 in place in housing 302 of electrosurgical pencil 300.

As seen in FIG. 27, passage 321 of stabilizer 320 is substantially circular. Desirably, passage 321 of stabilizer 320 has a dimension (i.e., a radius or diameter) which is less that a dimension (i.e., a radius or diameter) of proximal end 110 of electrocautery blade 106. While passage 321 of stabilizer 320 is shown as being circular, it is envisioned and within the scope of the present disclosure for passage 321 of stabilizer 320 to have any possible shape, such as, for example, and not limited to, a slit, star-shaped, cruciform-shaped, etc.

Stabilizer 320 is fabricated from a compliant polymeric material. Desirably, stabilizer 320 is fabricated from an insulative material. Stabilizer 320 is desirably fabricated from a material commercially available from Versaflex, Incorporated, Kansas City, Kans., and sold under the tradename Versaflex® 1245x-1.

Figure 28:
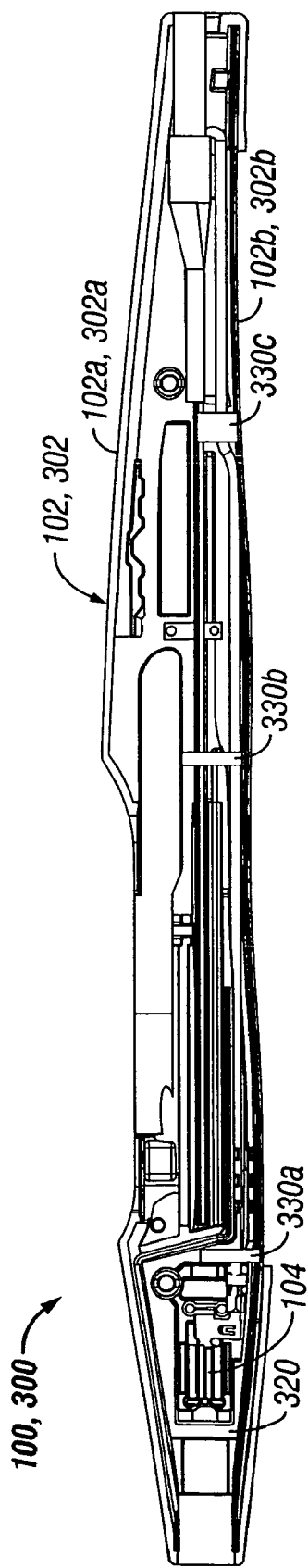
FIG. 28 is a longitudinal, cross-sectional, side elevational view of a distal end of an electrosurgical pencil, in accordance with another embodiment of the present disclosure.

Turning now to FIG. 28, an electrosurgical pencil substantially similar to electrosurgical pencils 100 and 300 is shown and will be discussed in detail to the extent necessary to identify difference in construction and operation therein. As seen in FIG. 28, electrosurgical pencil 100, 300 may include at least one, preferably, a plurality of runners 330 disposed within housing 120, 302 of electrosurgical pencil 100, 300 (three runners 330a-330c shown in FIG. 28). Desirably, a first runner 330a is positioned near a distal end of electrosurgical pencil 100, 300; a second runner 330b is positioned near an intermediate portion of electrosurgical pencil 100, 300; and a third runner 330c is positioned near a proximal end of electrosurgical pencil 100, 300.

Turning now to FIGS. 29 and 30, an embodiment of electrosurgical pencils 100 or 300 is shown. As seen in FIGS. 29 and 30, in particular in FIG. 30, desirably, indicia 31 is provided on housing 102, 302 of electrosurgical pencil 100 and/or 300 along at least one side thereof. Indicia 31 include a first or alphanumeric portion 31a, and a second, graphic or symbolic portion 31b. In the interest of economy, only one side of electrosurgical pencil 100, 300 is shown, the opposite side of electrosurgical pencil 100, 300 being a mirror image of the first side.

Desirably, as seen in FIG. 30, first indicium 31a includes numerals increasing from a proximal end of indicia 31 to a distal end of indicia 31. Also as seen in FIG. 30, second indicia 31b includes a series of symbols and/or shapes which increase in size from a proximal end of indicia 31 to a distal end of indicia 31. As described previously, as nubs 129a, 129b are moved in a distal direction, the intensity of the energy delivered to electrocautery blade 106 increases as evidenced by the increasing numbers of first indicia 31a and/or the increasing size of second indicia 31b. It follows that as nubs 129a, 129b are moved in a proximal direction, the intensity of the energy delivered to electrocautery blade 106 decreases as evidenced by the decreasing numbers of first indicia 31a and/or the decreasing size of indicia 31b.

As seen in FIG. 30, electrosurgical pencil 100, 300 further includes a further graphic or a grip enhancing feature 33 provided on each side thereof. Grip enhancing feature 33 includes an elongate tapering "swoosh" shape (i.e., a profile substantially similar to a cross-sectional profile of an aircraft wing) formed along the side of housing 102, 302. Desirably, grip enhancing feature 33 is a rubberized material, a texturized surface, or the like. In this manner, when electrosurgical pencil 100, 300 is held in the hand of the surgeon, the fingers of the surgeon contact and/or touch grip enhancing feature 33, thereby increasing the maneuverability and operation of electrosurgical pencil 100, 300.

Electrosurgical pencil 100, 300 may also include a soft-touch element 35 provided on housing 102, 302. As seen in FIG. 30, soft-touch element 35 is desirably provided near a proximal end of housing 102, 302, along a bottom surface thereof. In this manner, when electrosurgical pencil 100, 300 is held in the hand of the surgeon, the soft-touch element 35 comes to rest on the surgeons' hand thereby increasing the comfort and operation of electrosurgical pencil 100, 300.

Turning now to FIGS. 31 and 32, indicia 31 includes a first or alphanumeric portion 31a, and a second, graphic or symbolic portion 31b. In the interest of economy, only one side of electrosurgical pencil 100, 300 is shown, the opposite side of electrosurgical pencil 100, 300 being a mirror image of the first side. Desirably, second portion 31b of indicia 31 is in the shape of an elongate tapering "swoosh". It is envisioned that a relatively enlarged end of second portion 31b of indicia 31 is located proximate the largest alphanumeric value of first portion 31a of indicia 31, and a relatively thinner end of second portion 31b of indicia 31 extends beyond the smallest alphanumeric value of first portion 31a of indicia 31. It is contemplated that second portion 31b of indicia 31 is segmented or otherwise divided into discrete portions wherein each portion corresponds with an alphanumeric value of first portion 31a of indicia 31.

Turning now to FIGS. 33 and 34, indicia 31 include a first or alphanumeric portion 31a, and a second or symbolic portion 31b. In the interest of economy, only one side of electrosurgical pencil 100, 300 is shown, the opposite side of electrosurgical pencil 100, 300 being a mirror image of the first side. Desirably, second portion 31b of indicia 31 is in the shape of an elongate tapering "swoosh". It is envisioned that a relatively enlarged end of second portion 31b of indicia 31 is located distal of the largest alphanumeric value of first portion 31a of indicia 31, and a relatively thinner end of second portion 31b of indicia 31 extends beyond the smallest alphanumeric value of first portion 31a of indicia 31. It is contemplated that second portion 31b of indicia 31 includes notches and the like formed therein to demark segments of second portion 31b of indicia 31, wherein each segment corresponds with an alphanumeric value of first portion 31a of indicia 31.

As seen in FIG. 34, electrosurgical pencil 100 or 300 includes soft-touch element 35 extending along a bottom surface thereof. In this manner, when electrosurgical pencil 100, 300 is held in the hand of the surgeon, the soft-touch element 35 comes to rest on the surgeons' hand thereby increasing the comfort and operation of electrosurgical pencil 100, 300.

Desirably, second portion 31b of indicia 31 is fabricated from a soft-touch material or other material capable of enhancing the grip of electrosurgical instrument 100 or 300.

Figure 35:
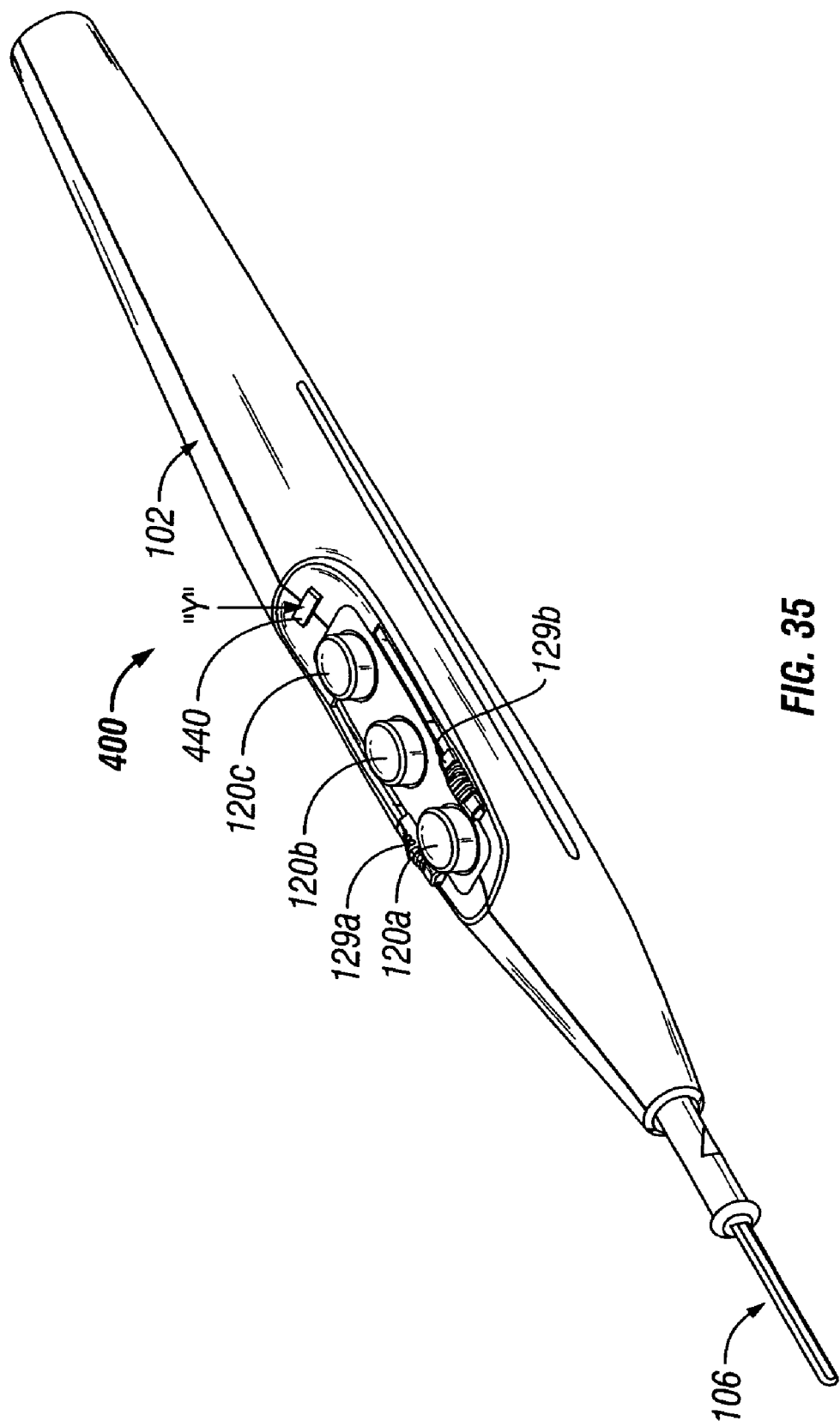
FIG. 35 is a perspective view of an electrosurgical pencil according to an alternate embodiment of the present disclosure.
Figure 36:
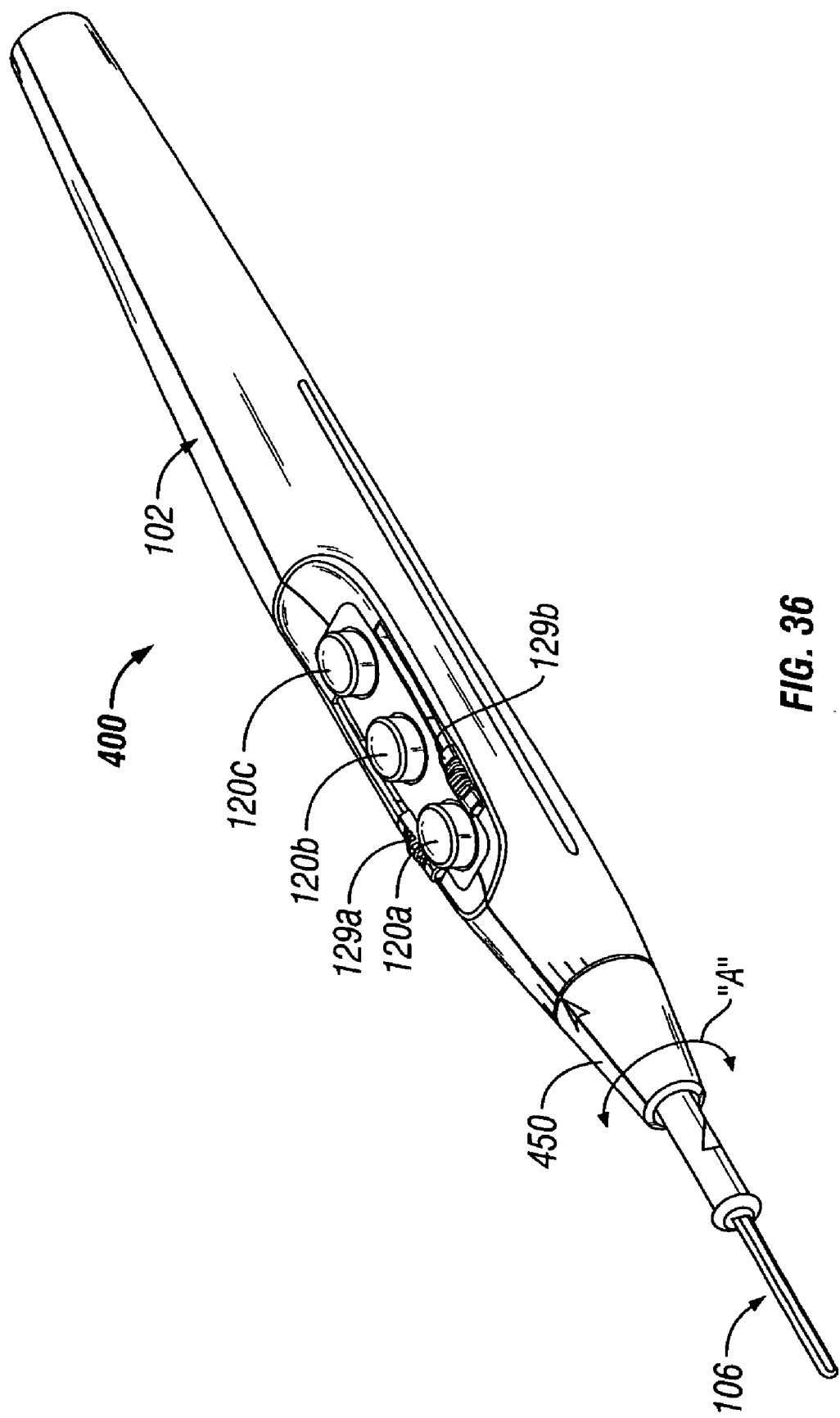
FIG. 36 is a perspective view of an electrosurgical pencil according to still another embodiment of the present disclosure.
Figure 37:
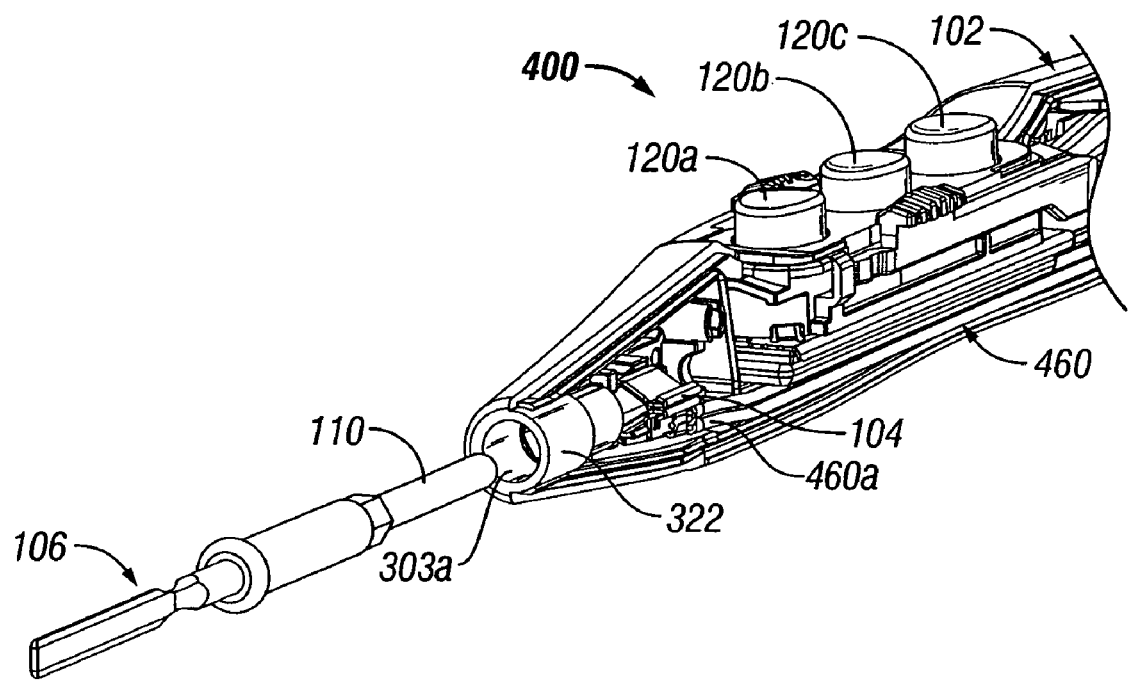
FIG. 37 is a partial, longitudinal, cross-sectional, front perspective view of a distal end of an electrosurgical pencil, in accordance with another embodiment of the present disclosure.

Turning now to FIGS. 35-37, electrosurgical pencils according to alternate embodiments of the present disclosure are shown generally as 400. Electrosurgical pencils 400 are similar to electrosurgical pencils 100 or 300 and thus will only be discussed in detail to the extent necessary to identify differences in construction and operation.

As seen in FIG. 35, electrosurgical pencil 400 includes a range setting selector in the form of a button 440 supported on housing 102. While button selector 440 is shown positioned proximally of activation switches 120a-120c, it is envisioned and within the scope of the present disclosure to place button selector 440 at any convenient, accessible and non-disruptive location on housing 102.

In one embodiment, button selector 440 may be electrically connected to VDN 127 (see FIGS. 9 and 11), or, in an alternate embodiment, button selector 440 may be electrically connected to a separate respective VDN (not shown).

In use, button selector 440 is depressed, as needed, to change the range settings of the energy delivered to electrocautery end effector 106. In other words, depending on the particular shape and/or configuration of electrocautery end effector 106 (e.g., blade, loop, ball, etc.) button selector 440 is depressed in the direction of arrow "Y" in order to cycle through the range setting until the appropriate range setting for the particular electrocautery end effector 106 is selected.

By placing button selector 440 on housing 102 the appropriate range setting for the particular electrocautery end effector 106 may be selected entirely from within the sterile or operative field. Accordingly, during an operative procedure, when the surgeon desires and/or needs to change one electrocautery end effector 106 to an electrocautery end effector of a different shape, the surgeon toggles or cycles through the range settings by pressing button selector 440 until the appropriate range setting is achieved for the corresponding electrocautery end effector 106.

As seen in FIG. 36, electrosurgical pencil 400 may include a selector in the form of a collet 450 operatively supported at a distal end of housing 102. Desirably, the proximal end of electrocautery end effector 106 may be introduced through collet selector 450 to blade receptacle 104 (see FIGS. 8 and 9). Collet selector 450 is rotatably supported on the distal end of housing 102.

In one embodiment, collet selector 450 may be electrically connected to VDN 127 (see FIGS. 9 and 11), or, in an alternate embodiment, collet selector 450 may be electrically connected to a separate respective VDN (not shown).

In use, collet selector 450 is rotated, as needed, to change the range settings of the energy delivered to electrocautery end effector 106. In other words, depending on the particular shape and/or configuration of electrocautery end effector 106 (e.g., blade, loop, ball, etc.) collet selector 450 is rotated in the direction of double-headed arrow "A" in order to select the appropriate range setting for the particular electrocautery end effector 106. Accordingly, during an operative procedure, when the surgeon desires and/or needs to change the electrocautery end effector 106 to an end effector having a different shape, the surgeon rotates collet selector 450 until the appropriate range setting is achieved for the corresponding electrocautery end effector 106.

In an embodiment, as seen in FIG. 37, the range setting selector electrosurgical pencil 400 may include an optical fiber 460 or the like having a distal end 460a in operative association with blade mount 320 disposed in housing 102 and a proximal end (not shown) in operative association with electrosurgical generator "G". In the present embodiment, the proximal end 110 of each individual electrocautery end effector 106 would have a unique color associated therewith (e.g., yellow, red, blue, green, white, black, etc.) and in turn a unique light intensity when proximal end 110 of electrocautery end effector 106 is inserted in blade mount 320.

Accordingly, when the electrocautery end effector 106 is inserted into opening 303a of blade mount 320 and into blade receptacle 104, optical fiber 460 transmits the color and/or the intensity of the light produced by the proximal end 110 of the electrocautery end effector 106 back to the electrosurgical generator "G". The electrosurgical generator "G" will then read the color being transmitted thereto and adjust the range settings to correspond with the range settings desired and/or necessary for particular electrocautery end effector 106 which is connected to the electrosurgical pencil 400. In this embodiment, optical fiber 460 enables automatic selection of the range setting upon insertion of electrocautery end effector 106 into opening 303a of blade mount 320 and/or into blade receptacle 104.

While an optical fiber 460 has been shown and described to automatically select the range settings of the electrosurgical generator "G" upon connection of a particular electrocautery end effector 106 to housing 102, it is envisioned and within the scope of the present disclosure that any system may be provided to achieve automatic establishment of range settings based-upon the insertion of a unique electrocautery end effector. For example, such systems may include machine readable indicia provided on the surface of the electrocautery end effector which is read by a corresponding reader provided in the housing, or a mechanical keying element provided on the surface of the electrocautery end effector which selectively engages complementary receiving elements provided within the housing.

It is further envisioned that any of the electrosurgical pencils disclosed herein can be provided with a lock-out mechanism/system (not shown) wherein when one of the activation switches is depressed, the other remaining activation switches can either not be depressed or can not cause transmission of electrosurgical energy to electrocautery blade 106.

It is also envisioned that the electrosurgical pencil 100 may include a smart recognition technology which communicates with the generator to identify the electrosurgical pencil and communicate various surgical parameters which relate to treating tissue with electrosurgical pencil 100. For example, the electrosurgical pencil 100 may be equipped with a bar code or Aztec code which is readable by the generator and which presets the generator to default parameters associated with treating tissue with electrosurgical pencils. The bar code or Aztec code may also include programmable data which is readable by the generator and which programs the generator to specific electrical parameters prior to use.

Other smart recognition technology is also envisioned which enable the generator to determine the type of instrument being utilized or to insure proper attachment of the instrument to the generator as a safety mechanism. One such safety connector is identified in U.S. patent application Ser. No. 10/718,114, filed Nov. 20, 2003, the entire contents of which being incorporated by reference herein. For example, in addition to the smart recognition technology described above, such a safety connector can include a plug or male portion operatively associated with the electrosurgical pencil and a complementary socket or female portion operatively associated with the electrosurgical generator. Socket portion is "backward compatible" to receive connector portions of electrosurgical pencils disclosed therein and to receive connector portions of prior art electrosurgical instruments.

Turning now to FIGS. 38-50, an electrosurgical system including an electrosurgical pencil according to a further embodiment of the present disclosure is shown generally as 1000. Electrosurgical pencil 1000 is substantially similar to electrosurgical pencil 100 and will only be described in detail herein to the extent necessary to identify differences in construction and/or operation.

Figure 38:
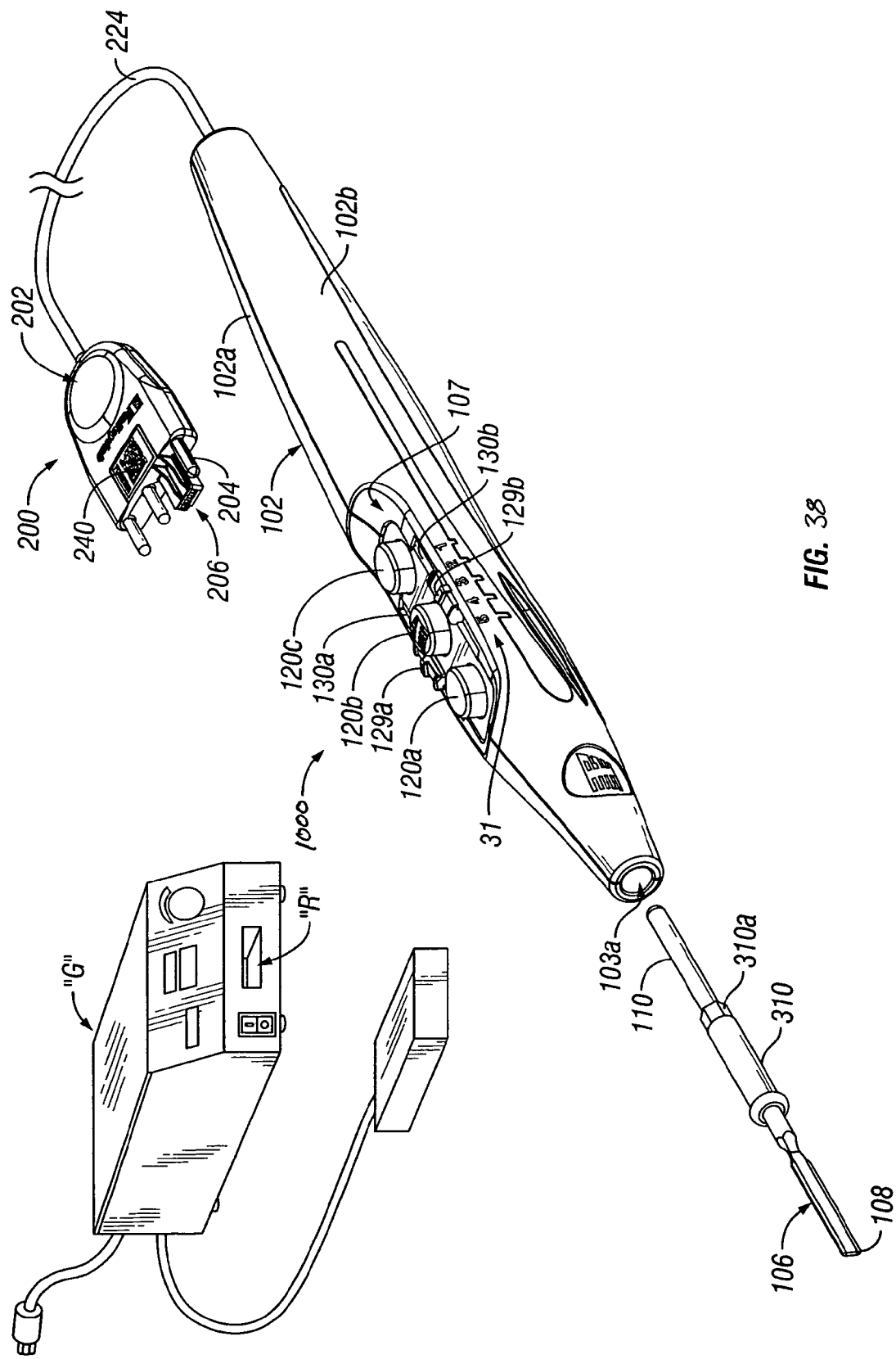
FIG. 38 is a perspective view of an electrosurgical system including an electrosurgical pencil according to a further embodiment of the present disclosure.

As seen in FIGS. 38-50, electrosurgical pencil 1000 includes an elongated housing 102 having a right-half shell section 102a and a left-half shell section 102b. As seen in FIG. 38, when right and left-half shell sections 102a, 102b are connected to one another, a distal opening 103a is defined therebetween, through which an electrode 106 extends, and a proximal opening 103b (see FIG. 41) is defined therebetween, through which connecting cable 224 (see FIG. 38) extends. Right and left-half shell sections 102a, 102b are welded to one another along a portion of a length of a top edge thereof and along an entire length of a bottom edge thereof. Connecting cable 224 is held in place between right and left-half shell sections 102a, 102b by a friction-fit engagement in a non-hermetically sealed manner.

As seen in FIGS. 41, 43, 45 and 46, electrosurgical pencil 1000 further includes an electrode receptacle 104 disposed at a distal end of housing 102, and a replaceable electrode 106 operatively and removably connectable to electrode receptacle 104.

Electrode 106 is in the form of a blade. When coupled to electrode receptacle 104, a distal end portion 108 of electrode 106 extends distally beyond electrode receptacle 104 while a proximal end portion 110 of electrode 106 is selectively retained by electrode receptacle 104 within the distal end of housing 102. Electrode 106 is fabricated from a stainless steel rod having a silicone elastomer coating. Electrode receptacle 104 electrically interconnects electrode 106 to electrosurgical generator "G".

With continued reference to FIGS. 38-50, electrosurgical pencil 1000 includes three activation buttons 120a-120c, each of which is reciprocally supported in a carrier 121 (see FIG. 41) of a controller unit which is supported in housing 102.

Each activation button 120a-120c includes a portion which extends through an upper surface of housing 102.

Figure 41:
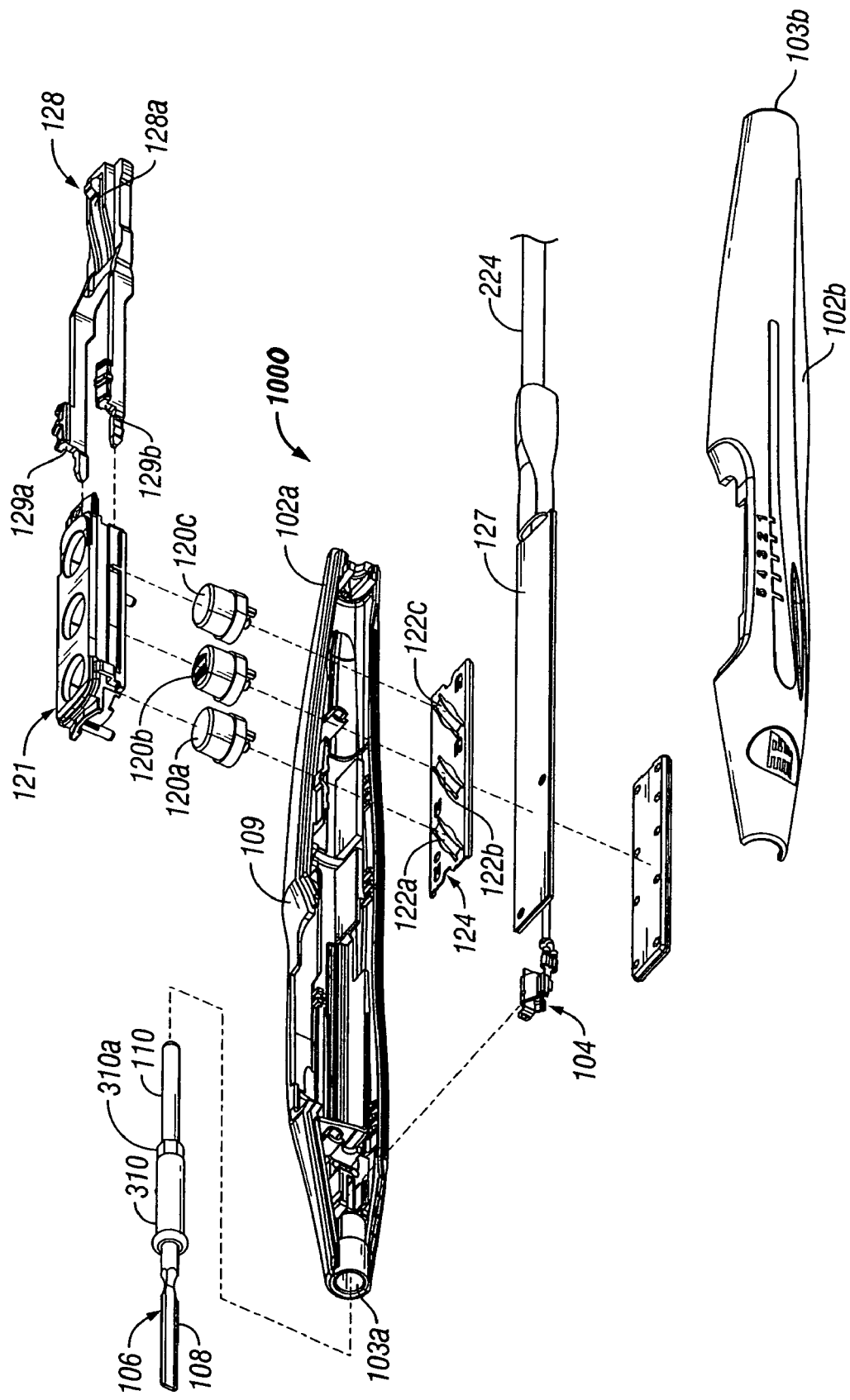
FIG. 41 is an exploded perspective view of the electrosurgical pencil of FIGS. 38-40.

As seen in FIG. 41, each activation button 120a-120c is operatively supported on a respective tactile element 122a-122c formed in a switch plate 124. Each tactile element 122a-122c is in the form of an arcuate bridge projecting upwardly from a top surface of switch plate 124 to contact a respective button 120a-120c. Each tactile element 122a-122c has a first, un-biased condition in which the tactile element 122a-122c projects upwardly from the top surface of switch plate 124 and a second, biased condition in which the tactile element 122a-122c is deflected downwardly, by a respective activation button 120a-120c, against a voltage divider network 127, to close a switch.

Figure 42:
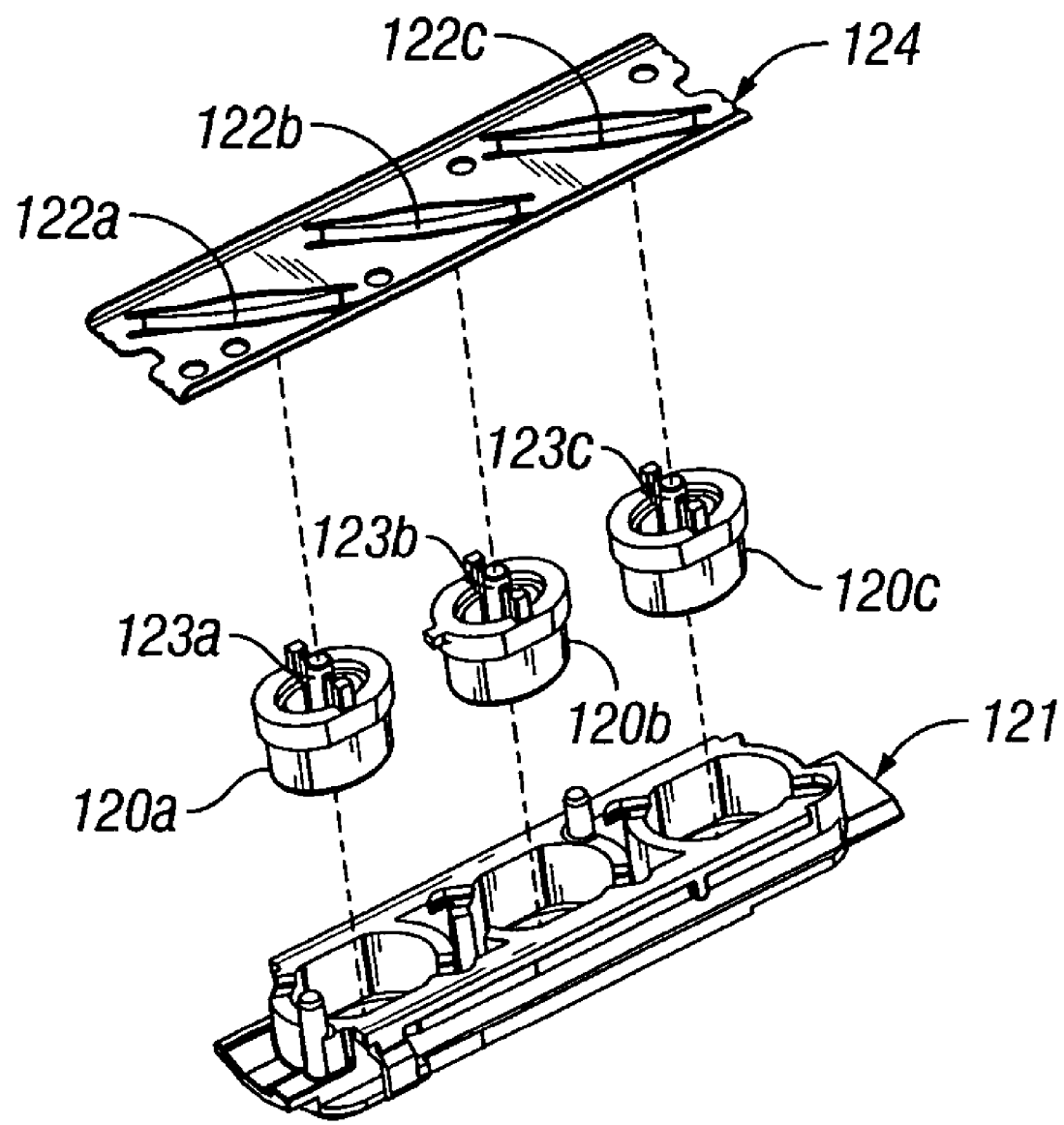
FIG. 42 is an exploded perspective view of a controller unit for the electrosurgical pencil of FIGS. 38-41.

As seen in FIGS. 42-44, each activation button 120a-120c includes a stem 123a-123c, respectively, which stem 123a-123c is in operative engagement with a respective tactile element 122a-122c.

Each activation switch 120a-120c controls the transmission of RF electrical energy supplied from generator "G" to electrode 106. Switch plate 124 is positioned over the top of a voltage divider network 127 (hereinafter "VDN 127") such that tactile elements 122a-122c are in operative association therewith. VDN 127 is a film-type potentiometer which forms the basis of a switch closure assembly.

As seen in FIG. 42, VDN 127 includes a pair of layers 140a, 140b of resilient material each supporting a plurality of electrical contacts 142a, 142b thereon. Electrical contacts 142a from an upper layer 140a of VDN 127 are in juxtaposed electrical relation with respect to electrical contacts 142b from a lower layer 140b of VDN 127. The electrical contacts 142a, 142b of the upper and the lower layers 140a, 140b of VDN 127 are in juxtaposed relation with respective tactile elements 122a-122c.

Upper and lower layers 140a, 140b of VDN 127 are separated by a dividing layer 140c. Dividing layer 140c includes a first series of apertures 142c formed therein which are in vertical registration with electrical contacts 142a, 142b. Dividing layer 140c includes a second aperture 144c formed therein which is in vertical registration between electrical contacts 144a provided on upper layer 140a and a variable resistance element 144d provided on lower layer 140b. Upper layer 140a, lower layer 140b, and dividing layer 140c are supported on a support layer 140d.

In operation, and depending on the particular electrosurgical function desired, the surgeon depresses one of activation buttons 120a-120c, in the direction indicated by arrow "Y" (see FIGS. 43 and 44) thereby urging and/or deflecting a corresponding tactile element 122a-122c against VDN 127 and thereby causing the respective electrical contact 142a of upper layer 140a to electrically engage the respective electrical contact 142b of the lower layer 140b. In so doing, a respective characteristic voltage is generated and measured by electrosurgical generator "G". In turn, depending on the characteristic voltage generated, generator "G" selects and transmits an appropriate waveform output to electrocautery blade 106 via RF line 220 (see FIGS. 48 and 49).

Activation buttons 120a-120c are operable to control the mode and/or "waveform duty cycle" to achieve a desired surgical intent. First activation button 120a is set to generate a first characteristic voltage in VDN 127 which is measured by electrosurgical generator "G" which generator "G" in turn transmits a unique duty cycle and/or waveform shape which produces a cutting and/or dissecting effect/function. Second activation button 120b is set to generate a second characteristic voltage in VDN 127 which is measured by electrosurgical generator "G" which generator "G" in turn transmits a unique duty cycle and/or waveform shape which produces a division with hemostatic effect/function. Third activation button 120c is set to generate a third characteristic voltage in VDN 127 which is measured by electrosurgical generator "G" which generator "G" in turn transmits a unique duty cycle and/or waveform shape which produces a hemostatic/coagulation effect/function.

The division with hemostatic effect/function is defined as having waveforms with a duty cycle from about 12% to about 75%. The hemostatic/coagulation effect/function is defined as having waveforms with a duty cycle from about 1% to about 12%. The cutting and/or dissecting effect/function is defined as having waveforms with a duty cycle from about 75% to about 100%.

The division with hemostatic effect/function is transmitted and/or delivered in discrete energy packets. The discrete energy packets include an amplification or ramp-up period and a degradation or ramp-down period which is reduced and/or eliminated. The discrete energy packets delivered during the transmission of the dividing with hemostatic effect/function include an almost instantaneous amplification of energy and an almost instantaneous degradation of energy.

The division with hemostatic effect/function has a higher duty cycle than the cutting and/or dissecting effect/function. The division with hemostatic effect/function includes four (4) pulses per rep rate as compared to one (1) pulse per rep rate for a fulgurate or spray effect/function. The division with hemostatic effect/function differs from the blending effect/function in that the division with hemostatic effect/function has a very low stored energy on the output as compared to the blending effect/function. Accordingly, the division with hemostatic effect/function has a higher crest factor as compared to the blending effect/function and a more continuous output as compared to coagulating effect/function.

As seen in FIGS. 38-41 and 43-45, electrosurgical pencil 1000 includes an intensity controller 128 slidingly supported in housing 102. Intensity controller 128 includes a pair of nubs 129a, 129b which are slidingly supported, one each, in respective guide channels 130a, 130b (see FIG. 38). Guide channels 130a, 130b are defined between respective right and left-half shell sections 102a, 102b and carrier 121 when right and left-half sections 102a, 102b are joined together around carrier 121 and ultrasonically welded to one another. Guide channels 130a, 130b are formed on either side of activations buttons 120a-120c allowing the surgeon to operate electrosurgical pencil 100 with either the right or the left hand.

Figure 50:
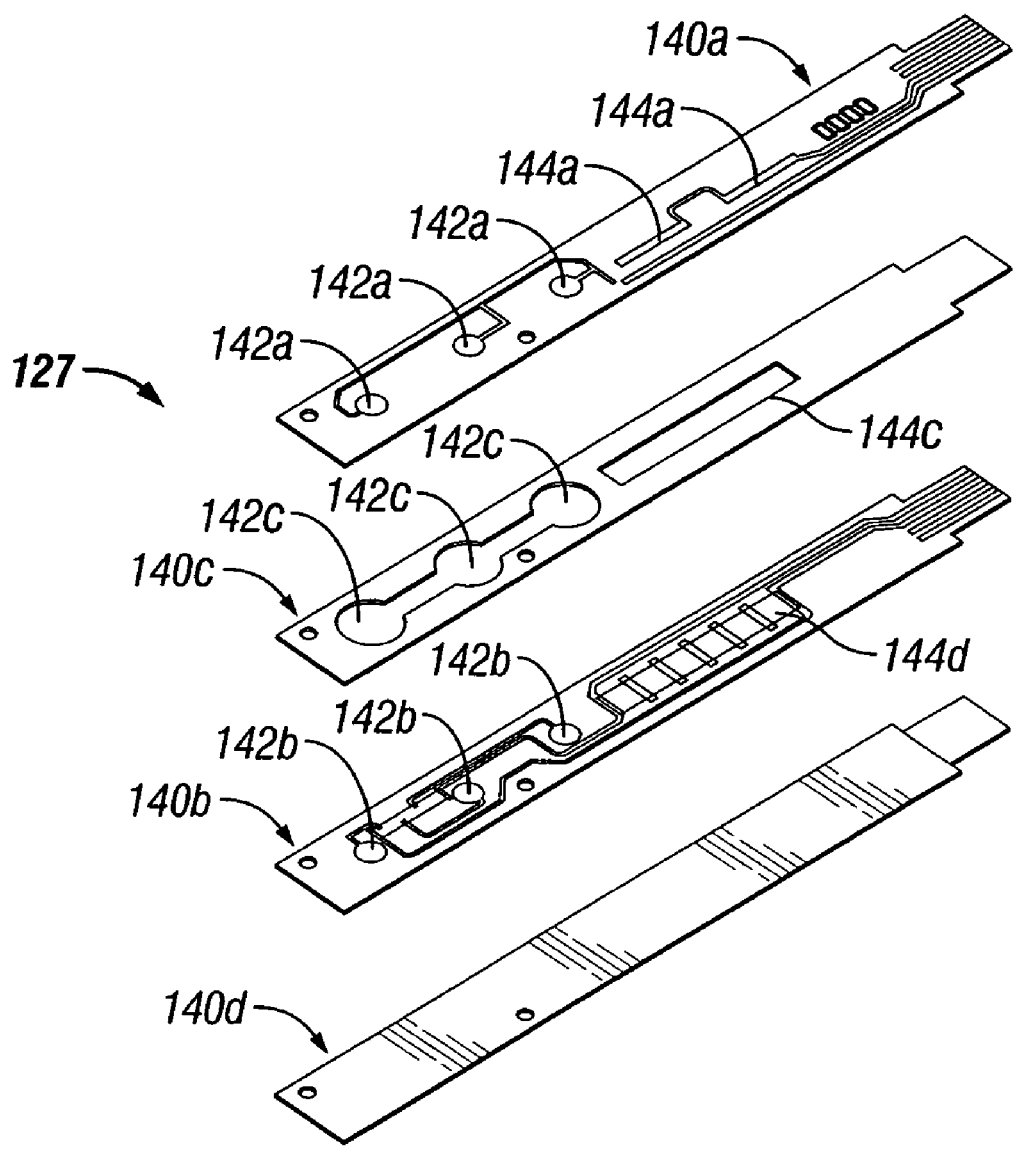
FIG. 50 is an exploded perspective view of the voltage divider network of the electrosurgical pencil of FIGS. 38-46.

As seen in FIG. 43, intensity controller 128 includes a nub 129c extending from a bottom surface thereof which contacts and presses into or against VDN 127. As seen in FIG. 50, VDN 127 includes electrical contacts 144a provided on upper layer 140a and lower layer 140b. In this manner, as intensity controller 128 is displaced in a distal and proximal direction relative to housing 102, third nub 129c moves along VDN 127, thereby pressing electrical contact 144a from upper layer 140a of VDN 127 against resistance element 144b of lower layer 140b of VDN 127. In so doing, a resistance value of resistance element 144b is changed thereby changing the value of the voltage measured by electrosurgical generator "G". The electrosurgical generator "G" in turn varies the intensity of the waveform being transmitted to electrode 106.

Intensity controller 128 in combination with VDN 127 functions as a slide potentiometer. Intensity controller 128 has an initial position wherein nubs 129a, 129b are at a proximal-most position which corresponds to a relatively low intensity setting, a final position wherein nubs 129a, 129b are at a distal-most position which corresponds to a relatively high intensity setting, and a plurality of intermediate positions wherein nubs 129a, 129b are at positions between the distal-most position and the proximal-most position corresponding to various intermediate intensity settings.

Slidable manipulation or movement of intensity controller 128 adjusts the power parameters (e.g., voltage, power and/or current intensity) and/or the power verses impedance curve shape to affect the output intensity of the waveform. The greater intensity controller 128 is displaced in a distal direction the greater the level of the power parameters for the waveforms are transmitted to electrode 106. Current intensities range from about 60 mA to about 240 mA and have a typical tissue impedance of about 2K ohms. A waveform with an intensity level of 60 mA provides very light and/or minimal cutting/dividing/coagulating effects. An intensity level of 240 mA provides very aggressive cutting/dividing/coagulating effects.

In order to vary the intensity of the power parameters of electrosurgical pencil 100, the surgeon displaces intensity controller 128, by manipulating at least one of nubs 129a, 129b, in either of the directions indicated by double-headed arrow "X" (see FIGS. 43 and 44, supra).

Intensity controller 128 is operable to provide a degree of tactile feedback by the inter-engagement of resilient finger 128a of intensity controller 128 in detents 131 formed along an inner surface of right-half shell section 102a.

As seen in FIGS. 38-42, housing 102 includes a series of indicia 31 provided thereon which are visible to the user and which reflect the relative level of intensity that is to be transmitted. Indicia 31 are provided alongside guide channels 130a, 130b and are spaced therealong to correspond substantially with detents 131 which provide the tactile feedback to intensity controller 128.

Figure 48:
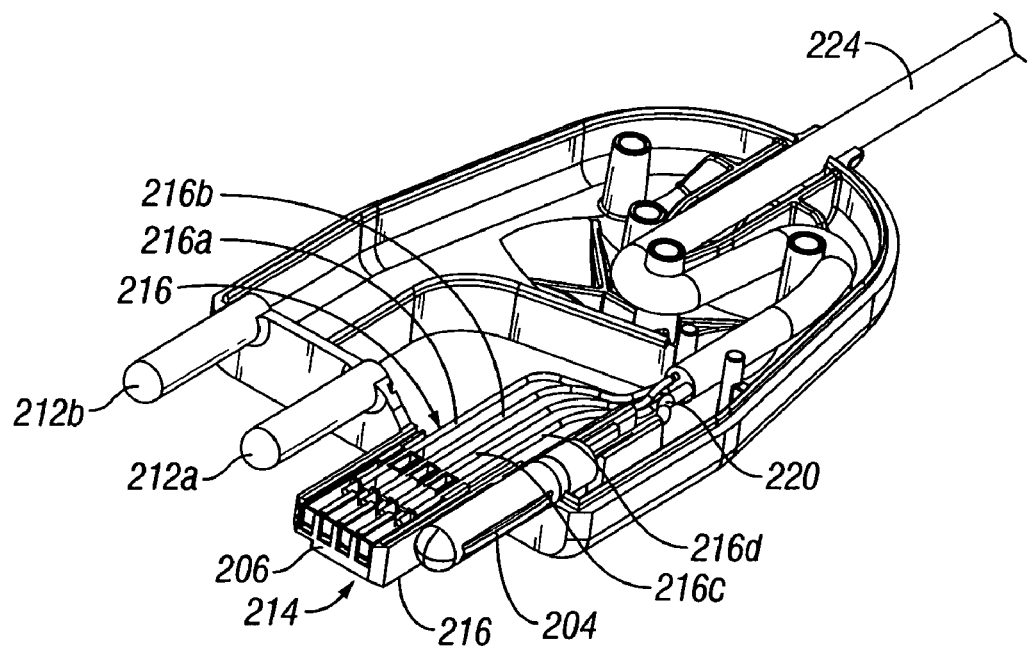
FIG. 48 is an enlarged perspective view of the plug assembly of FIG. 47, with an upper half-section removed therefrom.

As seen below in FIGS. 48 and 49, an RF line 220 for transmitting RF energy to electrode 106 is provided and is directly electrically connected to electrode receptacle 104 for connection to proximal end 110 of electrode 106. Since RF line 220 is directly connected to electrode receptacle 104, RF line 220 bypasses VDN 127 and thus isolates VDN 127 and control wires 216a-216d.

Figure 49:
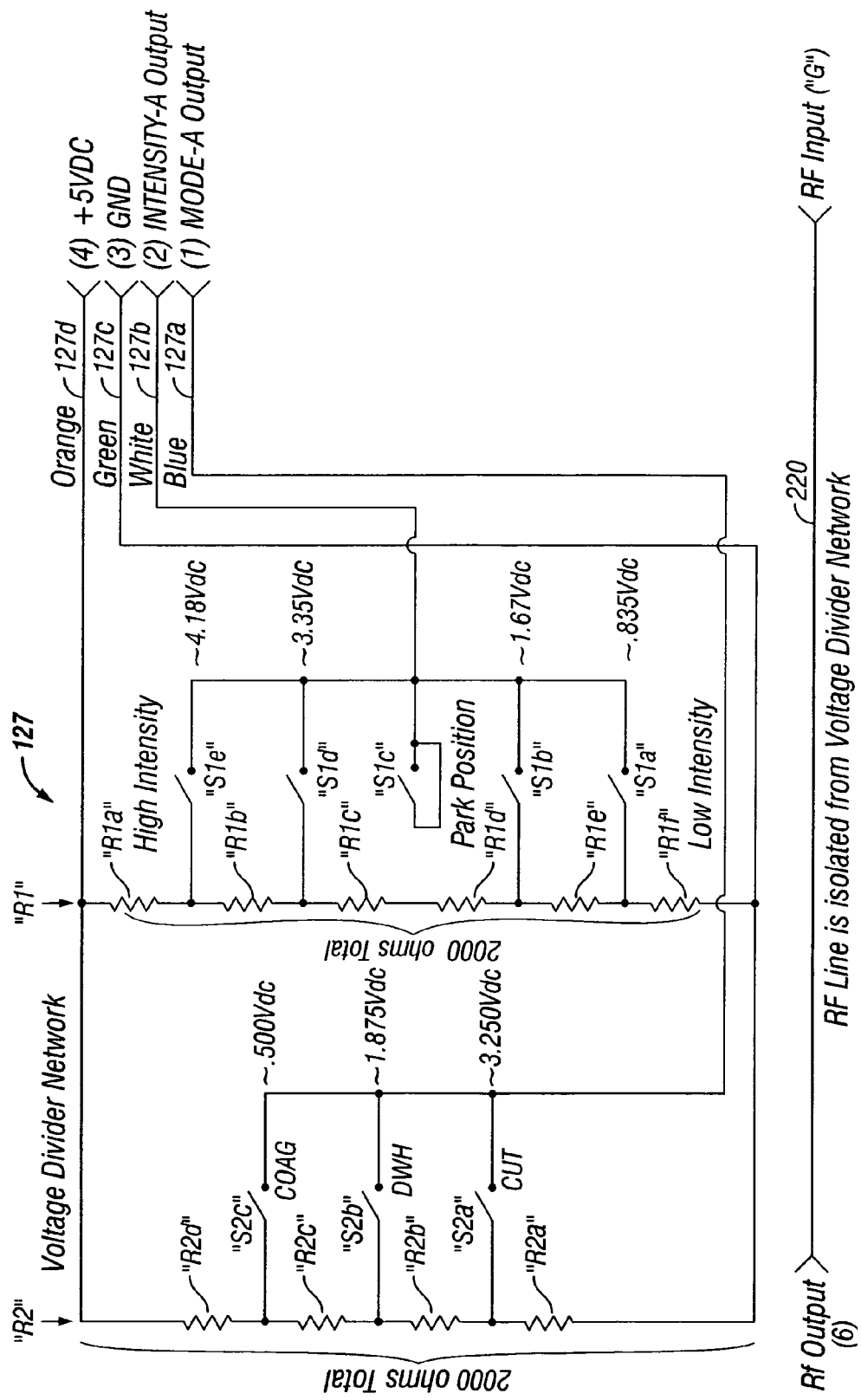
FIG. 49 is a schematic illustration of a voltage divider network for use with the electrosurgical pencil of FIGS. 38-46.

With reference to FIG. 49, VDN 127 includes a first transmission line 127a for identifying the various modes of electrosurgical pencil 1000; a second transmission line 127b for identifying the various intensities of electrosurgical pencil 1000; a third transmission line 127c to function as a ground for VDN 127; and a fourth transmission line 127d which transmits up to about +5 volts to VDN 127.

VDN 127 includes a first variable resistor "R1" having a maximum resistance of 2000 ohms. First resistor "R1" is a variable resistor which is represented in FIG. 49 as six (6) individual resistors "R1a-R1f" connected between third transmission line 127c and fourth transmission line 127d. Each resistor "R1a-R1f" of the first set of resistors has a resistance of 333 ohms. First resistor "R1" is selectively actuatable by intensity controller 128 at a plurality of locations along the length thereof. The locations along the length of the first resistor "R1" correspond to the detents 131 formed along the inner surface of right-half shell section 102a. (see FIG. 43) These locations along the length of resistor "R1" are represented as a first set of switches "S1a-S1e". In operation, as intensity controller 128 is moved along first resistor "R1" the value of the resistance of first resistor "R1" is changed. The change of the resistance value of first resistor "R1" is represented in FIG. 49 as the closing of a switch "S1a-S1e". The change in resistance of first resistor "R1" causes a change in voltage which is measured by electrosurgical generator "G" which, in turn, transmits an RF energy at a unique intensity to electrosurgical pencil 1000.

When intensity controller 128 is moved to a third of middle position along first resistor "R1", corresponding to switch "S1c", a "park position" is established in which no resistance is present. Accordingly, electrosurgical generator "G" measures a maximum voltage value of zero volts.

VDN 127 further includes a second variable resistor "R2" having a maximum resistance of 2000 ohms. Second resistor "R2" is represented in FIG. 49 as four (4) individual resistors "R2a-R2d" connected between third transmission line 127c, and fourth transmission line 127d. Resistor "R2a" has a resistance of 200 ohms, resistor "R2b" has a resistance of 550 ohms, resistor "R2c" has a resistance of 550 ohms, and resistor "R2d" has a resistance of 700 ohms.

Second resistor "R2" is selectively actuatable by any one of activation buttons 120a-120c. The location where second resistor "R2" is actuated by an activation button 120a-120c is represented as a second set of switches "S2a-S2c". In operation, depending on which switch "S2a-S2c" of the second set of switches "S2" is closed, by actuation of a particular activation button 120a-120c, the value of the resistance of second resistor "R2" is changed. The change of the resistance value of second resistor "R2" causes a change in voltage which is measured by electrosurgical generator "G" which, in turn, activates and transmits a different mode of operation to electrosurgical pencil 1000.

In operation, if more than one activation button 120a-120c is actuated simultaneously (i.e., a "multi-key activation" scenario), electrosurgical generator "G" will measure a unique voltage which does not correspond to any preset known voltage stored therein and thus does not activate or transmit any mode of operation to electrosurgical pencil 1000.

In use, depending on which activation button 120a-120c is depressed a respective tactile element 122a-122c is pressed, via a respective stem 123a-123c, into contact with VDN 127. The depressed activation button 120a-120c electrically engages juxtaposed electrical contacts of VDN 127 thereby changing the value of the second resistor. Depending on the value of the resistance of the second resistor "R2" a characteristic voltage is generated and measured by electrosurgical generator "G" via first transmission line 127a and first control wire 216a (see FIGS. 48 and 49).

In order to vary the intensity of the power parameters of electrosurgical pencil 100, the surgeon displaces intensity controller 128 as described above, thereby changing the value of the first resistor "R1". Depending on the value of the resistance of first resistor "R1" a characteristic voltage is generated and measured by electrosurgical generator "G" via second transmission line 127b and second control wire 216b (see FIGS. 48 and 49).

Turning back to FIG. 38, electrosurgical pencil 100 is coupled to electrosurgical generator "G" via a plug assembly 200. As seen in FIGS. 38 and 47-49, plug assembly 200 includes a housing portion 202, and a connecting cable 224 electrically interconnecting housing portion 202 to device 1000.

Housing portion 202 includes a first half-section 202a and a second half-section 202b operatively engageable with one another. A power pin 204 of plug assembly 200 extends distally from housing portion 202. Power pin 204 is positioned off center of housing portion 202. Plug assembly 200 further includes a pair of position pins 212 also extending from housing portion 202. A first position pin 212a is positioned in close proximity to a center of housing portion 202 and a second position pin 212b is positioned to be off center of and in close proximity to an opposite side edge of housing portion 202 as compared to power pin 204.

Plug assembly 200 further includes a prong 214 extending from housing portion 202. Prong 214 is positioned between power pin 204 and first position pin 212a. Prong 214 is configured and adapted to retain electrical contacts 206 therein such that a portion of each contact 206 is exposed along a front or distal edge thereof.

Since prong 214 extends from between power pin 204 and first position pin 212a housing portion 202 of plug assembly 200 will not enter connector receptacle "R" of electrosurgical generator "G" unless housing portion 202 is in a proper orientation.

Connecting cable 224 includes an RF line 220 electrically connected to power pin 204, and control wires 216a-216d electrically connected to a respective contact 206. Each control wire 216a-216d is attached individually and separately to a respective contact 206 of prong 214.

Figure 47:
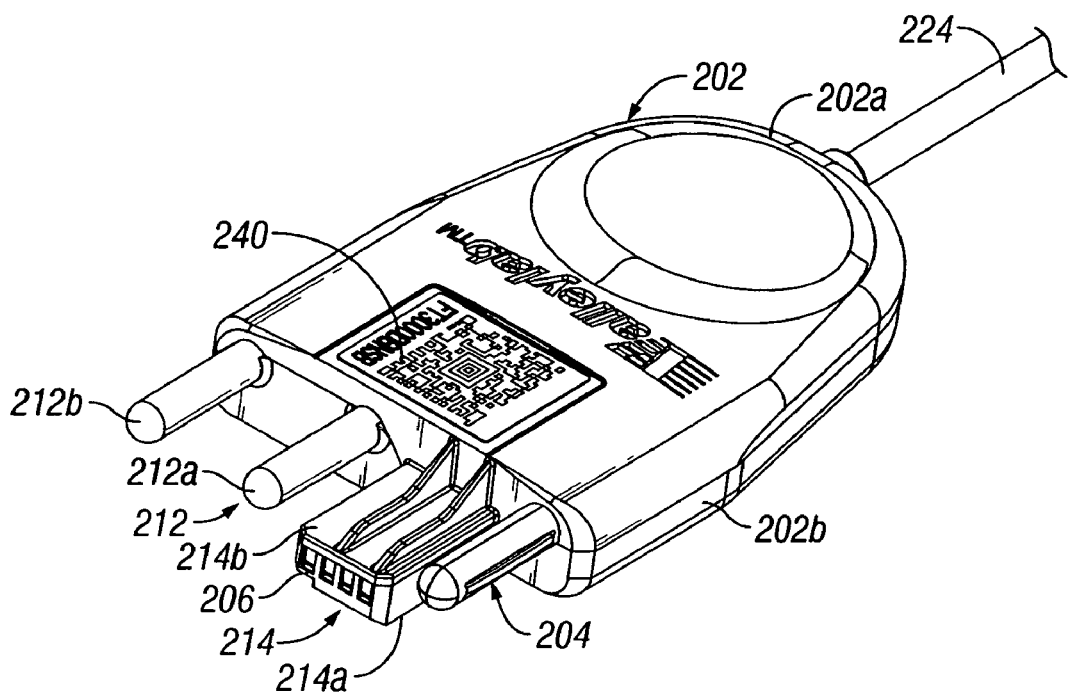
FIG. 47 is a perspective view of a plug assembly of the electrosurgical pencil of FIGS. 38-46.

Electrosurgical pencil 1000 includes smart recognition technology provided on plug 200 which communicates with the generator "G" to identify the electrosurgical pencil and communicate various surgical parameters which relate to treating tissue with electrosurgical pencil 100. As seen in FIGS. 38 and 47, the smart recognition technology includes an Aztec code 240 (see FIG. 47 above) which is optically readable by the generator "G" and which identifies electrosurgical pencil 1000 and which presets the generator "G" to default parameters associated with treating tissue with this particular electrosurgical pencil 1000.

Figure 45:
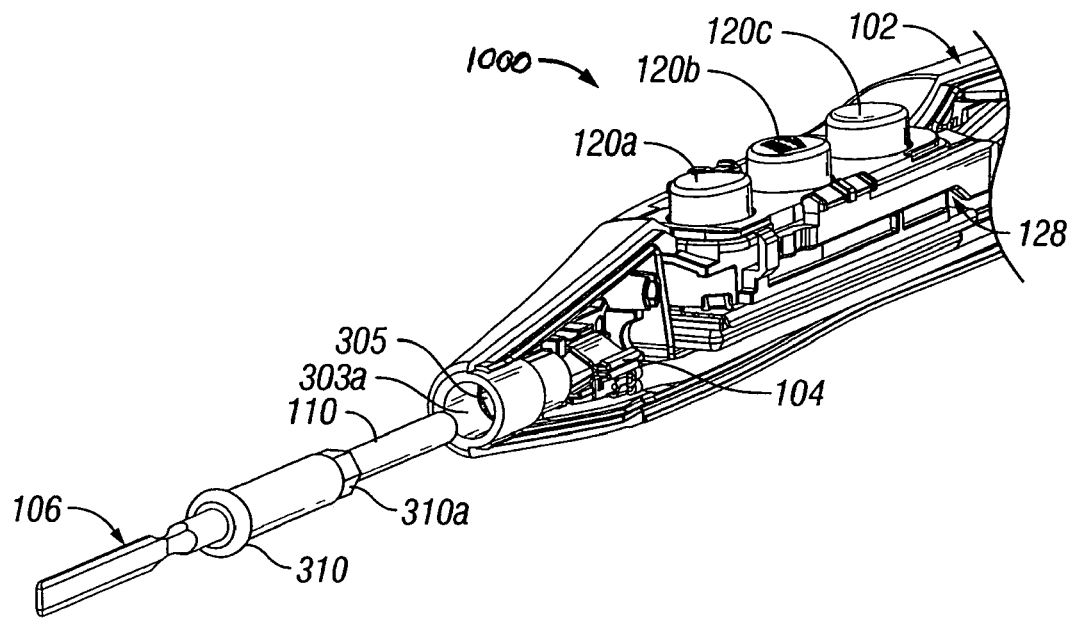
FIG. 45 is a partial, longitudinal, cross-sectional, front perspective view of a distal end of the electrosurgical pencil of FIGS. 38-44.
Figure 46:
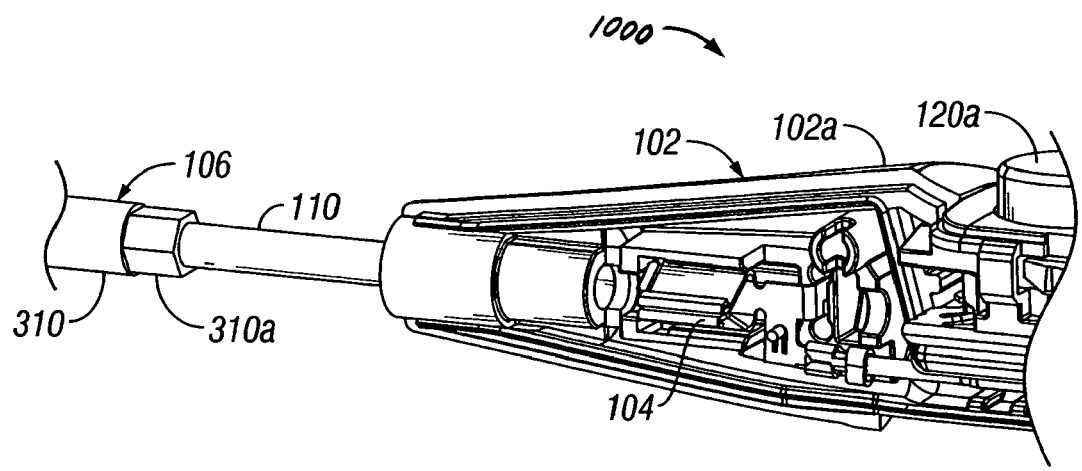
FIG. 46 is a partial, longitudinal, cross-sectional, side elevational view of a distal end of the electrosurgical pencil of FIGS. 38-45.

As seen in FIG. 45, open distal end 103a of electrosurgical pencil 100 defines a non-circular inner profile 305. Meanwhile, electrode 106 is supported in a collar 310 having a shaped outer surface 310a configured and dimensioned to complement the inner profile 305 of open distal end 103a. Open distal end 103a of housing 102 defines a hexagonal inner profile 305 and collar 310 defines a hexagonal shaped outer surface 310a.

It is also envisioned that the current controls may be based on current density or designed to deliver a specific current for a defined surface area (amp/cm$^2$).

Although the subject apparatus has been described with respect to preferred embodiments, it will be readily apparent, to those having ordinary skill in the art to which it appertains, that changes and modifications may be made thereto without departing from the spirit or scope of the subject apparatus.

What is claimed is:

1. An electrosurgical pencil, comprising:
   an elongated housing;
   at least one type of electrocautery end effector removably supportable within the housing and extending distally from the housing, the electrocautery end effector being connected to a source of electrosurgical energy adapted for use with multiple types of electrocautery end effectors that are configured to operate within a corresponding range setting of energy;
   a plurality of activation switches supported on the housing for controlling the amount of electrosurgical energy transmitted to the at least one electrocautery end effector;
   an intensity controller supported on the housing and configured to adjust power parameters associated with the transmitted electrosurgical energy; and
   a single selector independently operable from each of the plurality of activation switches and the intensity controller and supported on the housing for selecting a range setting of energy to be delivered from the source of electrosurgical energy to the at least one type of electrocautery end effector, wherein the selector is actuatable to select one of a plurality of range settings of energy corresponding to a selected one of the multiple types of electrocautery end effectors connected to the housing,
   wherein the selector is configured such that when the selector is pressed, the selector cycles through the plurality of range settings of energy until an appropriate range setting is achieved for the at least one type of electrocautery end effector such that the at least one type of electrocautery end effector is operable within that range setting of energy associated therewith.

2. The electrosurgical pencil according to claim 1, wherein the selector is at least one of a button depressably supported on the housing or a collet rotatably supported on the housing, wherein the range settings are selected by at least one of depressing the button and rotating the collet.

3. The electrosurgical pencil according to claim 2, wherein each activation switch is configured and adapted to selectively complete a control loop extending from the source of electrosurgical energy upon actuation thereof.

4. The electrosurgical pencil according to claim 3, wherein actuation of at least one of the plurality of activation switches produces a division with hemostatic effect at the electrocautery end effector.

5. The electrosurgical pencil according to claim 4, further comprising at least one voltage divider network supported on the housing, the at least one voltage divider network being electrically connected to the source of electrosurgical energy and in electrical communication with the intensity controller and the plurality of activation switches for respectively controlling at least one of an intensity of electrosurgical energy being delivered to the electrosurgical pencil and a mode of electrosurgical energy being delivered to the electrosurgical pencil.

6. The electrosurgical pencil according to claim 5, wherein the selector is operatively connected to the voltage divider network.

7. The electrosurgical pencil according to claim 6, wherein the division with hemostatic effect is transmitted in discrete packets of energy.

8. The electrosurgical pencil according to claim 7, wherein the energy packet has a substantially instantaneous amplification.

9. The electrosurgical pencil according to claim 8, wherein the energy packet has a substantially instantaneous degradation.

10. The electrosurgical pencil according to claim 6, wherein the housing defines an open distal end for selectively receiving a proximal end of the electrocautery end effector therein, and wherein the open distal end of the housing has a non-circular inner profile.

11. The electrosurgical pencil according to claim 10, further comprising a collar operatively supporting the electrocautery end effector, the collar having a shaped outer surface complementing the shaped inner profile of the distal open end of the housing.

12. The electrosurgical pencil according to claim 11, wherein the collar and the inner profile of the distal open end of the housing have complementary ovular, triangular, rectangular, hexagonal, toothed, multi-faceted profiles.

13. The electrosurgical pencil according to claim 12, further comprising an end effector receptacle configured and adapted to selectively engage a proximal end of the electrocautery end effector.

14. The electrosurgical pencil according to claim 6, further comprising a stabilizer operatively disposed within the housing for increasing retention forces acting on the proximal end of the electrocautery end effector, the stabilizer defining a passage therein configured and adapted to selectively receive a proximal end of the electrocautery end effector.

15. The electrosurgical pencil according to claim 14, wherein the stabilizer is fabricated from a compliant polymeric material.

16. The electrosurgical pencil according to claim 6, wherein the at least one voltage divider network being electrically connected to the source of electrosurgical energy for controlling the intensity of electrosurgical energy being delivered to the plurality of activation switches from the source of electrosurgical energy and for controlling the intensity of electrosurgical energy delivered to the plurality of activation switches returning from the electrocautery end effector, the at least one voltage divider network comprises at least one return control wire electrically inter-connecting the electrocautery end effector and the source of electrosurgical energy, the return control wire transmitting excess electrosurgical energy from the electrocautery end effector to the source of electrosurgical energy.

17. The electrosurgical pencil according to claim 16, wherein the intensity controller includes a slide potentiometer that is supported on the housing and in operative communication with the voltage divider network and movable therealong.

18. The electrosurgical pencil according to claim 17, wherein the plurality of activation switches define a first resistor network disposed within the housing, and wherein the slide potentiometer defines a second resistor network disposed within the housing.

19. The electrosurgical pencil according to claim 18, wherein the slide potentiometer simultaneously controls the intensity of electrosurgical energy delivered to the plurality of activation switches such that the intensity of electrosurgical energy delivered to the plurality of activation switches is equal to a value of the intensity controller.

20. The electrosurgical pencil according to claim 19, wherein at least one activation switch is configured and adapted to control a waveform duty cycle to achieve a desired surgical intent.

21. The electrosurgical pencil according to claim 20, further including three mode activation switches supported on the housing.

22. The electrosurgical pencil according to claim 21, wherein each mode activation switch, when actuated, generates a characteristic voltage which is measured by the source of electrosurgical energy, the source of electrosurgical energy in turn transmits a corresponding waveform duty cycle to the electrosurgical pencil to perform an electrosurgical procedure.

23. The electrosurgical pencil according to claim 21, wherein a first activation switch, when actuated, generates a first characteristic voltage measured by the source of electrosurgical energy, the source of electrosurgical energy in turn transmits a waveform duty cycle which produces a cutting effect; a second activation switch, when actuated, generates a second characteristic voltage measured by the source of electrosurgical energy, the source of electrosurgical energy in turn transmits a waveform duty cycle which produces a division with hemostatic effect; and wherein a third activation switch, when actuated, generates a third characteristic voltage measured by the source of electrosurgical energy, the source of electrosurgical energy in turn transmits a waveform duty cycle which produces a coagulating effect.

24. The electrosurgical pencil according to claim 5, wherein the voltage divider network is a potentiometer.

25. The electrosurgical pencil according to claim 24, further including a molded hand grip operatively supported on the housing.

26. The electrosurgical pencil according to claim 25, wherein the hand grip is shaped and dimensioned to reduce fatigue on the hand of the user.

27. The electrosurgical pencil according to claim 26, further comprising:
    indicia provided on the housing indicating a level of intensity of the energy being delivered to the electrocautery end effector.

28. The electrosurgical pencil according to claim 27, wherein the indicia is located along a path of travel of the slide potentiometer.

29. The electrosurgical pencil according to claim 1, wherein the selector is an optical fiber including a distal end supported in the housing for reading a light intensity from a proximal end of the electrocautery end effector when the electrocautery end effector is connected to the housing.

30. The electrosurgical pencil according to claim 29, wherein a proximal end of each electrocautery end effector includes a unique color associated therewith, wherein each color produces a different light intensity.

31. The electrosurgical pencil according to claim 30, wherein when the electrocautery end effector is connected to the housing, the optical fiber transmits the light intensity to the electrosurgical generator.

32. The electrosurgical pencil according to claim 31, wherein the electrosurgical generator adjusts the range settings based on the light intensity transmitted thereto.

* * * * *